(12) United States Patent
Bajpai et al.

(10) Patent No.: US 12,727,618 B2
(45) **Date of Patent: *Sep. 8, 2026**

(54) PORTABLE VAPORIZATION MODULE, DEVICE, CONTAINER, AND METHODS

(71) Applicant: Puff Corporation, Los Angeles, CA (US)

(72) Inventors: Avinash Bajpai, Aguora Hills, CA (US); Siddhant Waghmare, Los Angeles, CA (US)

(73) Assignee: Puff Corporation, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/539,293

(22) Filed: Feb. 13, 2026

(65) Prior Publication Data

US 2026/0174145 A1 Jun. 25, 2026

Related U.S. Application Data

(63) Continuation of application No. 18/941,891, filed on Nov. 8, 2024, which is a continuation of application (Continued)

(51) Int. Cl.
*A24F 40/46* (2020.01)
*A24F 1/00* (2006.01)

(Continued)

(52) U.S. Cl.
CPC ................ *A24F 40/46* (2020.01); *A24F 1/00* (2013.01); *A24F 7/00* (2013.01); *A24F 40/40* (2020.01);

(Continued)

(58) Field of Classification Search
CPC .......... A24F 40/40; A24F 40/42; A24F 40/46; A24F 5/00
See application file for complete search history.

(56) References Cited

U.S. PATENT DOCUMENTS 10,231,483 B2 3/2019 Garcia
10,321,714 B1 6/2019 Kane (Continued)

FOREIGN PATENT DOCUMENTS

CN 203872999 U 10/2014
CN 206472843 U 9/2017

(Continued)

OTHER PUBLICATIONS

Puff Co., Peak Atomizer Assembly posted on Instagram retrieved from www.instagram.com/p/BfMk5MKIBp1/ Feb. 14, 2018.

(Continued)

*Primary Examiner* — Hae Moon Hyeon
(74) *Attorney, Agent, or Firm* — Bryan Cave Leighton Paisner LLP

(57) ABSTRACT

Aspects of the present invention relate to a portable electronic vaporizing device for use in the vaporization of substances, as well as a container for holding and heating a vaporizable product. Methods of using such a device and a removably attachable vaporization module that is compatible with the device are provided. A method of heating vaporizable substances is also provided.

27 Claims, 40 Drawing Sheets

Related U.S. Application Data

No. 18/136,684, filed on Apr. 19, 2023, now Pat. No. 12,137,742, which is a continuation of application No. 17/861,131, filed on Jul. 8, 2022, now Pat. No. 11,659,865, which is a continuation of application No. PCT/US2022/028122, filed on May 6, 2022, which is a continuation of application No. 17/407,446, filed on Aug. 20, 2021, now Pat. No. 11,375,752.

(60) Provisional application No. 63/185,458, filed on May 7, 2021.

(51) Int. Cl.

| | |
|---|---|
| ***A24F 7/00*** | (2006.01) |
| ***A24F 40/40*** | (2020.01) |
| ***A24F 40/42*** | (2020.01) |
| ***A24F 40/48*** | (2020.01) |
| ***A24F 40/485*** | (2020.01) |
| ***A61M 11/04*** | (2006.01) |
| ***A61M 15/00*** | (2006.01) |
| ***A61M 15/06*** | (2006.01) |
| *A24F 40/20* | (2020.01) |

(52) U.S. Cl.

CPC .............. *A24F 40/42* (2020.01); *A24F 40/48* (2020.01); *A24F 40/485* (2020.01); *A61M 11/042* (2014.02); *A61M 15/0021* (2014.02); *A61M 15/06* (2013.01); *A24F 40/20* (2020.01)

(56) References Cited

U.S. PATENT DOCUMENTS

| | | | | |
|---|---|---|---|---|
| 10,357,058 | B1 | 7/2019 | Contreras | |
| 10,517,334 | B1 | 12/2019 | Volodarsky et al. | |
| 10,517,338 | B2 | 12/2019 | Volodarsky et al. | |
| 11,000,067 | B1 | 5/2021 | Bajpai et al. | |
| 11,375,752 | B1 * | 7/2022 | Bajpai | A24F 40/40 |
| 11,659,865 | B2 * | 5/2023 | Bajpai | A61M 11/042 131/329 |
| 12,096,798 | B2 * | 9/2024 | Bajpai | A24F 40/46 |
| 12,137,742 | B2 * | 11/2024 | Bajpai | A24F 40/46 |
| 2009/0071481 | A1 | 3/2009 | Fishman | |
| 2013/0087160 | A1 | 4/2013 | Gherghe | |
| 2013/0319437 | A1 | 12/2013 | Liu | |
| 2014/0083441 | A1 | 3/2014 | Kaplani | |
| 2015/0122275 | A1 | 5/2015 | Wu | |
| 2015/0165137 | A1 | 6/2015 | Mullinger et al. | |
| 2016/0100628 | A1 | 4/2016 | Garcia | |
| 2016/0219937 | A1 | 8/2016 | Rado | |
| 2016/0302486 | A1 | 10/2016 | Eroch | |
| 2016/0366936 | A1 | 12/2016 | Liu | |
| 2017/0027224 | A1 | 2/2017 | Volodarsky et al. | |
| 2017/0055579 | A1 | 3/2017 | Kuna | |
| 2017/0055588 | A1 | 3/2017 | Cameron | |
| 2017/0079324 | A1 | 3/2017 | Eksouzian | |
| 2017/0202265 | A1 | 7/2017 | Hawes et al. | |
| 2017/0251718 | A1 | 9/2017 | Armoush | |
| 2017/0295845 | A1 | 10/2017 | Bajpai et al. | |
| 2018/0098569 | A1 | 4/2018 | Martin | |
| 2018/0125115 | A1 | 5/2018 | Mueller | |
| 2018/0271150 | A1 | 9/2018 | Sparklin | |
| 2019/0174825 | A1 | 6/2019 | Neuhaus | |
| 2020/0221768 | A1 | 7/2020 | Volodarsky et al. | |
| 2021/0045440 | A1 | 2/2021 | Volodarsky et al. | |
| 2022/0125102 | A1 | 4/2022 | Liu et al. | |
| 2022/0354176 | A1 * | 11/2022 | Bajpai | A61M 11/042 |
| 2023/0301356 | A1 * | 9/2023 | Bajpai | A24F 40/46 |
| 2023/0355899 | A1 * | 11/2023 | Bajpai | A24F 40/46 |
| 2024/0074501 | A1 * | 3/2024 | Bajpai | A24F 40/46 |
| 2025/0204592 | A1 * | 6/2025 | Bajpai | A61M 15/06 |
| 2025/0302102 | A1 * | 10/2025 | Bajpai | A24F 40/46 |

FOREIGN PATENT DOCUMENTS

| | | | |
|---|---|---|---|
| CN | 112120299 | A | 12/2020 |
| DE | 102016012830 | B3 | 8/2017 |

OTHER PUBLICATIONS

Puff Co., Peak Video posted on Instagram retrieved from www.instagram.com/p/Bd-oaEkFrXC/ Jan. 15, 2018.
Puff Co. Glass Attachment Video posted on Instagram retreived from www.instagram.com/p/Bd3DfMRIWLo/ Jan. 12, 2018.
Puff Co., Puffco Peak Case posted on Instagram retrieved from www.instagram.com/p/Bd027vflYzM/ Jan. 11, 2018.
Puff Co., Puffco Peak Video posted on Instagram retrieved from www.instagram.com/p/BdtMs4qIHnH/ Jan. 8, 2018.
Puff Co., Puffco Peak Hero Shot posted on Instagram retrieved from www.instagram.com/p/BdybEMAI_zX/ Jan. 10, 2018.
Pax Labs, Inc., web page of vaporizers, retrieved from www.paxvapor.com Feb. 25, 2015.
Koerber, B., This weed company just made a smart bong and it's awesome, Mashable, located at mashable.com/2018/01/08/puffco-peak-smart-bong-dab-rig-concentrates/ Jan. 8, 2018.
Tarantola, A., The Puffco Peak vaporizer is a quick hit of concentrated genius, Engadget, located at www.engadget.com/2018/03/16/puffco-peak-vaporizer-hands-on/?guccounter=1 Mar. 18, 2018.
Puff Co., Reservations are now open for Peak Atomizer Assembly, retrieved from web.archive.org/ web/20180224162936/https://www.puffco.com/ Feb. 24, 2018.
Engadget, Hands on Peak, retrieved from web.archive.org/web/20180330221034/https://www.engadget.com/2018/03/16/puffco-peak-vaporizer-hands-on/ Mar. 31, 2018.
Dr. Dabbler, Vaporizers for sale, retrieved from https://web.archive.org/web/20170222202821/https://drdabbervaporizersforsale.weebly.com/ Feb. 22, 2017.
Dr. Dabbler, Boost: Black Edition retrieved from www.drdabber.com/products/boost-black-edition 2019.
Dr. Dabbler, Boost Black Edition retrieved from www.drdabber.com/collections/all/products/boost-black-edition 2019.
Source Vapes, web page for Atomizers, retrieved from www.sourcevapes.com 2019.
Source Vapes, web page for Atomizers, retrieved from www.sourcevapes.com/collections/atomizers Feb. 16, 2016.
Vapexhale, Give the gift of relaxation, retrieved from www.xhl3.com Nov. 27, 2017.
Vapexhale, web page for starter kits, retrieved from www.xhl3.com 2019.
Cloud V Enterprises, Cloud V Bubbler Options, retrieved from cloudvapes.com/vaporizers/portable-enail/cloudv-electro-portable-dab-rig 2019.
Cloud V Enterprises, Ultra Slim Design Vaporizers, retrieved from cloudvapes.com/store/ Jan. 21, 2013.
Cloud V Enterprises, Cloud V, retrieved from cloudvapes.com/store/ Feb. 22, 2016.
Dabado Vaporizers, web page for Dabado Bolt, retrieved from dabadovaporizers.com/collections/bolts 2019.
Dabado Vaporizers, web page for Dabado Bolt, retrieved from dabadovaporizers.com Jan. 1, 2016.
Kevin H., Focusvape Tourist Review—The Accidental Tourist, retrieved from vapesterdam.com/review/focusvape-tourist-review/ 2019.
Focus Vape, web page of vaporizers, retrieved from focusvape.eu/shop/ Jul. 17, 2017.
Pax Labs, Inc., Pax 3, retrieved from paxvapor.com 2019.
Waxxim, Vape Pen Bubblers shopping page, retrieved from www.waxxim.com 2019.
Puff Co., Introducing the Peak, retrieved from vimeo.com/257080728 Feb. 28, 2018.
Patent Cooperation Treaty, International Search Report for PCT/US2019/013501, 6 pages Oct. 10, 2019.
Polar Bottle, Sport Cap, retrieved from polarbottle.com/product/bottles/free-replacement-cap/sport/ on Nov. 1, 2019.

(56) References Cited

OTHER PUBLICATIONS

Lock & Lock, Lock & Lock, No BPA, Water Tight, Food Container, 2.5-cup, 20-oz, HPL933, retrieved from www.amazon.com/Water-Tight-Container-2-5-cup-HPL933/dp/B005BRGWZE on Nov. 1, 2019 Oct. 2014.
Smokea, Piecemaker Kahuna 2 in. Silicone Bong, retrieved from https://smokea.com/products/piecemaker-kahuna-2-silicone-bong?variant=37965420929 on Nov. 1, 2019 Jun. 2018.
Osprey, Hydraulics Bite Valve, retrieved from https://www.osprey.com/US/en/product/hydraulics-bite-valve-NONMAGVALV.html on Nov. 1, 2019 Apr. 2013.
Bray, Flowtek Triad Series, retrieved from www.bray.com/ball-valves/3-piece-valves/triad-series on Nov. 1, 2019 Mar. 2017.
Grenco Science, Gpen Connect Collection, retrieved from web.archive.org/web/20191001142752/https:// www.gpen.com/collections/g-pen-connect Oct. 1, 2019.
Dr. Dabbler, Boost: Black Edition Support retrieved from web.archive.org/web/20210127091740/https://www.drdabber.com/pages/boost-black-support Jan. 27, 2021.
VapeYaya, e-pipe, retrieved from web.archive.org/web/20210509224114/https://www.vapeyaya.com/index.php? route _=Premium-E-cig-E-Pipe May 9, 2021.
Pulsar Vaporizers, Pulsar Petite Pocket Carting Rig Bubbler, retrieved web.archive.org/web/20210331144200/https://www.pulsarvaporizers.com/products/pulsar-petite-pocket-cart-rig-bubbler-5 from Mar. 31, 2021.
Lookah, Lookah Q7 Mini Enail Banger Fits onto Water Pipes and Dab Rigs, retrieved from web.archive.org/web/20210124114528/https://www.lookah.com/vaporizers/dab-vaporizer/lookah-q7-water-pipe-compatible-concentrate-vaporizer.html Jan. 24, 2021.
ePuffer, Inc., ePuffer ePipe, retrieved from epuffer.com/news-and-press/epuffer-epipe-629x-flat-led-cap/ Apr. 4, 2020.
Best Vape Pipes and E-Cigars retrieved from https://ecigarettereviewed.com/vap-pipes-e-cigars/ Jul. 7, 2022.
YouTube -Divine Tribe V5 portable vaporizer prototype heater 2nd batch, some sessions and a self cleaning,dated 15, 2021 retreived from https://www.youtube.com/watch?v=2XGj2sSS_88.
Adams, "Puffco Unveils 3D Chamber for Maximum Experience on Peak Pro," High Times Oct. 28, 2021.
Divine Tribe—Replacement Side and Bottom Heated Ceramic Cup Sets for the v5 and Core 2.0 Coils, retreived from https://ineedhemp.com/product/replacement-side-and-bottom-v5-heater-cups-ceramic-spacers/ Aug. 24, 2022.
Facebook Watch—3D Chamber Drops Now, Puffco Oct. 27, 2021 retrieved from https://m.facebook.com/ChoosePuffco/videos/the-wait-is-over-the-3d-chamber-drops-now-it-improves-on-every-aspect-of-peak-pr/1099085837508804/?_ se_imp=0UokVxVNhe8D4XCbV.
PCT International Search Report and Written Opinion for PCT/US2022/028114 dated Aug. 16, 2022.
PCT International Search Report and Written Opinion for PCT/US2022/028122 dated Aug. 16, 2022.
YouTube video—Davinci IQ Herbal Vaporizer Review retrieved from https://www.youtube.com/watch?v=Hz8w6IYzUGo Jul. 20, 2019.
YouTube video—PAX 3 Vaporizer Matte Finish—Unboxing & Review retrieved from https://www.youtube.com/watch?v=UKrzbdNqCqo on Mar. 21, 2018.
YouTube video—G Pen Pro Unboxing & Review retrieved from https://www.youtube.com/watch?v=rxFSUfEiM-A on 6, 2018.
Mr. Brog Full Bent Smoking Tobacco Pipe retrieved from https://www.ubuy.co.in/product/2E6DOHS-mr-brog-full-bent-smoking-tobacco-pipe-model-No. 21-old-army-mahogany-pear-wood-roots-like-briar-hand on Nov. 14, 2022.
VapeYaya, e-pipe, retrieved from web.archive.org/web/20210509224114/https://www.vapeyaya.com/index.php? foute _=Premium-E-cig-E-Pipe May 9, 2021.
Examination Report for EP Application No. 22725670.8, issued on Feb. 4, 2026.

* cited by examiner

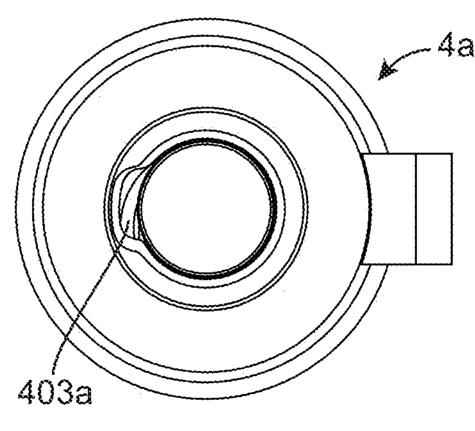
FIG. 11A
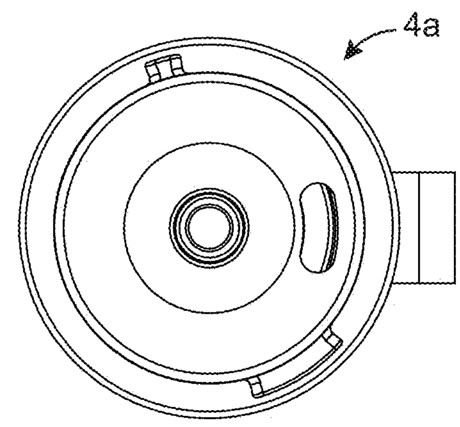
FIG. 11B
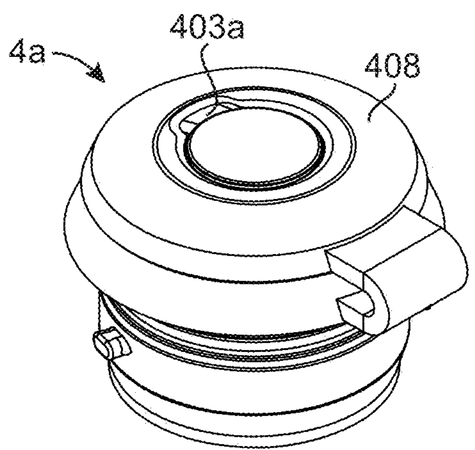
FIG. 11C
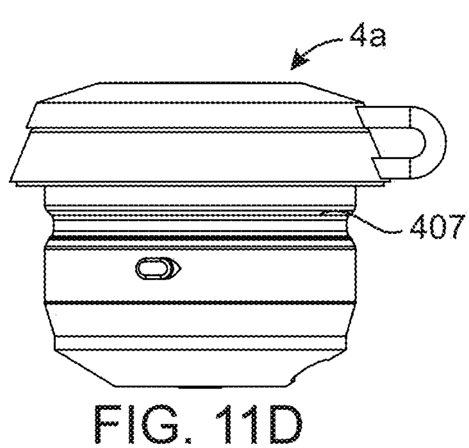
FIG. 11D
4a
407
FIG. 11E

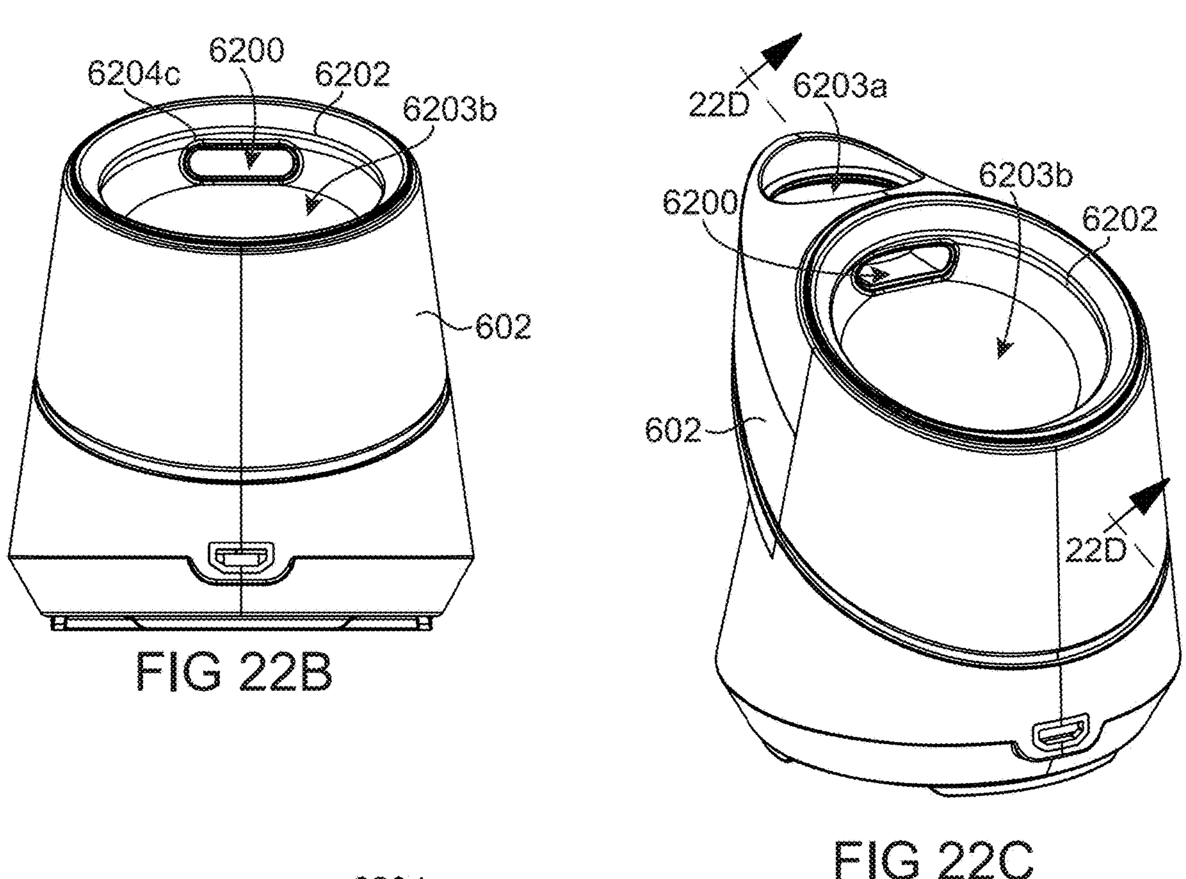
FIG 22B
FIG 22C
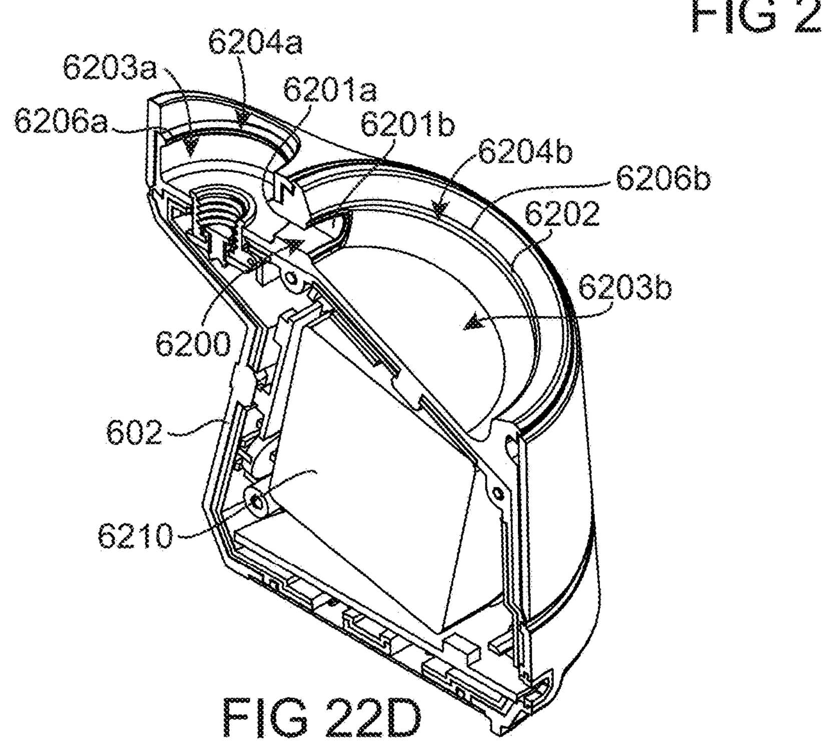
FIG 22D

PORTABLE VAPORIZATION MODULE, DEVICE, CONTAINER, AND METHODS

CROSS REFERENCE TO RELATED APPLICATIONS

The present application is a continuation of U.S. patent application Ser. No. 18/941,891, filed on Nov. 8, 2024, which is a continuation of U.S. patent application Ser. No. 18/136,684, filed on Apr. 19, 2023, now U.S. Pat. No. 12,137,742, which is a continuation of U.S. patent application Ser. No. 17/861,131, filed on Jul. 8, 2022, now U.S. Pat. No. 11,659,865, which is a continuation of PCT international application no. PCT/US2022/028122, filed on May 6, 2022, which claims benefit of U.S. Provisional Patent Application Ser. No. 63/185,458, filed on May 7, 2021, and U.S. patent application Ser. No. 17/407,446, filed on Aug. 20, 2021, now U.S. Pat. No. 11,375,752. The entire contents of the aforementioned applications are hereby incorporated by reference as if recited in full herein.

FIELD OF THE INVENTION

Aspects of the present invention relate to portable electronic vaporizing devices for use with vaporizable products.

BACKGROUND

Electronic vaporizers are commonplace and are generally utilized for the purpose of aroma and/or inhalation therapy. In this regard, vaporizers heat a substance, herbs for example, such as tobacco, cannabis, lavender, chamomile, and many other types of plant material. The vaporizer may work by heating the substance through the use of direct heat or the use of hot air. There are three common ways of heating the substance. The first is thermal conduction where the substance is set directly on a heating element such as a ceramic or metal plate. The second is thermal radiation in which light is used to heat the substance. The third is convection where hot air is passed over the substance. Yet another suitable mechanism for vaporizing a substance may be via inductive heating.

At lower levels of heat, vapors extracted from substances such as vegetable materials are mainly aroma therapeutic (inactive fragrance) and do not usually contain the active ingredients of the substance. Without the active ingredients being present, there is no physiological reaction. At higher levels of heat, active ingredients will be increasingly included in the vapor given off during heating. Usually, aromatic vapors have already been released and are not always present at the higher heat levels. With some substances, such as cannabis, active ingredients appear at different levels of heat.

After the substance is heated a mist or vapor containing some aspect of the substance is released and either enjoyed as an aromatic or inhaled to obtain a physiological reaction. The warm air containing the substance product can be harsh on the throat and bronchial tubes. Accordingly, some vaporizers use a cooling down process that allows water moisture to be included in the vapor produced. These vaporizers enable the user to inhale a cool moist vapor that is relatively less harsh and irritating. Vaporizers are often preferred over traditional methods of heating or smoking substances due to the reduction of harsh side effects. Some of these side effects include inhalation of tar, carbon monoxide, and other carcinogens either directly or from second hand smoke. With many states imposing smoking bans in public areas, vaporizers have become popular substitutes.

Accordingly, there is a need for improved vaporizers that provide an enhanced vaporizing experience, including vaporizers with improved quality of the vapor produced for inhalation and improved ease of use.

SUMMARY

Aspects of the invention are directed to a portable electronic vaporizing device comprising a removably attachable vaporization module, and a mouthpiece configured to receive a flow of gas having vaporized product entrained therein from the removably attachable vaporization module. The mouthpiece comprises: a mouthpiece housing at least partly defining an interior chamber, an inhalation outlet formed in the mouthpiece housing, and a receiving area for receiving the removably attachable vaporization module that is battery-powered in the interior chamber of the mouthpiece housing. The removably attachable vaporization module comprises: a base portion and a vaporization assembly. The base portion comprises: a module housing having an insert portion configured to be at least partly received within the receiving area of the mouthpiece housing, the insert portion having one or more sealing regions configured to form a seal between the module housing and the mouthpiece housing, and a battery receiving area disposed within the insert portion and configured to receive a battery for powering the removably attachable vaporization module, and a gas flow conduit having an input opening and an output opening positioned to output the flow of gas from the removably attachable vaporization module to the receiving area of the mouthpiece at an interior side of the seal between the module housing and the mouthpiece housing. The vaporization assembly comprises: a vaporization assembly housing, a refillable container configured to receive a vaporizable product within the vaporization assembly housing, a heating device configured to be electrically connected to the battery and transfer energy to the vaporizable product in the refillable container to heat the product and form a vapor product therefrom, an inlet configured to introduce gas into the refillable container, one or more refillable container outlets configured to receive the flow of gas having vaporized product entrained therein from the refillable container, and one or more vaporization assembly outlets configured to provide the flow of gas received from the refillable container outlets to the input opening of the gas flow conduit in the base portion. In operation of the portable electronic vaporizing device, the flow of gas having the vaporized product entrained therein is passed through the gas flow conduit and received into the receiving area of the mouthpiece from the output opening of the gas flow conduit, and is passed along the interior chamber of the mouthpiece to the inhalation outlet.

According to another aspect of the invention, a method of using the portable electronic vaporizing device disclosed herein is provided. The method comprises: inserting the removably attachable vaporization module into the receiving area of the mouthpiece; providing vaporizable product to the product receiving chamber of the removably attachable vaporization module; activating the heating device to heat the vaporizable product in the product receiving chamber to at least partly vaporize the product; and inhaling gas entrained with the vaporizable product from the inhalation outlet of the mouthpiece.

According to yet another aspect of the invention, a removably attachable base portion of a removably attachable vaporization module is provided for vaporizing a vaporizable product in a portable vaporizing device having a receiving body to receive the removably attachable base portion in a receiving region thereof. The removably attachable base portion comprises: a housing having an insert portion configured to be at least partly received within the receiving area of the receiving body, the insert portion having one or more sealing regions configured to form a seal between the housing and one or more walls of the receiving body, and a battery receiving area disposed within the insert portion and configured to receive a battery for powering the removably attachable vaporization module; and a gas flow conduit having an output opening positioned to output the flow of gas from the removably attachable base portion to the receiving area of the receiving body at an interior side of the seal between the housing and the one or more walls of the receiving body.

According to another aspect of the invention, a container used to hold vaporizable product in a portable electronic vaporizing device is provided. The container comprises: container walls comprising one or more sidewalls and a bottom wall that form a space to receive the vaporizable product, and a heating device comprising one or more resistive heating elements embedded in one or more of the container walls, the heating device configured to be electrically connected to a battery and transfer energy to the vaporizable product in the container to heat the product and form a vapor therefrom, wherein the bottom wall and lower regions of the one or more sidewalls form a continuous barrier to the passage of gas and/or liquid into or out of the container.

According to still another aspect of the invention, a portable vaporizing device comprising the refillable container disclosed herein and methods of using such container and device are provided. The method comprises: providing vaporizable product to the refillable container; activating the heating device to heat the vaporizable product in the refillable container to at least partly vaporize the product; and inhaling gas entrained with the vaporized product via the portable vaporizing device.

According to a further aspect of the invention, a vaporization assembly and an atomizer comprising the refillable container disclosed herein are also provided.

According to yet another aspect of the invention, removably attachable vaporization module that is battery-powered is provided that is configured to attach to and form an air tight seal with a mouthpiece. The mouthpiece comprises a mouthpiece housing at least partly defining an interior chamber, and an inhalation outlet in communication with the interior chamber. The removably attachable vaporization module that is battery-powered comprises: a vaporization assembly configured to heat a vaporizable product to form a vaporized product therefrom; a base portion comprising a battery storage compartment configured to store a battery to power removably attachable vaporization module that is battery-powered, the base portion being configured such that the battery storage compartment is received within the interior chamber of the mouthpiece housing when removably attachable vaporization module that is battery-powered is attached to the mouthpiece; and wherein, during use of removably attachable vaporization module that is battery-powered, gas entrained with vaporized product flows from the vaporization assembly to the interior chamber of the mouthpiece and exits the mouthpiece via the inhalation outlet.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 11A-11E show various views of another embodiment of a vaporization assembly;

FIGS. 22A-22C show various perspectives of an embodiment of a base, FIG. 22D is a cross-sectional view of FIG. 22C.

DETAILED DESCRIPTION OF THE INVENTION

Aspects of the invention as described herein are directed to an improved portable electronic vaporizing device for the inhalation of vaporizable substances, such as aromatic substances, therapeutic substances and/or substances with physiological effects. Examples of such substances can include herbs, such as tobacco, cannabis, lavender, chamomile, and other types of plant material. In one embodiment, a vaporizable substance can comprise a cannabinoid, such as for example one or more of cannabadiol (a generally non-psychoactive therapeutic substance) and tetrahydrocannabinol (THC) (a psychoactive therapeutic substance). The vaporizable substance may in some embodiments be in the form of an oil and/or wax product comprising the vaporizable substance, e.g., as extracted from plant material containing the substance, and may optionally be provided in combination with carriers or other additives.

Figure 1:
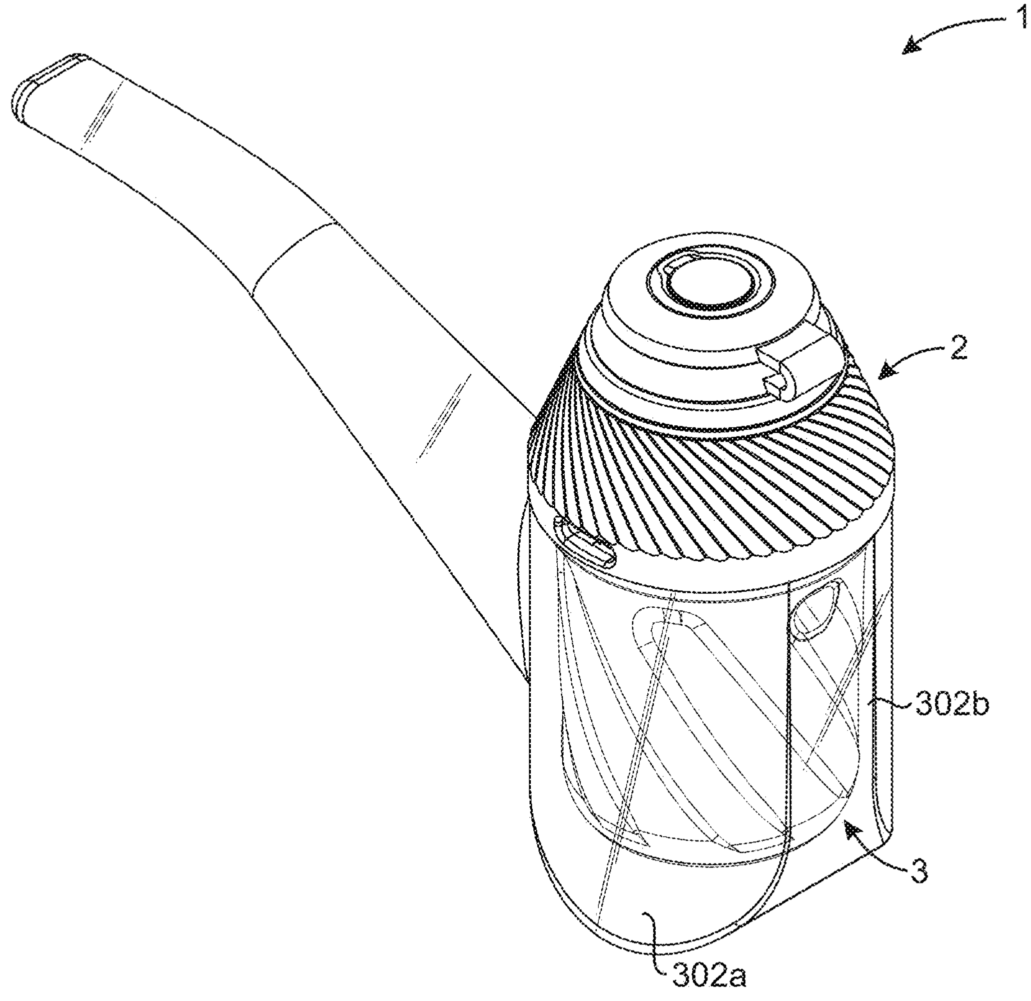
FIG. 1 shows an embodiment of a portable electronic vaporizing device comprising a removably attachable vaporization module and a mouthpiece.

Referring to FIG. 1, an embodiment of a portable electronic vaporizing device 1 is shown according to aspects of the disclosure herein. The portable electronic vaporizing device 1 comprises a removably attachable vaporization module 2 and a mouthpiece 3. The removably attachable vaporization module 2 is configured to receive a vaporizable product therein and to heat the vaporizable product to form a vapor therefrom. The mouthpiece 3 comprises an inhalation outlet 305 (depicted in FIG. 9B) where a user can inhale the vapor produced by the removably attachable vaporization module 2, optionally with water or other substances entrained therein. The mouthpiece 3 can be provided in various forms including but not limited to a pipe, or forms, and optionally with water filtration.

Figure 2:
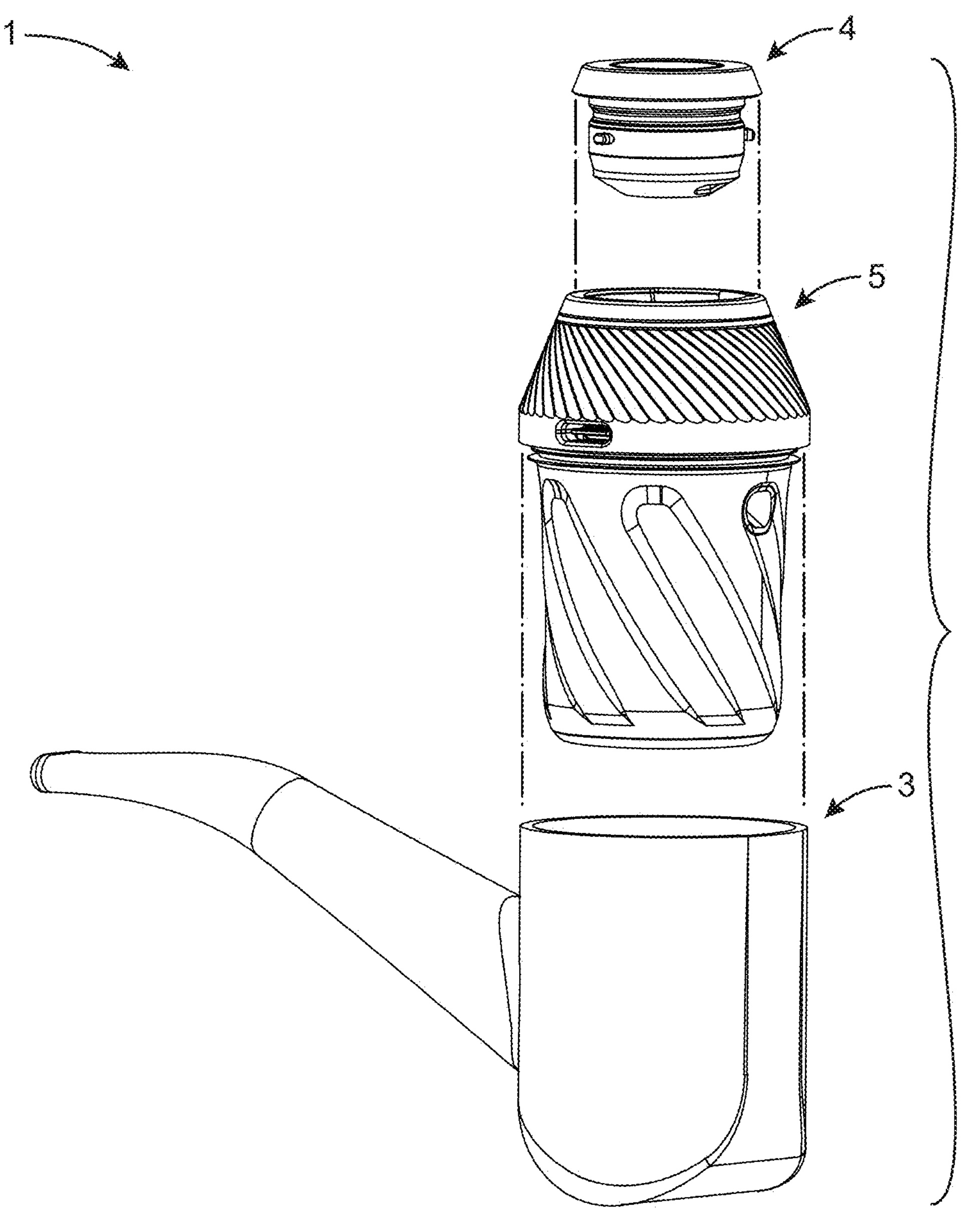
FIG. 2 is an exploded side view of an embodiment of the device.

Referring to FIG. 2, an embodiment of the portable electronic vaporizing device 1 is shown in exploded view, with the removably attachable vaporization module 2 removed from the mouthpiece 3. The removably attachable vaporization module 2 further comprises (and in FIG. 2 is shown as separated into) a vaporization assembly 4 and a base portion 5. The base portion 5 provides a gas flow connection between the vaporization assembly 4 and mouthpiece 3, to deliver the vaporized product from the vaporization assembly 4 to the mouthpiece 3 for delivery to the user via inhalation thereof. The base portion 5 can also comprise a housing for one or more components for powering and/or controlling the portable electronic vaporizing device 1. For example, the base may contain compartments therein for storing a power source, such as a battery, for powering elements of the portable electronic vaporizing device 1 such as a heating element or other heating device used in the vaporization assembly 4. In a case where the device is powered by a rechargeable battery, such as a lithium ion battery, the base portion 5 may also comprise a charging port connectable to a battery charger (not shown). The base may also have compartment doors to allow access to a battery or other components held within the housing. The base portion 5 may also house further control circuitry for controlling the device, such as to provide predetermined heating cycles or heating programs, and may also allow for user interaction with the device via control buttons and/or control interface, a display and/or lights to signal to the user, and/or other control and operation features.

Figure 3A:
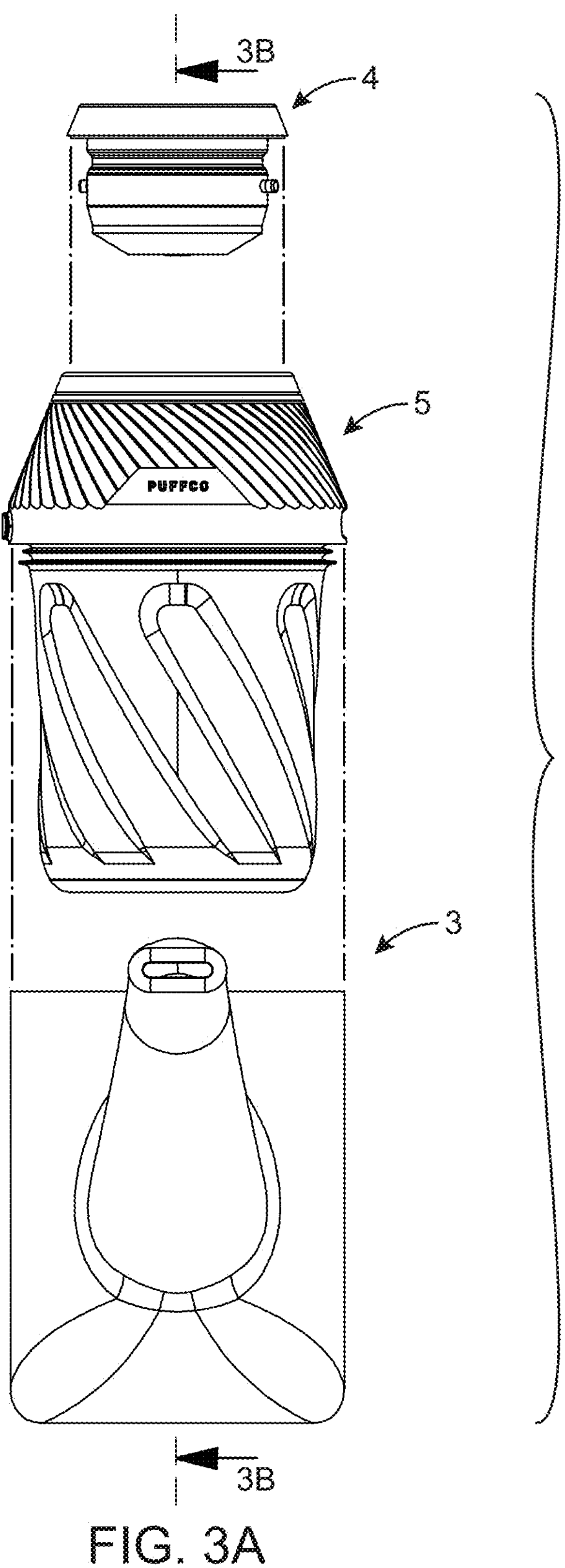
FIG. 3A is an exploded front view of the device of FIG. 2.

In one embodiment, the mouthpiece 3 is removably attachable to the base portion 5, for example so as to allow a user to readily remove the mouthpiece for cleaning and/or replacement, as is described in further detail herein. For example, according to one embodiment, the base portion 5 and mouthpiece can be removed from one another by exerting a force on the base portion 5 that exceeds a retaining force of sealing regions (described below) that form a seal between portions of the base portion and the mouthpiece), to lift the base portion 5 out of the mouthpiece 3. The base portion 5 can be re-attached to the mouthpiece by inserting the insert portion (described below) into the receiving area of the mouthpiece and engaging the sealing regions to retain the base portion 5 as inserted within the mouthpiece. Other mechanisms for removably attaching the base portion 5 to the mouthpiece can also be provided. In yet another embodiment, the vaporization assembly 4 may be removably attachable to the base portion 5, for example so as to allow a user to replace the vaporization assembly 4 when no longer serviceable, for cleaning of the vaporization assembly 4, and/or to more readily allow access to a container (e.g. bowl) where a vaporizable product may be loaded into the vaporization assembly 4. For example, the vaporization assembly may be received in a vaporization assembly receiving area 506 (depicted in FIG. 7B) of the base portion 5, and can be attached to the base portion 5 by twisting to engage a chamber bayonet 514 that secures the vaporization assembly 4 in the receiving area 506. The vaporization assembly 4 can be removed by untwisting to release from the chamber bayonet. Other mechanisms for removably attaching the vaporization assembly 4 to the base portion 5 can also be provided. In one embodiment, both the vaporization assembly 4 and the mouthpiece 3 may be removably attachable to the base portion 5. In yet another version, the vaporization assembly 4 may be independently removable from the base portion 5. That is, the vaporization assembly 4 may be configured to be removably attached to the base portion 5 such that it can be removed therefrom, without requiring that the mouthpiece 3 and/or base portion 5 be removed from one another beforehand. A cross-sectional view of the portable electronic vaporizing device 1 in exploded view can be found in FIG. 3B (FIG. 3A shows a front exploded view).

Figure 5A:
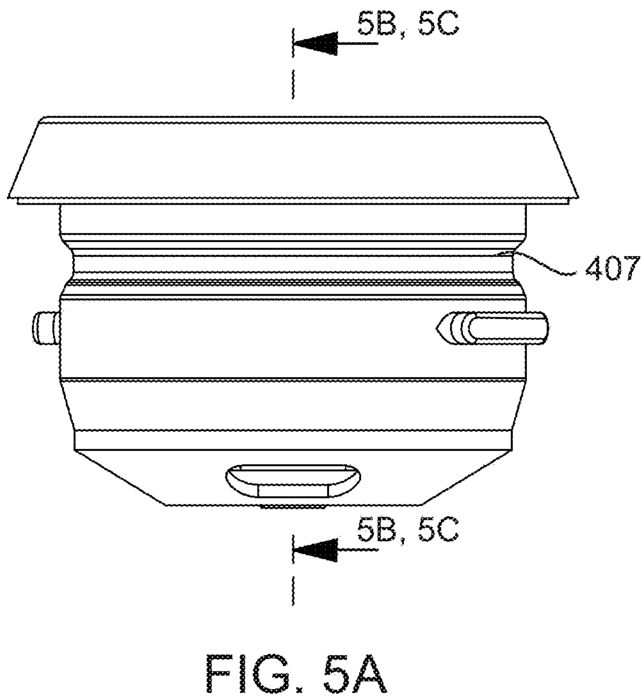
FIG. 5A is a perspective view of the vaporization assembly of FIGS. 4A-4E.
Figure 5B:
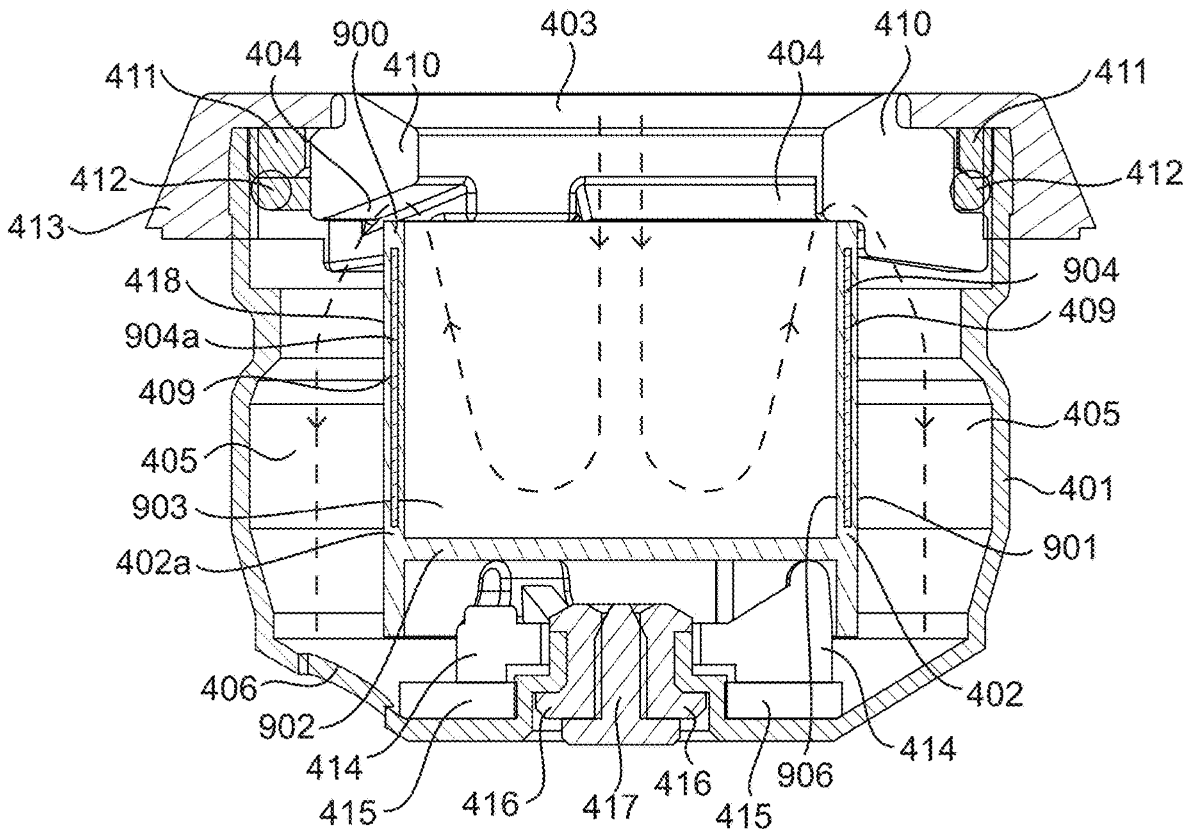
FIG. 5B is a cross-sectional view of FIG. 5A.

Referring to FIGS. 4A-4E, an embodiment of the vaporization assembly 4 is shown. Front and cross-sectional views of the structure of the vaporization assembly 4 and a gas flow path therethrough are shown in more details in FIGS. 5A-5B. According to one aspect of this disclosure, the vaporization assembly 4 as shown in FIGS. 4A-4E and 5A-5B is suitable for inhaling a vaporizable substance in the form of an oil and/or wax product comprising the vaporizable substance, e.g., as extracted or otherwise obtained from plant material containing the substance, and may optionally be provided in combination with carriers or other additives. Accordingly, the vaporization assembly 4 comprises a vaporization assembly housing 401, a refillable container 402 configured to receive a vaporizable product within the vaporization assembly housing 401, a heating device 409 configured to be electrically connected to a power source such as a battery and transfer energy to the vaporizable product in the refillable container 402 to heat the product and form a vapor therefrom, an inlet 403 configured to introduce gas into the refillable container 402, one or more refillable container outlets 404 configured to receive a flow of gas having vaporized product entrained therein from the refillable container 402, and one or more vaporization assembly outlets 406 configured to provide the flow of gas received from the refillable container outlets 404 to the input opening 510 of the gas flow conduit 505 in the base portion 5. In one embodiment, the refillable container 402 itself comprises the heating device, such that the refillable container 402 can be directly heated to transfer energy to the vaporizable product therein, and thus no separate heating device is required. For example, sidewalls 418 of the refillable container 402 can comprise a resistive heating element 904 (heater traces 904*a*, as shown in FIG. 5B via dotted lines) embedded therein, e.g., by wrapping the resistive heating element 904 with soft ceramic material and forming a tube shape, adhering a thin ceramic bottom (without traces) to the tube, then firing the soft ceramic with resistive heating element 904 embedded therein to obtain the refillable container 402. In another embodiment, the bottom of the refillable container 402 may also comprise heating element (heater traces) embedded therein. In one embodiment, the resistive heating element (e.g., heater traces) is only embedded in the sidewalls of the refillable container.

In one embodiment, the heating device 409 (heating element or heater trace) is attached to conductive elements such as wires leading to the power source (e.g. battery) in the base portion 5 to provide an applied voltage for the resistive heating. For example, in operation, two wires come from the bottom of the vaporization assembly 4: one of the wires can be held (pressed) between the electrode 417 and the insulator 416, being connected to the heating device 409 embedded in the sidewalls 418, and the other wire can be held between the insulator 416 and the vaporization assembly housing 401, traveling up the housing wall and being spot welded to the vaporization assembly housing 401. To apply the voltage, the base electrodes 517 contact the vaporization assembly housing 401 and the electrode 417, therefore a current path in and out of the heating device 409 can be created. There can be also grooves cut into the inner surface of the vaporization assembly housing to position these wires.

In yet another embodiment, the heating device 409 is provided separately and/or apart from the container in any suitable form such as a heating plate or coil (not shown), and which can be placed in thermal contact with the refillable container 402 at any desirable position/angle such as being disposed below the bottom of the container. For example, the heating device may comprise at least one of a heating plate, a heating ring, and a heating element, and is capable of conductively heating the vaporizable product in the refillable container. As another example, the heating device may comprise an inductively heating device capable of inductively heating the container, and/or may be capable of radiatively heating the container and/or product provided within the container. In one embodiment, the heating element comprises a ceramic heating plate, such as an alumina plate, and may also comprise, e.g. a metal wire, coil, or other element that is capable of resistively heating, and which may also be embedded in a ceramic or glass heating plate or used alone. Additional embodiments of heating elements, heating plates and any other heating structures that can be used to form all or a part of the heating device 409 have been described in U.S. Pat. No. 10,517,334, which is hereby incorporated by reference herein in its entirety.

In yet another embodiment, the inlet 403 and the one or more refillable container outlets 404 of the vaporization assembly 4 are located towards a top of the refillable container 402 and the one or more refillable container outlets 404 of the vaporization assembly 4 are located radially external to the inlet 403 of the refillable container 402.

In one embodiment, the internal gas flow passage 405 is defined between the vaporization assembly housing 401 and walls of the refillable container 402, radially external to the refillable container 402, and the internal gas flow passage 405 redirects the flow of gas received from the one or more refillable container outlets 404 in a direction towards the base portion 5 of the battery-powered removably attachable vaporization module 2. As shown in FIG. 5B, the dashed lines illustrate an exemplary gas flow path within the vaporization assembly 4. A flow of ambient air enters the vaporization assembly 4 through the inlet 403, carries the vapor formed by the heated vaporable product in the refillable container 402, then passes through one or more refillable container outlets 404 located near the top edge of the refillable container 402 and enters into the internal gas flow passage 405, and eventually leaves the vaporization assembly 4 through one or more vaporization assembly outlets 406. In one embodiment, the one or more vaporization assembly outlets 406 is located at a lower region (e.g., the bottom) of the vaporization assembly housing 401. In yet another embodiment, at least one of the one or more vaporization assembly outlets 406 is aligned with the input opening 510 of the gas flow conduit 505 in the base portion 5.

According to embodiments herein, as shown in FIG. 5B, the vaporization assembly 4 can comprise a thermal spacer 410, a securing ring 411, an O-ring 412, a jacket 413, a container spacer 414, a washer 415, an insulator 416 and an electrode 417 to conduct electricity to the heating device 409.

Figures 6A, 6B, 6C, 6D, 6E:
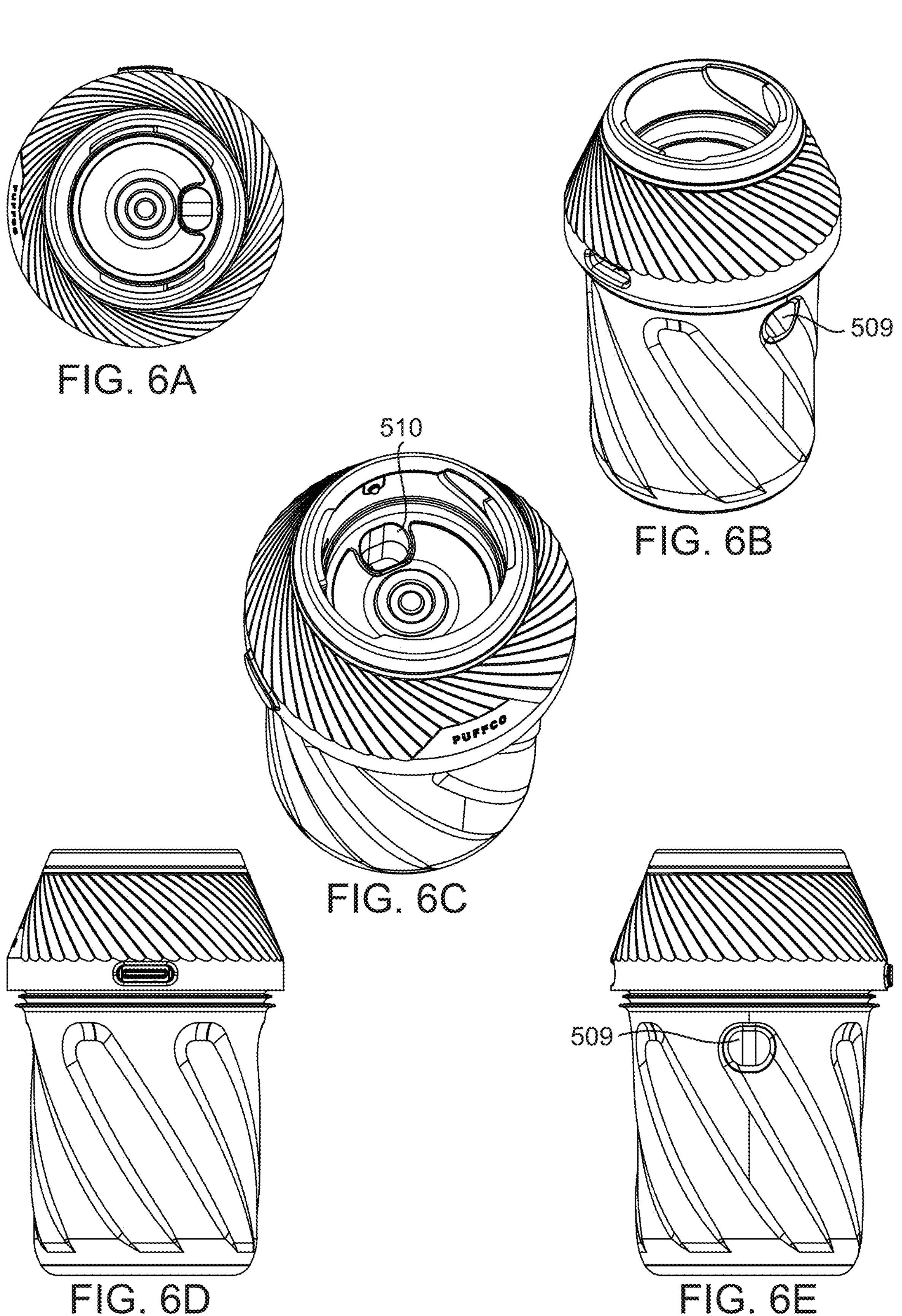
FIGS. 6A-6E show various views of an embodiment of a base.
Figure 7A:
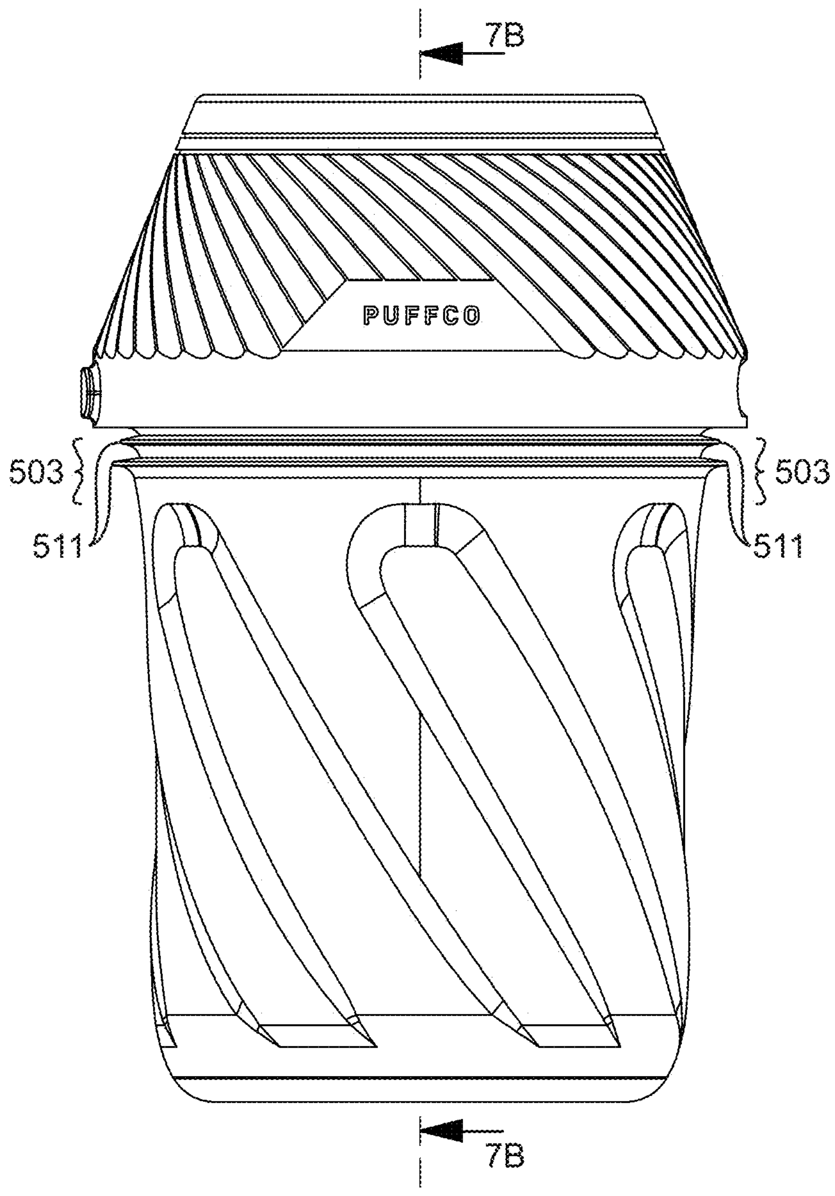
FIG. 7A is a perspective view of the base portion of FIGS. 6A-6E.
Figure 7B:
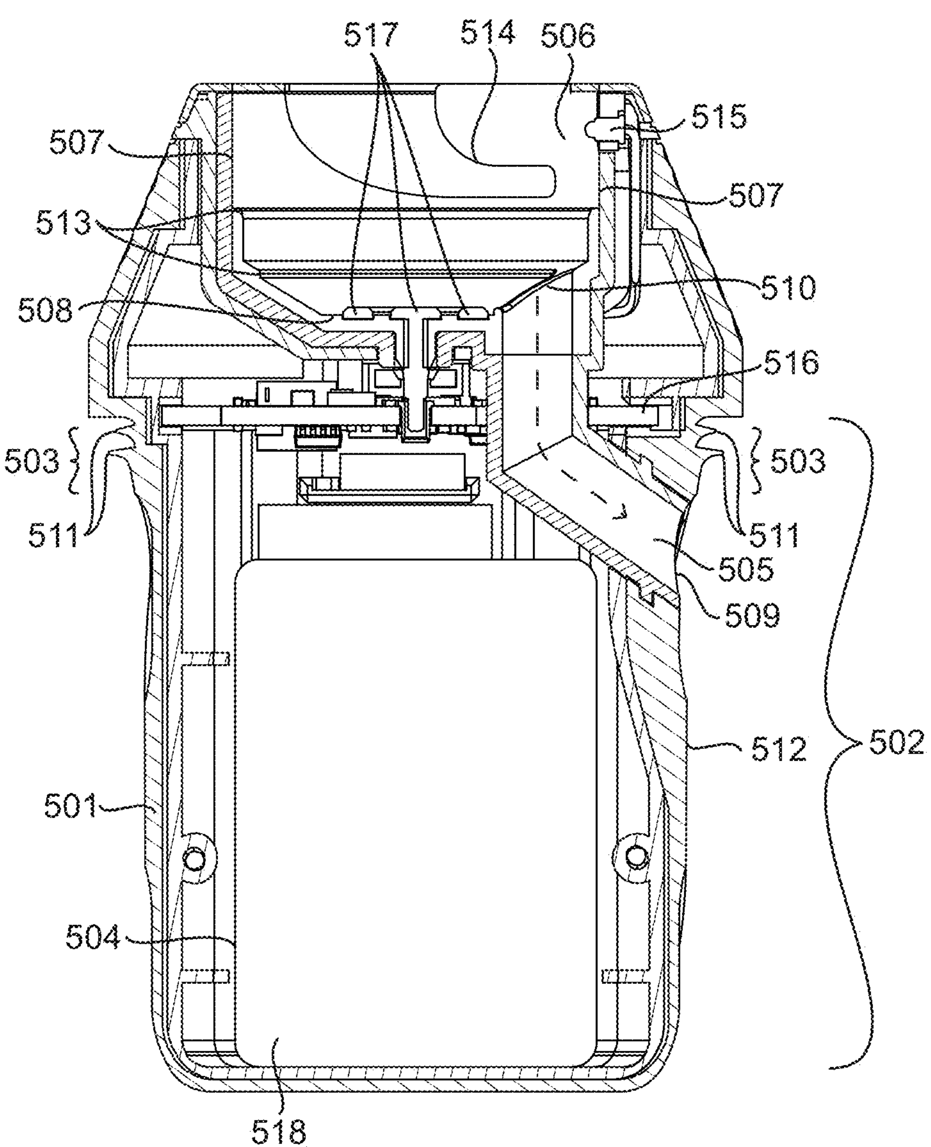
FIG. 7B is a cross-sectional view of FIG. 7A.
Figures 8A, 8B, 8C, 8D, 8E:
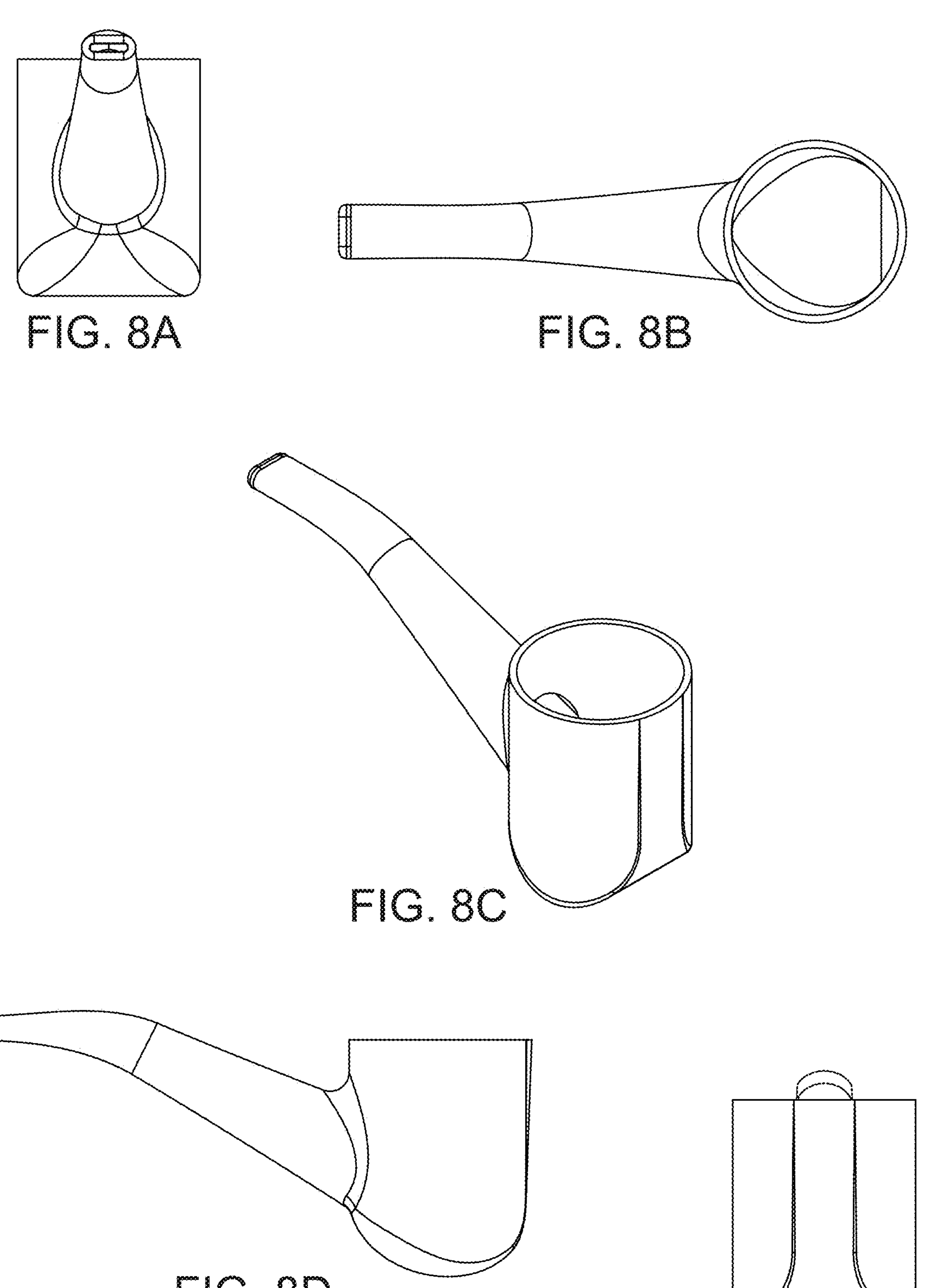
FIGS. 8A-8E show various views of an embodiment of a mouthpiece.
Figure 9A:
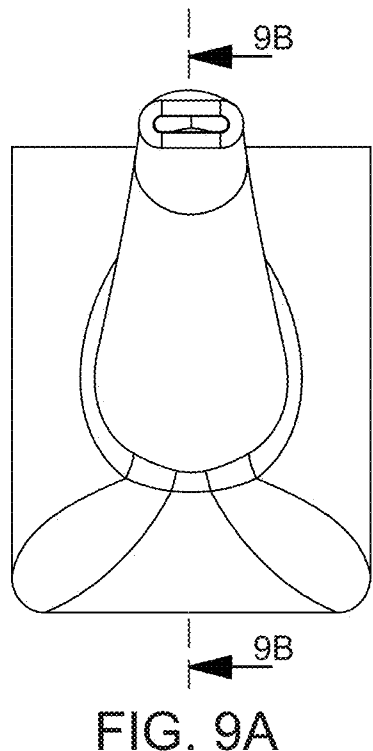
FIG. 9A is a perspective view of the mouthpiece of FIGS. 8A-8E.
Figure 9B:
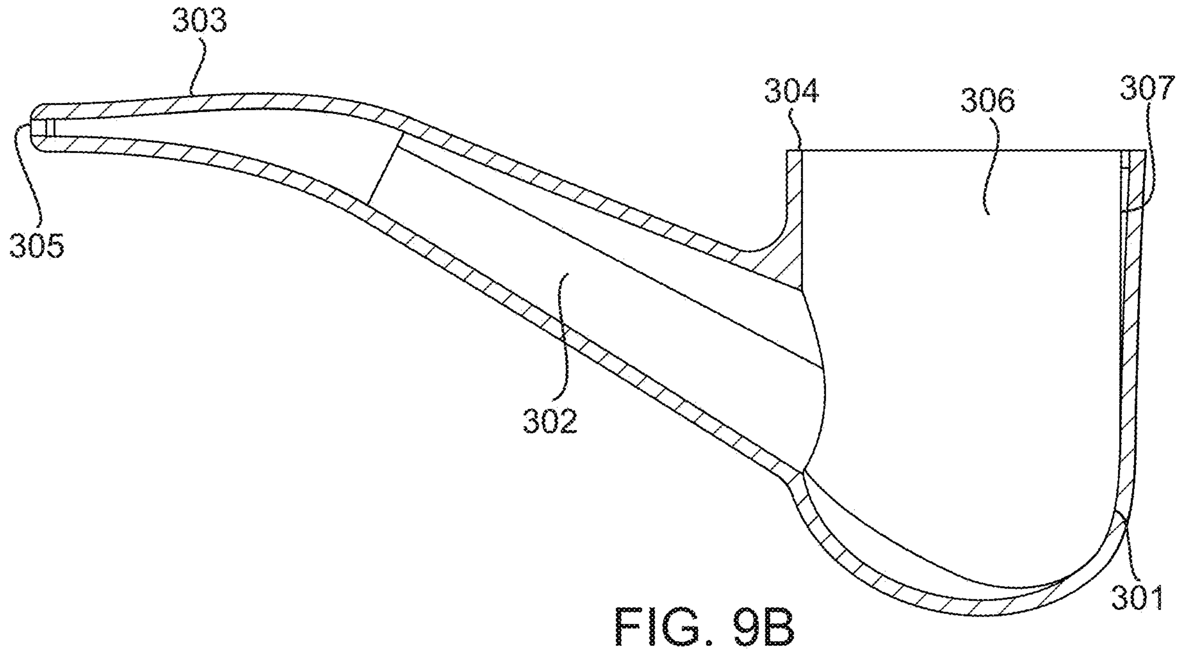
FIG. 9B is a cross-sectional view of FIG. 9A.

Referring to FIGS. 6A-6E, an embodiment of the base portion 5 is shown. A cross-sectional view of the structure of the vaporization assembly 4 and base portion 5 with the gas flow path therethrough is shown in more detail in FIG. 7B. The base portion 5 comprises base sidewalls 507 and a bottom wall 508 defining a vaporization assembly receiving area 506 configured to receive the vaporization assembly 4 therein. As shown in FIG. 7B, the base portion 5 may also comprises a chamber air seal 513, a chamber bayonet 514, a chamber detection pogo pin 515, a printed circuit board assembly (PCBA) 516, a base electrode 517, and optionally a battery 518. In one embodiment, the base portion 5 comprises a module housing 501 having an insert portion 502 configured to be at least partly received within the receiving area 306 of the mouthpiece housing 301 (as shown in FIG. 9B), the insert portion 502 having one or more sealing regions 503 configured to form a seal between the module housing 501 and the mouthpiece housing 301, and a battery receiving area 504 disposed within the insert portion 502 and configured to receive a battery 518 for powering the removably attachable vaporization module 2. Embodiments of the base portion 5 comprise a gas flow conduit 505 having an output opening 509 positioned to output the flow of gas from the removably attachable vaporization module 2 to the receiving area 306 of the mouthpiece 3 at an interior side of the sealing region 503 between the module housing 501 and the mouthpiece housing 301. In one embodiment, the gas flow conduit 505 has an input opening 510 formed in the bottom wall 508 of the vaporization assembly receiving area 506 of the base portion 5, and is configured to be directly engaged to and/or aligned with at least one of the one or more vaporization assembly outlets 406 of the vaporization assembly 4 (not shown). An embodiment of the gas flow path is depicted via dashed lines in FIG. 7B. In yet another embodiment, the gas flow conduit 505 extends from the input opening 510 formed in the bottom wall 508 of the vaporization assembly receiving area 506 to the output opening 509, and as shown in FIGS. 6B and 6C, the output opening 509 of the gas flow conduit 505 is formed on an outer surface 512 of the insert portion 502 of the module housing 501 and is radially external to the input opening 510.

Referring to FIGS. 8A-8E, different views of an embodiment of the mouthpiece 3 is shown. A front view and a cross-sectional view are further provided in FIGS. 9A-9B. According to one embodiment, the mouthpiece 3 comprises a mouthpiece housing 301 at least partly defining an interior chamber 302 having a first end 303 and a second end 304, an inhalation outlet 305 formed in the mouthpiece housing 301 at the first end 303 of the interior chamber 302, and a receiving area 306 for receiving the removably attachable vaporization module 2 that is battery-powered at the second end 304 of the interior chamber 302 within the mouthpiece housing 301. According to embodiments herein, in operation of the portable electronic vaporizing device 1, the flow of gas having the vaporized product entrained therein is passed through the gas flow conduit 505 of the base portion 5 and received into the receiving area 306 of the mouthpiece 3 from the output opening 509 of the gas flow conduit 505, and is passed along the interior chamber 302 of the mouthpiece 3 to the inhalation outlet 305. While the mouthpiece 3 depicted herein is in the shape of a pipe, it should be understood that other mouthpiece shapes and forms are also contemplated herein.

In one embodiment, the battery receiving area 504 of the insert portion 502 is configured to be entirely received within the receiving area 306 of the mouthpiece 3, such that a battery 518 received in the battery receiving area 504 is enclosed by the walls of the mouthpiece 3. In another embodiment, at least a portion of the vaporization assembly 4 connects to the base portion 5 at an exterior side of the seal formed between the module housing 501 and the mouthpiece housing 301. For example, the vaporization assembly 4 may be attached to the base portion 5 at a location that is positioned above the sealing regions 503 that seal the base portion of the removably attachable vaporization module 2 to the mouthpiece, such that the vaporization assembly is located above the mouthpiece. In yet another embodiment, at least a portion of the battery receiving area 504 of the removably attachable vaporization module 2 is configured to be received in the receiving area 306 at an interior side of the seal formed between the module housing 501 and the mouthpiece housing 301. For example, the battery receiving area 504 may be partly or entirely contained within the mouthpiece housing 301.

Referring to FIGS. 7A-7B and 9A-9B, according to embodiments herein, the one or more sealing regions 503 of the removably attachable vaporization module 2 comprise one or more sealing rings 511 provided about a circumference of an outer surface 512 of the insert portion 502, and which engage an inner surface 307 of the mouthpiece housing 301 in the receiving area 306 to form the seal between the insert portion 502 of the module housing 501 and the inner surface 307 of the mouthpiece housing 301. In yet another embodiment, the seal formed between the module housing 501 and mouthpiece housing 301 at least partly defines the interior chamber 302 of the mouthpiece 3 for flow of the gas having the vaporized product entrained therein from the receiving area 306 to the inhalation outlet 305.

Figure 10A:
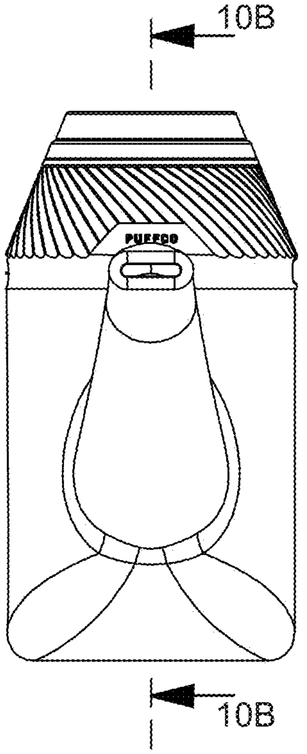
FIG. 10 A is a perspective view.
FIG. 10B is a cross-sectional view, of an embodiment of a device, with FIG. 10B providing a a representative gas flow path within the device 1, the gas flow path being illustrated via dashed lines and arrows.
Figure 10B:
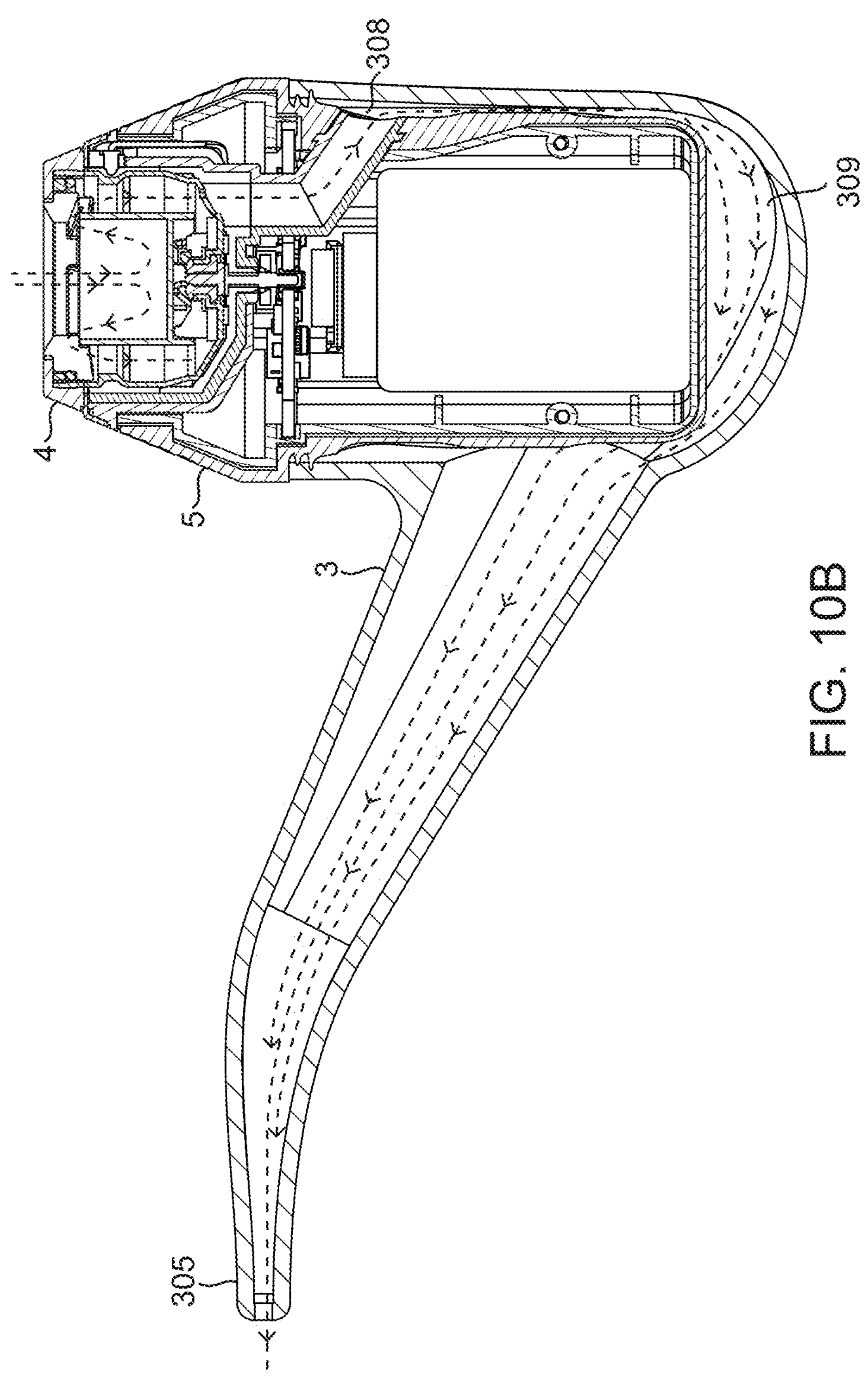
Figure 12A:
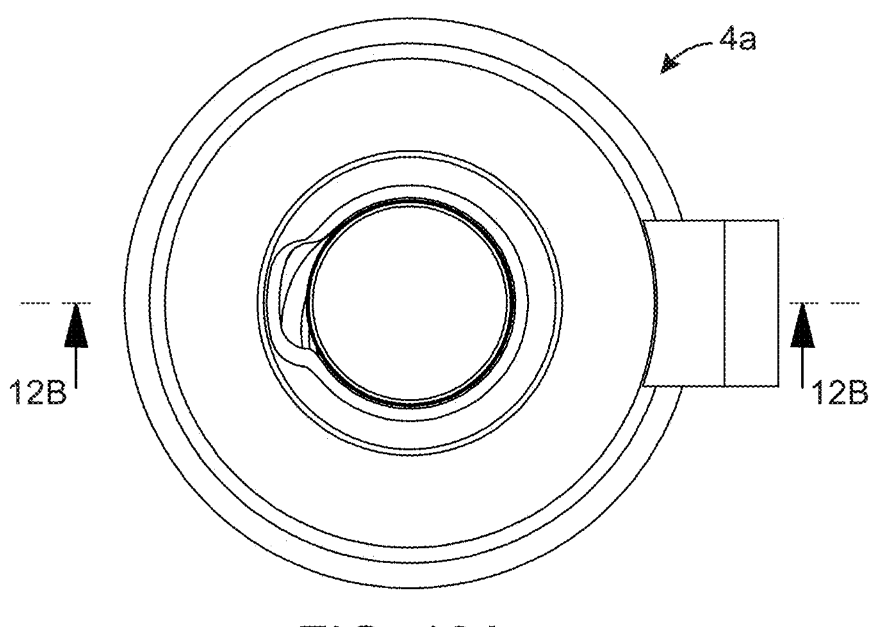
FIG. 12A is a top view of the embodiment of the vaporization assembly of FIGS. 11A-11E and FIG. 12B is a cross-sectional view of FIG. 12A.
Figure 12B:
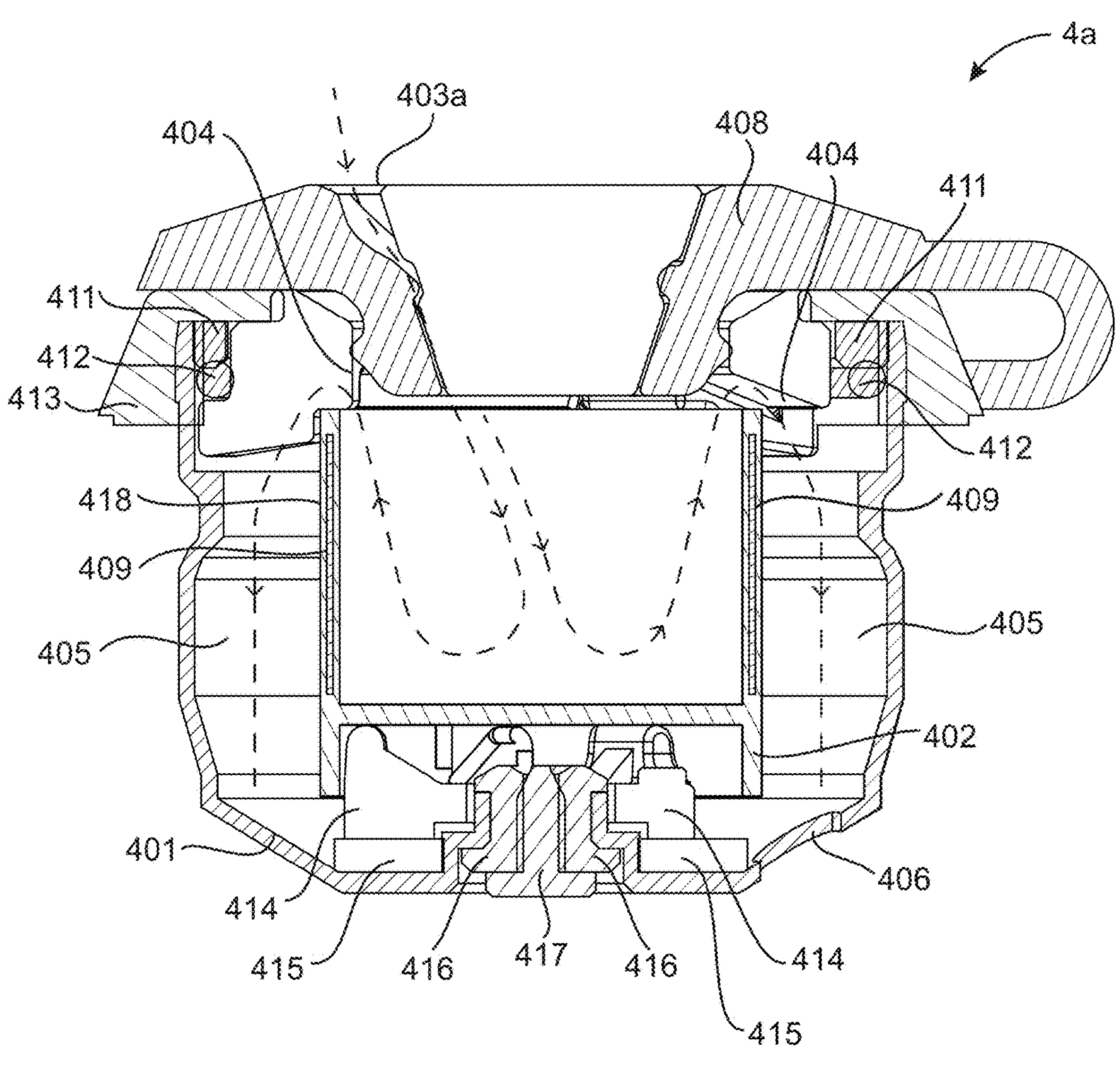
Figure 13A:
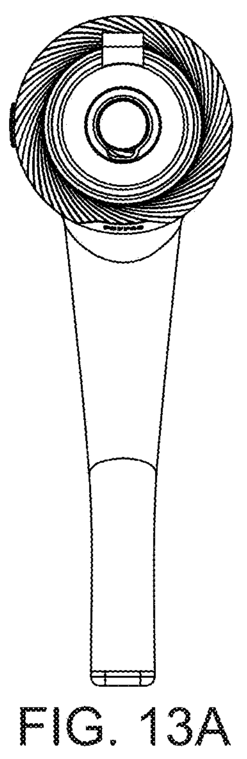
FIGS. 13A-13E show various view of an embodiment of an assembled device.
Figure 13B:
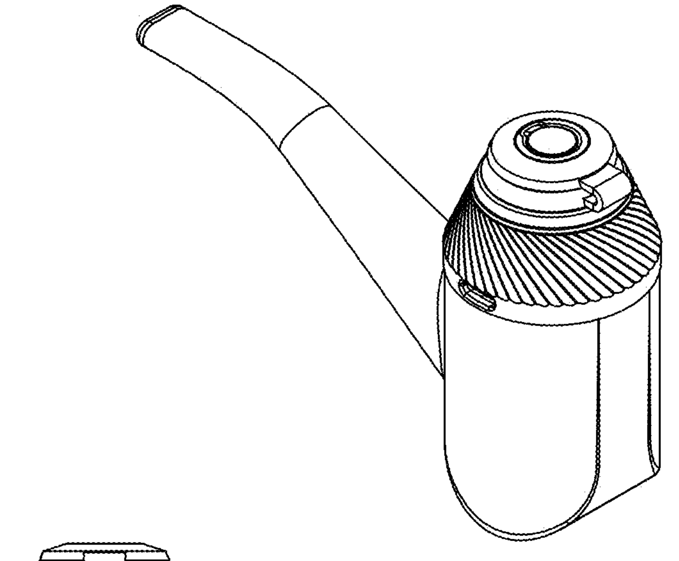
Figure 13C:
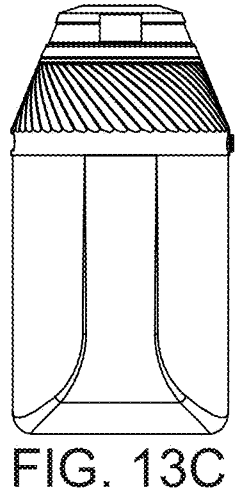
Figure 13D:
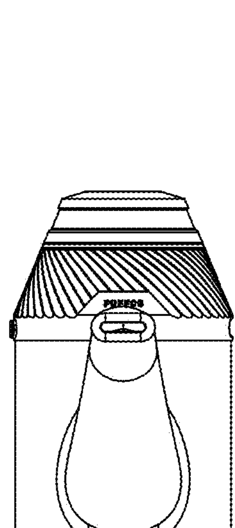
Figure 13E:
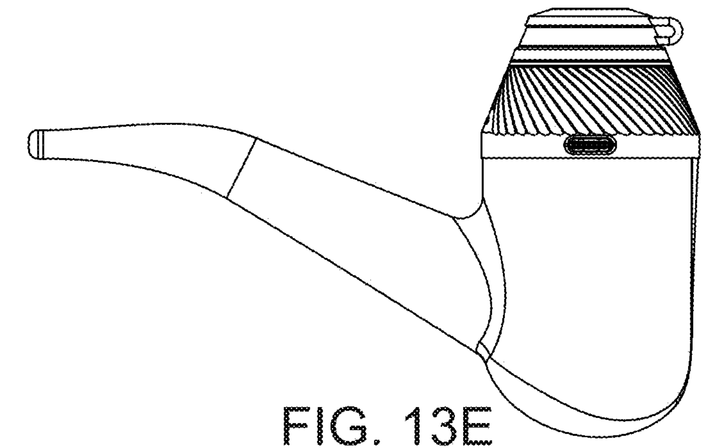

Referring to FIG. 10B, a representative gas flow path within the device 1 is illustrated in a cross-sectional view with dotted lines. A flow of ambient air enters the vaporization assembly 4 through the inlet 403, carries the vapor formed by the heated vaporable product in the refillable container 402, then passes through one or more refillable container outlets located near the top edge of the refillable container 402 and enters into the internal gas flow passage 405, and next leaves the vaporization assembly 4 through one or more vaporization assembly outlets 406, subsequently passes through the gas flow conduit 505 of the base portion 5 and enters the space between the module housing 501 and the mouthpiece housing 301, which is also below the one or more sealing regions 503. The vapor travels along the interior chamber 302 toward the inhalation outlet 305, and can be inhaled by a user.

In one embodiment, at least a portion of the interior chamber 302 of the mouthpiece 3 is defined by a passage formed between portions of the mouthpiece housing 301 and the surfaces of the insert portion 502. In yet another embodiment, in operation of the portable electronic vaporizing device 1, the flow of gas having vaporized product entrained therein is flowed past at least a portion of the battery receiving area 504 of the insert portion 502 before reaching the inhalation outlet 305. For example, as the insert portion 502 comprising the battery receiving area 504 is disposed within the mouthpiece housing 301, and in between the vaporization assembly 4 and the inhalation outlet 305, gas exiting the vaporization assembly 4 flows past the battery receiving area 504 of the insert portion 502 as it travels towards the inhalation outlet 305.

In one embodiment, the output opening 509 of the gas flow conduit 505 is positioned to output the flow of gas from the removably attachable vaporization module to one or more of: (i) a region 308 of the receiving area 306 adjacent the module housing 501, and between the module housing 501 and the mouthpiece housing 301; and (ii) a region 309 of the receiving area 306 below the module housing 501.

In a certain embodiment of the device disclosed herein, the refillable container 402 is disposed above the battery receiving area 504 of the insert portion 502; the inlet 403 to the refillable container 402 has a diameter of at least 5 mm; and/or the inlet 403 to the refillable container 402 is disposed above the receiving area 306 of the mouthpiece 3.

Figure 14A:
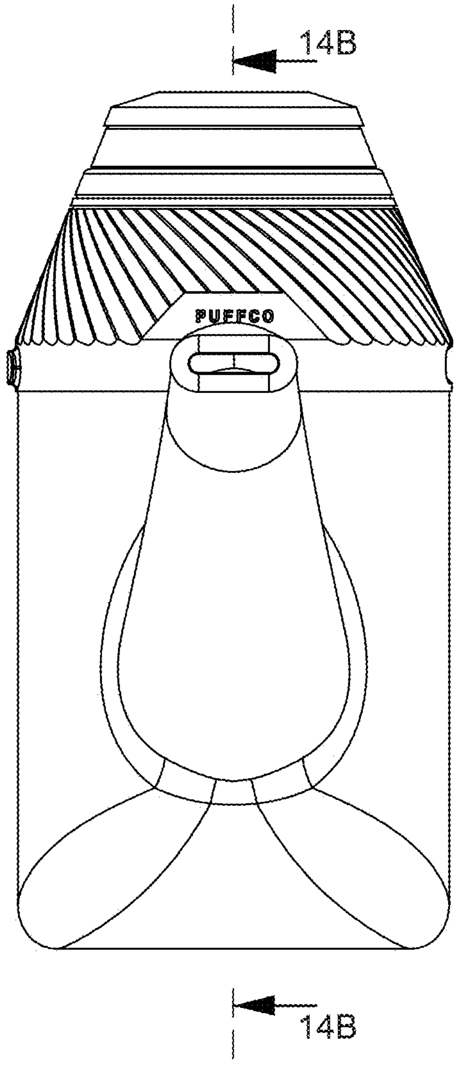
FIG. 14A is a front view of the embodiment of the assembled device of FIGS. 13A-13E.
Figure 14B:
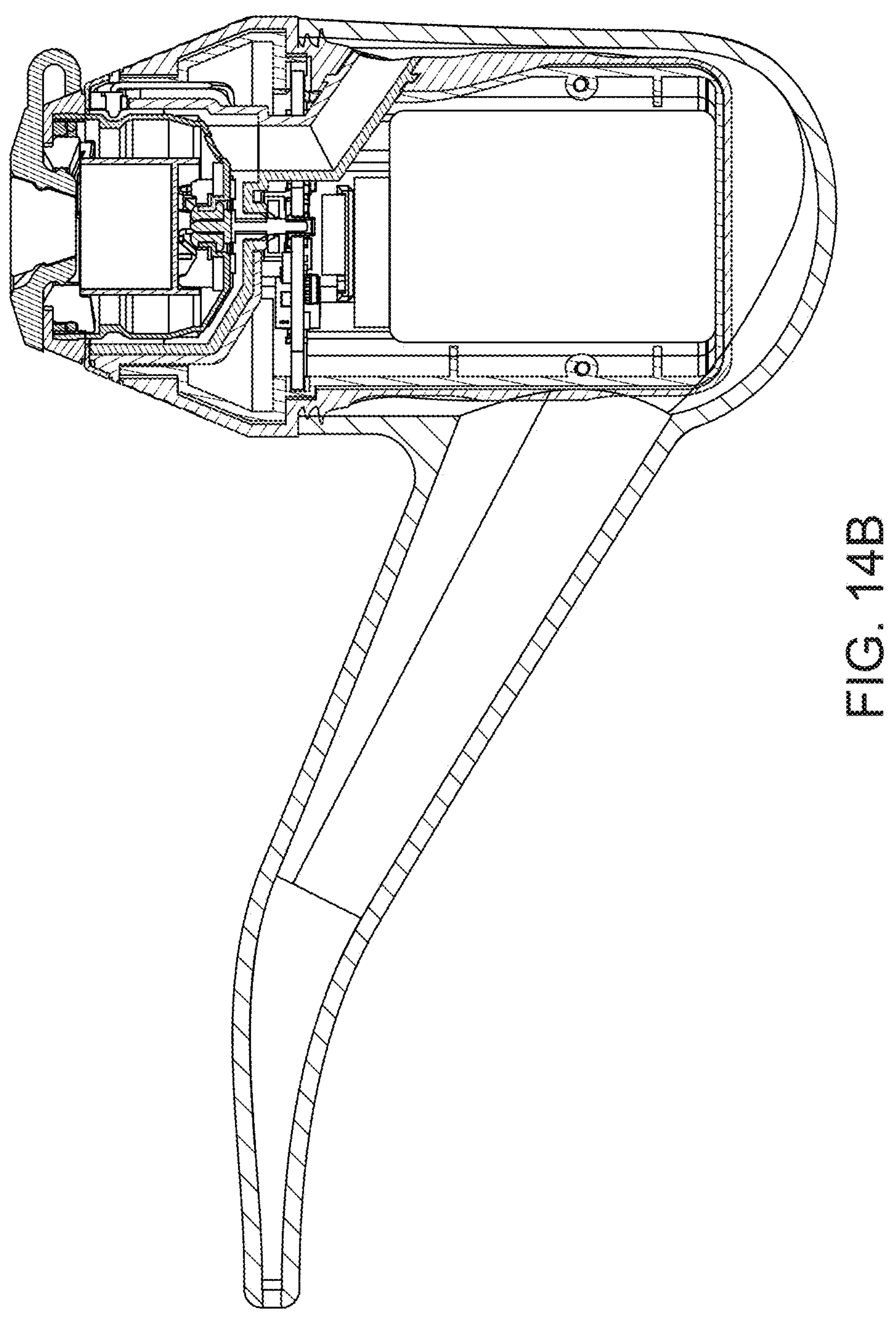
FIG. 14B is a cross-sectional view of FIG. 14A.

In one embodiment, to increase the efficiency of the vaporization, an alternative design of the vaporization assembly can be used. As shown in FIGS. 11A-11E and 12A-12B, the vaporization assembly 4*a* has a cap 408 to form a closed space with the refillable container 402. Instead of the relatively wide-open inlet 403, a flow of ambient air enters the vaporization assembly 4*a* through a small air inlet 403*a* on the cap 408, carries the vapor formed by the heated vaporable product in the refillable container 402, then passes through one or more refillable container outlets 404 located near the top edge of the refillable container 402 and enters into the internal gas flow passage 405, and eventually leaves the vaporization assembly 4 through the vaporization assembly outlets 406. An embodiment of the gas flow path within the vaporization assembly 4 is illustrated in dashed line. A cross-section view of the assembled portable electronic vaporizing device 1 equipped with the vaporization assembly 4*a* is shown in FIGS. 14A-14B. The gas flow path within the portable electronic vaporizing device 1 sequentially passing through the base portion 5 and the mouthpiece 3 is, in certain embodiments essentially the same as illustrated in FIGS. 10A-10B, and therefore is not shown in details.

According to embodiments herein, one or more airtight seals are formed between the base portion 5 and/or the vaporization assembly 4 (4*a*) and the mouthpiece 3, so as to create an airtight gas flow path between from the vaporization assembly 4 (4*a*), through the gas flow conduit 505 in the base portion 5, and to the mouthpiece 3. In the embodiments as shown, the gas flow conduit 505 in the base portion 5 separates a vaporization assembly internal gas flow path from a mouthpiece internal flow path.

Figure 3B:
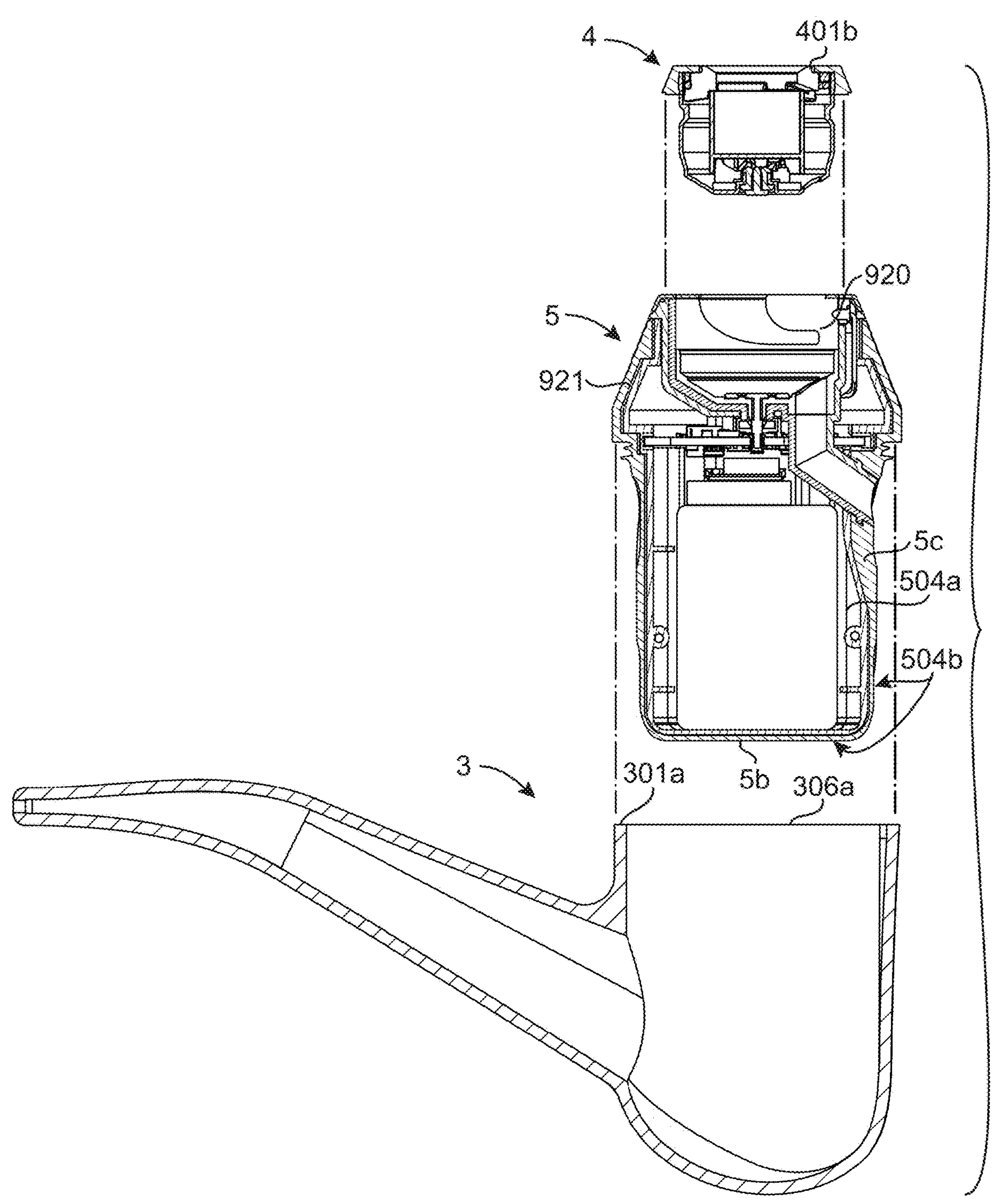
FIG. 3B is a cross-sectional side view of FIG. 3A.
Figures 4A, 4B, 4C, 4D, 4E:
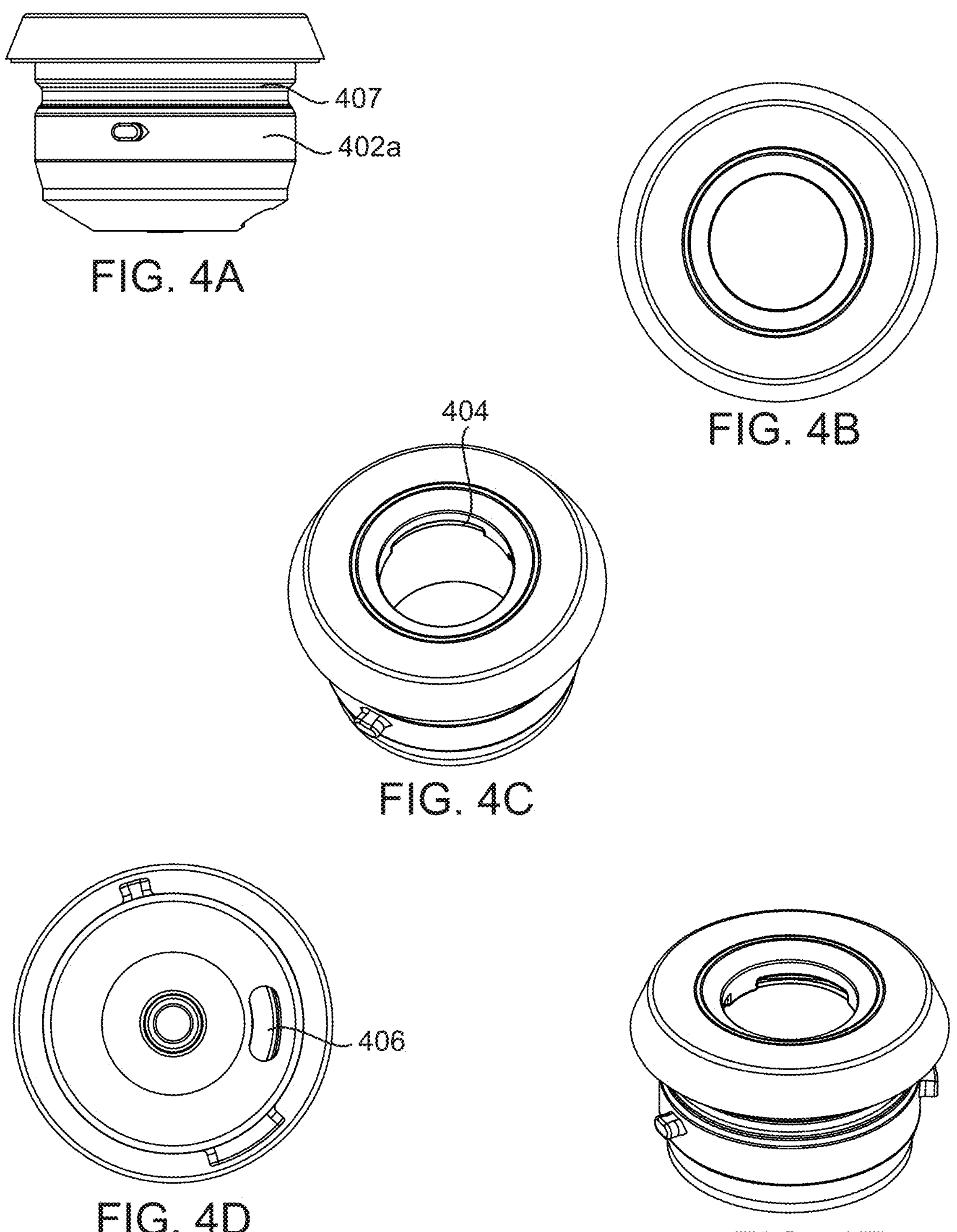
FIGS. 4A-4E show an embodiment of a vaporization assembly in various views.

In one embodiment, the vaporization assembly 4 is removably attachable to the base portion 5 via a fastening feature 407 that allows for repeated removal and re-insertion of the vaporization assembly into the base portion 5. For example, the vaporization assembly 4 may be removable by simply lifting or twisting. In one embodiment, as shown in FIGS. 2 and 3A-3B, the vaporization assembly 4 is attachable/removable by simply inserting into or lifting from the base portion 5. In yet another embodiment, as shown in FIGS. 4A-4E, 5A-5B and 11A-11E, the vaporization assembly 4 (4*a*) has a fastening feature 407 that is threaded, and that may be complementary to a threaded socket in the base portion 5, so the vaporization assembly can be screwed into the threaded socket of the base portion 5. In yet another embodiment the vaporization assembly 4 may connect to the base portion via a magnet, span mechanism or other fastening feature. According to embodiments herein, the fastening feature 407 may be located on the base portion 5, and/or the fastening feature 407 may be located on one or more of the vaporization assembly 4 and mouthpiece 3, and/or the components may have mutually complementary fastening features that allow for repeatable removal and re-attachment of the vaporization assembly 4 and/or mouthpiece 3 to the base portion 5.

According to another aspect of the present disclosure, a method of using the portable electronic vaporizing device disclosed herein is provided. For example, the method may comprise: inserting the removably attachable vaporization module into the receiving area of the mouthpiece; providing vaporizable product to the product receiving chamber, or refillable container, of the removably attachable vaporization module; activating the heating device to heat the vaporizable product in the product receiving chamber to at least partly vaporize the product; and inhaling gas entrained with the vaporizable product from the inhalation outlet of the mouthpiece. In another embodiment, the method may further comprise assembling the removably attachable vaporization module by inserting the removably attachable atomizer assembly into the receiving area of the base portion and aligning one or more of the vaporization assembly outlets with the gas flow conduit, either before or after insertion of the base portion of the removably attachable vaporization module into the receiving area of the mouthpiece.

According to yet another aspect of the invention, a removably attachable base portion of a removably attachable vaporization module is provided for vaporizing a vaporizable product in a portable vaporizing device having a receiving body to receive the removably attachable base portion in a receiving region thereof. The removably attachable base portion comprises: a housing having an insert portion configured to be at least partly received within the receiving area of the receiving body, the insert portion having one or more sealing regions configured to form a seal between the housing and one or more walls of the receiving body, and a battery receiving area disposed within the insert portion and configured to receive a battery for powering the removably attachable vaporization module; and a gas flow conduit having an output opening positioned to output the flow of gas from the removably attachable base portion to the receiving area of the receiving body at an interior side of the seal between the housing and the one or more walls of the receiving body.

In one embodiment, the removably attachable vaporization module may further comprise a vaporization assembly. The vaporization assembly may comprise a vaporization assembly housing, a refillable container configured to receive a vaporizable product within the vaporization assembly housing, a heating device configured to be electrically connected to the battery and transfer energy to the vaporizable product in the refillable container to heat the product and form a vapor therefrom, an inlet configured to introduce gas into the refillable container, one or more refillable container outlets configured to receive a flow of gas having vaporized product entrained therein from the refillable container, one or more vaporization assembly outlets configured to provide the flow of gas received from the refillable container outlets to the input opening of the gas flow conduit in the base portion. Optionally, the vaporization assembly is removably attachable to the base portion. According to yet another embodiment, the removably attachable vaporization module is configured to be removably attached to a receiving body comprising a mouthpiece of a portable vaporizing device.

Figure 5C:
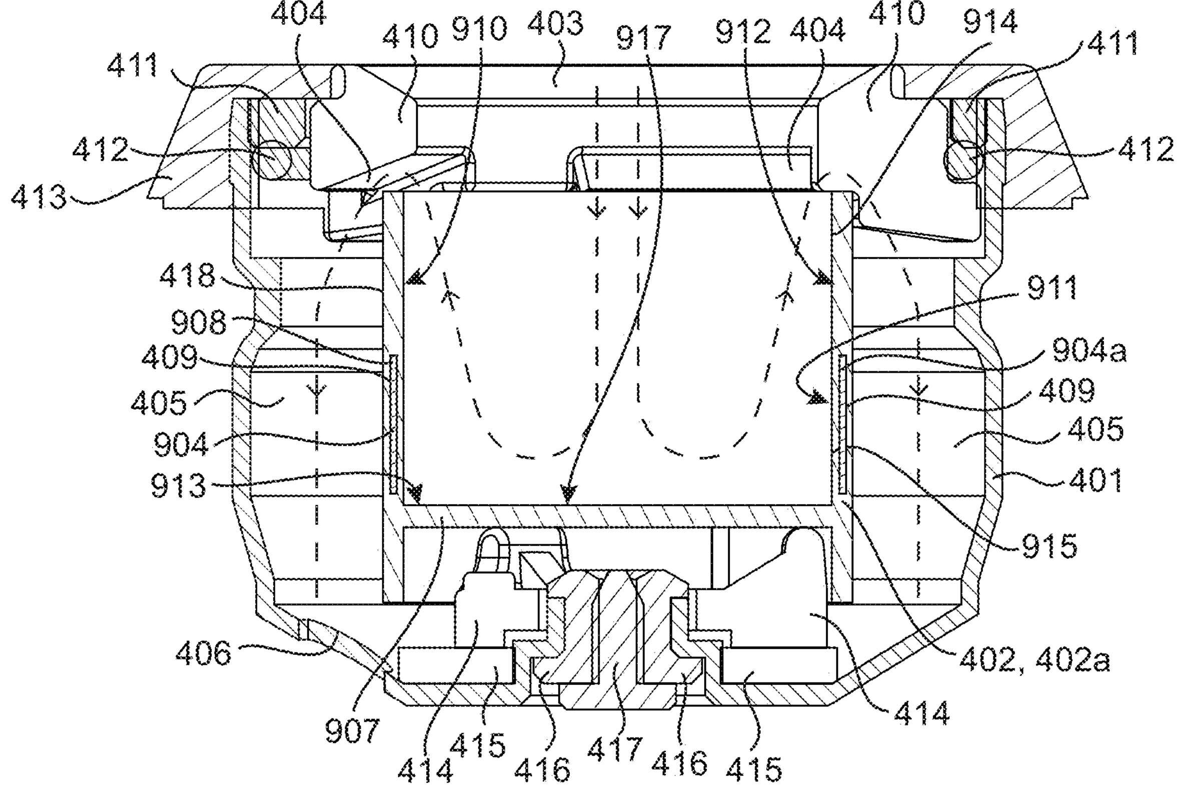
FIG. 5C is a cross-sectional view of the vaporization assembly of FIG. 5A having a container comprising a heating device with one or more embedded resistive heating elements, as described in one embodiment of this invention.
Figure 5E:
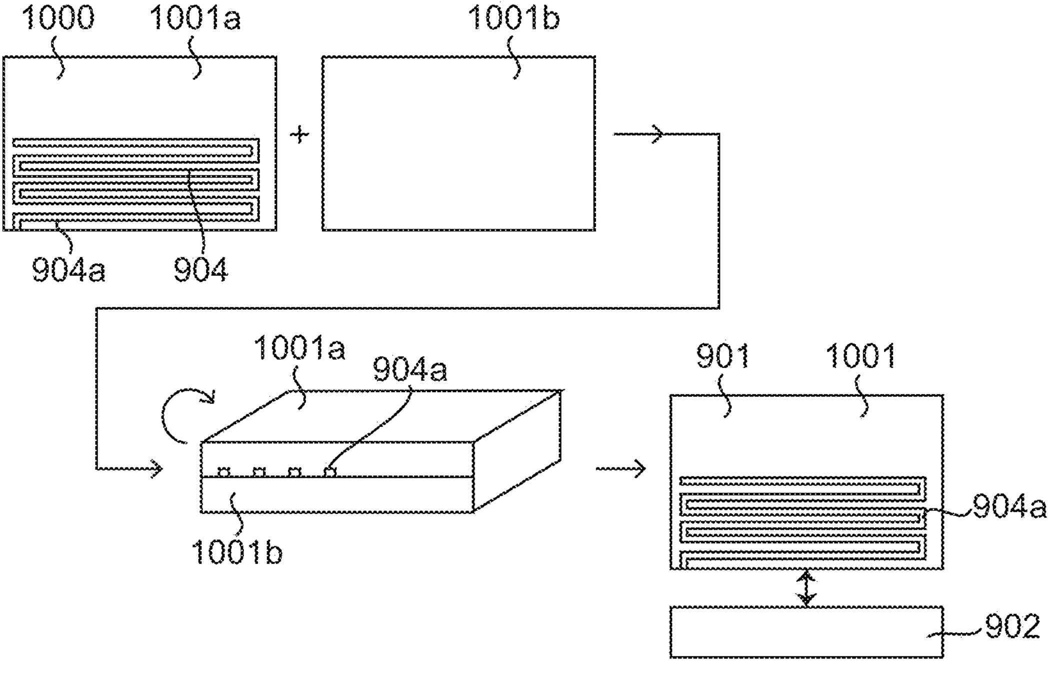
FIG. 5E schematically depicts steps in a method of manufacturing a container having embedded heater traces, according to an embodiment of the invention.
Figure 5D:
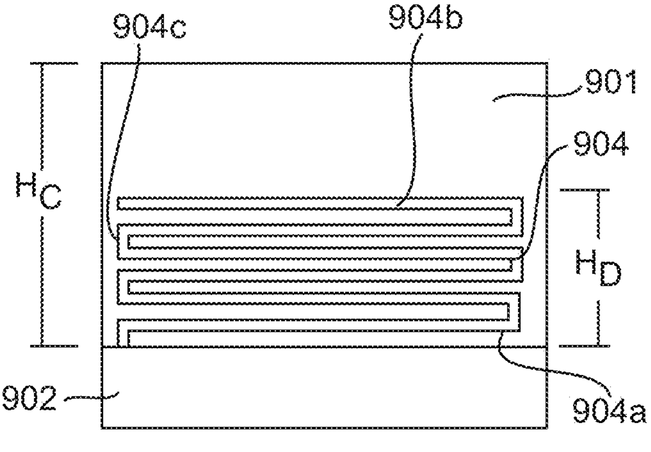
FIG. 5D is a schematic view of a container for a vaporization assembly, showing embedded heater traces, according to an embodiment of the invention.

Referring to FIGS. 5B-5D, according to another aspect of the invention, a container 402*a* used to hold vaporizable product in a portable electronic vaporizing device 1 is provided. According to certain embodiments, the container 402*a* may be a refillable container 402 as described elsewhere herein that can be filled and then re-filled with vaporizable product for re-use of the container, and/or may be a pre-filled container that is pre-filled with a vaporizable product before purchase by a consumer (e.g. for one-time use, or that may be subsequently re-filled). According to embodiments herein, the container 402*a* comprises container walls 900 comprising one or more sidewalls 901 and a bottom wall 902 that form a space 903 to receive the vaporizable product. According to further embodiments, the container 402*a* further comprises a heating device 409 comprising one or more resistive heating elements 904 embedded in one or more of the container walls 900. The heating device 409 is configured to be electrically connected to a battery 518 or other source of electrical power and transfer energy to the vaporizable product in the container to heat the product and form a vapor therefrom.

According to certain embodiments, the container 402*a* comprises a bottom wall 902 and lower regions 915 of the one or more sidewalls 901 that form a continuous barrier to the passage of gas and/or liquid into or out of the container 402*a*. For example, in certain embodiments, the bottom wall 902 of the container 402*a* and lower regions 915 of the one or more sidewalls 901 of the container 402*a* are non-porous. In certain other embodiments, the container 402*a* does not contain gas inlets and/or outlets on the bottom wall 902 or lower regions 915 of the one or more sidewalls 901. In some embodiments, the bottom wall 902 of the container 402*a* and lower regions 915 of the one or more sidewalls 901 of the container 402*a* are substantially and/or entirely impermeable to a flow of gas or liquid therethrough. In some other embodiments, the bottom wall 902 of the container 402*a* and lower regions 915 of the one or more sidewalls 901 of the container 402*a* are configured to contain a vaporizable product that is liquid or that becomes at least partially liquefied during vaporization thereof. For example, in certain embodiments, the container 402*a* may be one intended for use of vaporizable product in liquid, wax, or other liquefiable form, as opposed to a herbal form.

In some embodiments, the heating device 409 comprises one or more resistive heating elements 904 embedded in sidewall heating portions 906 of the one or more sidewalls 901. The sidewall heating portions 906 are those portions of the one or more sidewalls containing the one or more resistive heating elements 904 therein, as opposed to portions of the one or more sidewalls 901 that do not contain any resistive heating elements therein 904 (i.e., non-heating portions of the sidewalls). In some other embodiments, the heating device 409 comprises one or more resistive heating elements 904 embedded in a bottom wall heating portion 907 of the bottom wall 902 (FIG. 5C depicts where a bottom wall heating portion 907 could be located, if a heating device comprising one or more resistive heating elements 904 were provided to this portion of the bottom wall 902 in this figure). The bottom wall heating portion 907 is that portion of the bottom wall 902 containing the one or more resistive heating elements 904 therein, as opposed to portions of the bottom wall 902 that do not contain any resistive heating elements 904 therein (i.e., non-heating portions of the bottom wall).

In yet other embodiments, the bottom wall 902 of the container 402*a* does not contain any resistive heating elements 904 embedded therein (e.g. as shown in FIGS. 5B-5C), and so may be entirely comprised of a non-heating portions. In another embodiment, the bottom wall 902 is entirely comprised of non-heating portions, and does not even contain any resistive heating elements 904 that are adjacent the bottom wall (e.g., no heating coil or heating plate provided under the bottom wall 902). As used herein with reference to embedded resistive heating elements 904, "embedded" means that the resistive heating elements (e.g., heater traces) contain embedded portions 908 that at least partly, and even entirely, covered by one or more materials forming the container walls 900, such that the embedded portions 908 are not exposed to the environment external to container. The embedded portions 908 of the resistive heating elements 904 can, in certain embodiments, make up at least 75%, at least 85%, at least 95%, and/or at least 99%, and even the entirety, of the volume of the one or more resistive heating elements 904. In certain embodiments, the at least 75%, at least 85%, at least 95%, and/or at least 99%, and even the entirety of the surface area of the one or more resistive heating elements 904 is embedded. In one embodiment, the resistive heating elements 904 are substantially covered and/or surrounded by material made of the container walls 900 and thereby have substantially no direct physical contact with the vaporizable product in the container 402*a*, and/or also have substantially no exposure to any environment external to the container 402*a*.

In one embodiment, the one or more container walls 900 comprise a ceramic material comprising metal heater traces 904*a* embedded therein. For example, the ceramic material may be any that provides good heat transfer from the metal heater traces 904*a* through the container walls 900 and to the vaporizable product. In one embodiment, the one or more container walls 900 comprise a ceramic material comprising any of silicon carbide, alumina, aluminum nitride, zirconia, quartz, ruby, sapphire, bososilicate, and combinations thereof, and the one or more metal heater traces 904*a* comprise any of tungsten, kanthal, titanium, stainless steel, and nickel, and combinations thereof. In a further embodiment, the one or more resistive heating elements 904 are embedded in the one or more container walls 900 such that a thickness of the one or more container walls 900 on either side of the embedded resistive heating element 904 is at least 0.1 mm, at least 0.15 mm, and/or at least 0.2 mm. In one embodiment, the one or more container walls 900 comprising the one or more embedded resistive heating elements 904 therein, comprise an overall thickness of at least 0.5 mm, at least 0.6 mm, and/or at least 0.8 mm.

Manufacturing wise, the one or more resistive heating elements 904 can be embedded in the one or more container walls 900 by any feasible method in the art. For example, in one embodiment, with reference to FIG. 5E, the container 402*a* is formed by embedding the resistive heating element 904 in a soft ceramic material 1000 (e.g. a "green" or unsintered ceramic) and forming a tube shape 1001, adhering a thin ceramic bottom wall 902 to the tube shape 1001, and firing the soft ceramic tube shape with the resistive heating element embedded therein. In another embodiment, the container is formed by printing metal heater traces 904*a* onto a first layer 1001*a* of soft ceramic material, covering the printed metal heater traces with a second layer 1001*b* of soft ceramic material to embed the printed metal heater traces 904*a* between the first and second layers 1001*a*, 1001*b* of the soft ceramic material, wrapping the first and second layers 1001*a*,1001*b* of soft ceramic material having the printed metal heater traces embedded therebetween into a tube shape 1001, adhering a thin ceramic bottom wall 902 to the tube shape, and firing the soft ceramic tube shape with the printed metal heater traces embedded therein.

According to certain embodiments, the heating device 409 can be configured such that, during operation of the container, the container will not necessarily be uniformly heated to the same extent. For example, in one embodiment, the bottom wall 902 of the container has no heating device embedded therein. Moreover, in certain embodiments, the one or more sidewalls may comprise non-heating portions. For example, referring to FIG. 5D, in one embodiment, the heating device 409 comprises one or more resistive heating elements 904 embedded in sidewall heating portions 906 of the one or more sidewalls 901, wherein the one or more sidewalls extend vertically from the bottom wall 902 to a vertical height $H_C$, and wherein the sidewall heating portions 906 extend vertically from the bottom wall 902 to a vertical height $H_D$ along the one or more sidewalls, and wherein the vertical height $H_D$ of the sidewall heating portions 906 having the one or more resistive heating elements 904 embedded therein is lower than the height $H_C$ of the one or more sidewalls 901 of the container 402*a*. In some embodiments, the vertical height $H_D$ of sidewall heating portions 906 is lower than the height of the sidewalls $H_C$ of the container 402*a*, such that $H_D$ is less than 90%, less than 80%, less than 75%, less than 70%, less than 65%, less than 60%, less than 55%, less than 45%, less than 40%, less than 35%, and/or less than 30% of $H_C$. In some embodiments, the vertical height $H_D$ of sidewall heating portions 906 is lower than the height of the sidewalls $H_C$ of the container 402*a*, such that $H_D$ is at least 5%, at least 10%, at least 15%, at least 20%, at least 25%, at least 30%, at least 35%, at least 40%, at least 45%, and/or at least 50% of $H_C$. That is, in certain embodiments, an extent of the one or more resistive heating elements 904 in the vertical direction along the one or more sidewalls 901 is less than 90%, less than 80%, less than 75%, less than 70%, less than 65%, less than 60%, less than 55%, less than 45%, less than 40%, less than 35%, and/or less than 30% of $H_C$. In another embodiment, an extent of the one or more resistive heating elements 904 in the vertical direction along the one or more sidewalls 901 is at least 5%, at least 10%, at least 15%, at least 20%, at least 25%, at least 30%, at least 35%, at least 40%, at least 45%, and/or at least 50% of $H_C$.

Referring to FIG. 5C, in some embodiments, the one or more sidewalls 901 of the container 402*a* have an interior sidewall surface 910 facing the interior of the container, and wherein a ratio of that portion of the interior sidewall surface 910 corresponding to the interior surface 911 of the sidewall heating portions 906 having the embedded resistive heating elements, to the total surface area of interior sidewall surface 910 is less than 90%, less than 80%, less than 75%, less than 70%, less than 65%, less than 60%, less than 55%, less than 45%, less than 40%, less than 35%, and/or less than 30%. In some embodiments, sidewall portions of the container without resistive heating elements embedded therein (non-heating portions) have an interior surface 912, which makes up at least 5%, at least 10%, at least 15%, at least 20%, at least 25%, at least 30%, at least 35%, at least 40%, at least 45%, at least 50%, at least 55%, and/or at least 60% of the total surface area of the interior sidewall surface. In some embodiments, the container 402*a* comprises an interior container surface 913 comprising the interior sidewall surface 910 and an interior surface 917 of the bottom wall 902, and wherein that portion of interior container surface 913 corresponding to an interior surface 911 of the sidewall heating portions is less than 90%, less than 80%, less than 75%, less than 70%, less than 65%, less than 60%, less than 55%, less than 45%, less than 40%, less than 35%, and/or less than 30% of the total interior container surface area. In some embodiments, sidewall portions of the container without resistive heating elements embedded therein (non-heating portions) have an interior surface 912, which makes up at least 5%, at least 10%, at least 15%, at least 20%, at least 25%, at least 30%, at least 35%, at least 40%, at least 45%, at least 50%, at least 55%, and/or at least 60% of the total interior container surface area.

In some embodiments, during operation, the sidewall heating portions 906 are heated to a temperature higher than that of the bottom wall 902 and/or the sidewall portions without resistive heating elements 904 embedded therein (non-heating portions 914 of the one or more sidewalls). For example, in one embodiment, a power delivered to the resistive heating elements 904 in the one or more sidewall heating portions 906 is greater than any power delivered to resistive heating elements 904 in the bottom wall, and/or no power is delivered to any resistive heating elements 904 in the bottom wall (e.g. the bottom wall does not contain resistive heating elements). In another embodiment, the container comprises sidewall and bottom wall heating portions 906, 907 comprising resistive heating elements 904 embedded therein, and the resistive heating elements 904 embedded in the bottom wall heating portions 907 comprise a higher resistance than resistive heating elements embedded in the one or more sidewall heating portions 906.

Dimension wise, in one embodiment, the one or more sidewall heating portions 906 having the one or more resistive heating elements 904 embedded therein. comprise a height of no more than 10 mm, no more than 9 mm, no more than 8 mm, no more than 7.5 mm, and/or no more than 7.5 mm, as measured from the bottom wall 902, and can comprise a height of at least 2 mm, at least 2.5 mm, at least 3 mm, at least 4 mm, at least 5 mm, at least 5.5 and/or at least 5.75 mm, as measured from the bottom wall 902. In certain embodiments, the one or more resistive heating elements 904 are provided only to lower regions 915 of the one or more sidewalls 901 and/or the one or more sidewall heating portions 906 comprise only lower regions 915 of the one or more sidewalls. For example, in one embodiment, an extent of the one or more resistive heating elements 904 in the vertical direction along the one or more sidewalls comprises a height of no more than 10 mm, no more than 9 mm, no more than 8 mm, no more than 7.5 mm, and/or no more than 7.5 mm, as measured from the bottom wall 902, and can comprise a height of at least 2 mm, at least 2.5 mm, at least 3 mm, at least 4 mm, at least 5 mm, at least 5.5 and/or at least 5.75 mm, as measured from the bottom wall 902.

In some embodiments, the heating device 409 comprises one or more resistive heating elements 904 that are capable of conductively heating the vaporizable product in the container 402*a*, such as via conduction of heat from embedded heater traces 904*a* through a ceramic or other thermally conductive material of the container, and to the vaporizable product in the container. In some embodiments, the one or more resistive heating elements 904 comprise one or more heater traces 904*a* that extend at least partly circumferentially about the interior of the container 402*a*. In some embodiments, the one or more heater traces 904*a* form a switchback pattern across at least a portion of the one or more sidewall heating portions 906, as shown for example in FIG. 5D. In some embodiments, the one or more heater traces comprise a plurality of substantially horizontal segments 904*b* at least partly circumferentially surrounding the interior of the container, and comprise a plurality of substantially vertical segments 904*c* connecting the substantially horizontal segments 904*b*, as shown in FIG. 5D.

According to one embodiment, the container 402*a* may be used with any suitable portable electronic vaporizing device 1, such as any described herein, including as shown in in FIGS. 1-14B. In one embodiment, the container can also be used in other compatible portable electronic vaporization devices, such as those described in U.S. Pat. Nos. 10,517,334, 11,000,067 and 11,140,924. As a further example, FIGS. 19-30 provide another example of a portable electronic vaporizing device 1 in which the container can be used, as described for example in U.S. Pat. No. 10,517,334 issued on Dec. 31, 2019 (Ser. No. 16/373,170), which is hereby incorporated by reference herein in its entirety, and as described further herein, the present disclosure provides portable electronic vaporizing device comprising the refillable container disclosed herein. In one embodiment, the portable electronic vaporizing device comprises a mouthpiece configured to receive vaporizable product that is vaporized in the refillable container, the mouthpiece having an inhalation outlet for inhaling of the vaporized product.

Referring to FIGS. 11-14B, according to one embodiment, the portable electronic vaporizing device suitable for the container 402*a* having the one or more embedded resistive heating elements comprises the removably attachable vaporization module 2, and the mouthpiece 3 configured to receive the flow of gas having vaporizable product entrained therein from the removably attachable vaporization module 2. The mouthpiece 3 comprises the mouthpiece housing 301 at least partly defining the interior chamber 302; the inhalation outlet 305 formed in the mouthpiece housing 301; and the receiving area 306 for receiving the battery-powered removably attachable vaporization module 2 in the interior chamber 302 of the mouthpiece housing 301. The removably attachable vaporization module 2 comprises the base portion 5 comprising the module housing 501 having the insert portion 502 configured to be at least partly received within the receiving area 306 of the mouthpiece housing 301, the insert portion 502 having one or more sealing regions 503 configured to form the seal between the module housing 501 and the mouthpiece housing 301, and the battery receiving area 504 disposed within the insert portion 502 and configured to receive the battery 518 for powering the vaporization module, and the gas flow conduit 505 having the input opening 510 and the output opening 509 positioned to output the flow of gas from the removably attachable vaporization module 2 to the receiving area 306 of the mouthpiece 3 at the interior side of the seal between the module housing 501 and the mouthpiece housing 301. The vaporization assembly 4 comprises the vaporization assembly housing 401; the container 402*a* (e.g. refillable container 402) have having the one or more embedded heating traces 904*a* disclosed herein, configured to receive the vaporizable product within the vaporization assembly housing 401; the inlet 403 configured to introduce gas into the container 402*a*; one or more refillable container outlets 404 configured to receive the flow of gas having vaporized product entrained therein from the container (402*a*); and one or more vaporization assembly outlets 406 configured to provide the flow of gas received from the refillable container outlets 404 to the input opening 510 of the gas flow conduit 505 in the base portion. In operation of the portable electronic vaporizing device, the flow of gas having the vaporized product entrained therein is passed through the gas flow conduit and received into the receiving area of the mouthpiece from the output opening of the gas flow conduit, and is passed along the interior chamber of the mouthpiece to the inhalation outlet. An exemplary vaporization assembly having the container with embedded heater traces in a lower region of the sidewalls is shown in FIG. 5C.

Figure 19:
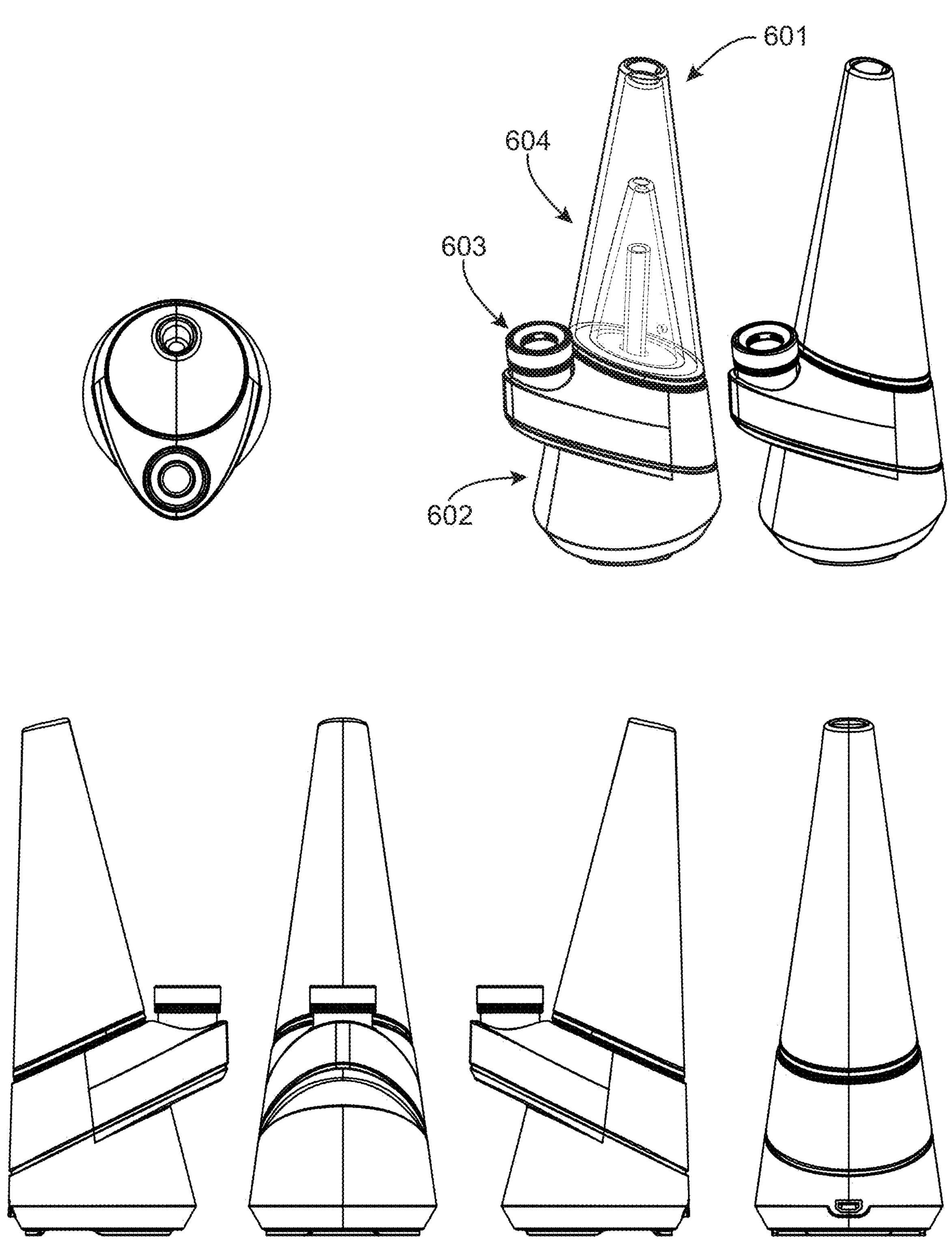
FIG. 19 shows embodiments of a portable electronic vaporizing device comprising a base, atomizer and mouthpiece.

Referring to FIGS. 19-30, a further embodiment of a portable electronic vaporizing device 1 suitable for use the container 402*a* having the one or more embedded resistive heating elements 904 is shown. Referring to FIG. 19, an embodiment of a portable electronic vaporizing device 601 is shown according to aspects of the disclosure herein. The portable electronic device 601 comprises a base 602, an atomizer 603, and a mouthpiece 604. The atomizer 603 is configured to receive a vaporizable product therein and to heat the vaporizable product to form a vapor therefrom. The mouthpiece 604 comprises an outlet where a user can inhale the vapor produced by the atomizer, optionally with water or other substances entrained therein. The base 602 provides a gas flow connection between the atomizer 603 and mouthpiece 604, to deliver the vaporized product from the atomizer 603 to the mouthpiece 604 for delivery to the use via inhalation thereof. The base 602 can also comprise a housing for one or more components for powering and/or controlling the device 601. For example, the base may contain compartments therein for storing a power source, such as a battery, for powering elements of the device 601 such as a heating element or other heating device used in the atomizer 603. In a case where the device is powered by a rechargeable battery, such as a lithium ion battery, the base 602 may also comprise a charging port connectable to a battery charger (not shown). The base may also have compartment doors to allow access to a battery or other components held within the housing. The base 602 may also house further control circuitry for controlling the device, such as to provide predetermined heating cycles or heating programs, and may also allow for user interaction with the device via control buttons and/or control interface, a display and/or lights to signal to the user, and/or other control and operation features.

Figure 20:
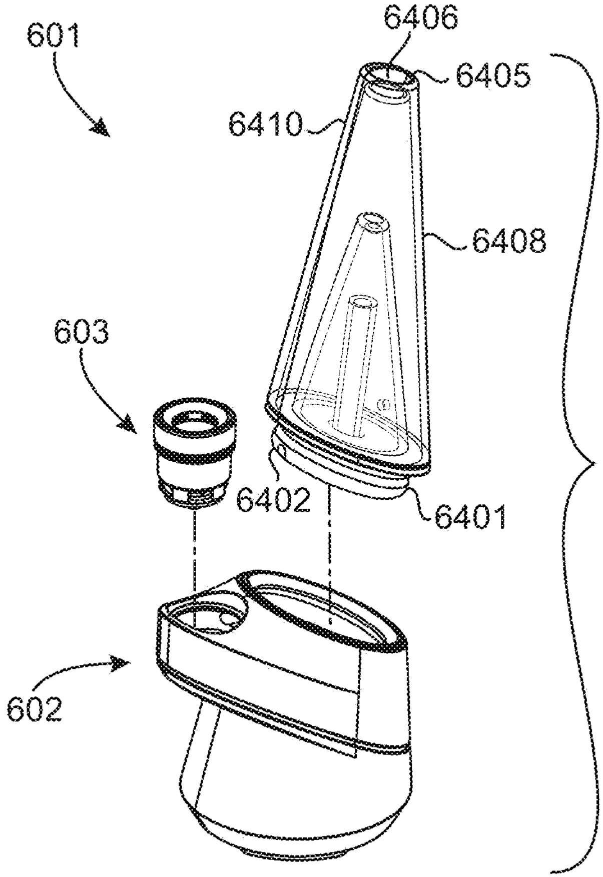
FIG. 20 is an exploded view of the device of FIG. 19.

Referring to FIG. 20, an embodiment of the device 601 is shown in exploded view, with the mouthpiece 604 and atomizer 603 removed from the base 602. In one embodiment, the mouthpiece 604 is removably attachable to the base 602, for example so as to allow a user to readily remove the mouthpiece for cleaning and/or replacement, as is described in further detail herein. In yet another embodiment, the atomizer may be removably attachable to the base, for example so as to allow a user to replace the atomizer 603 when no longer serviceable, for cleaning of the atomizer, and/or to more readily allow access to a container (e.g. bowl or a refillable container disclosed herein) where a vaporizable product may be loaded into the atomizer 603. In one embodiment, both the atomizer 603 and the mouthpiece 604 may be removably attachable to the base 602. In yet another version, the atomizer 603 may be independently removable from the base 602. That is, the atomizer 603 may be configured to be removably attached to the base such that it can be removed therefrom, without requiring that the mouthpiece 602 be removed beforehand.

Figure 21A:
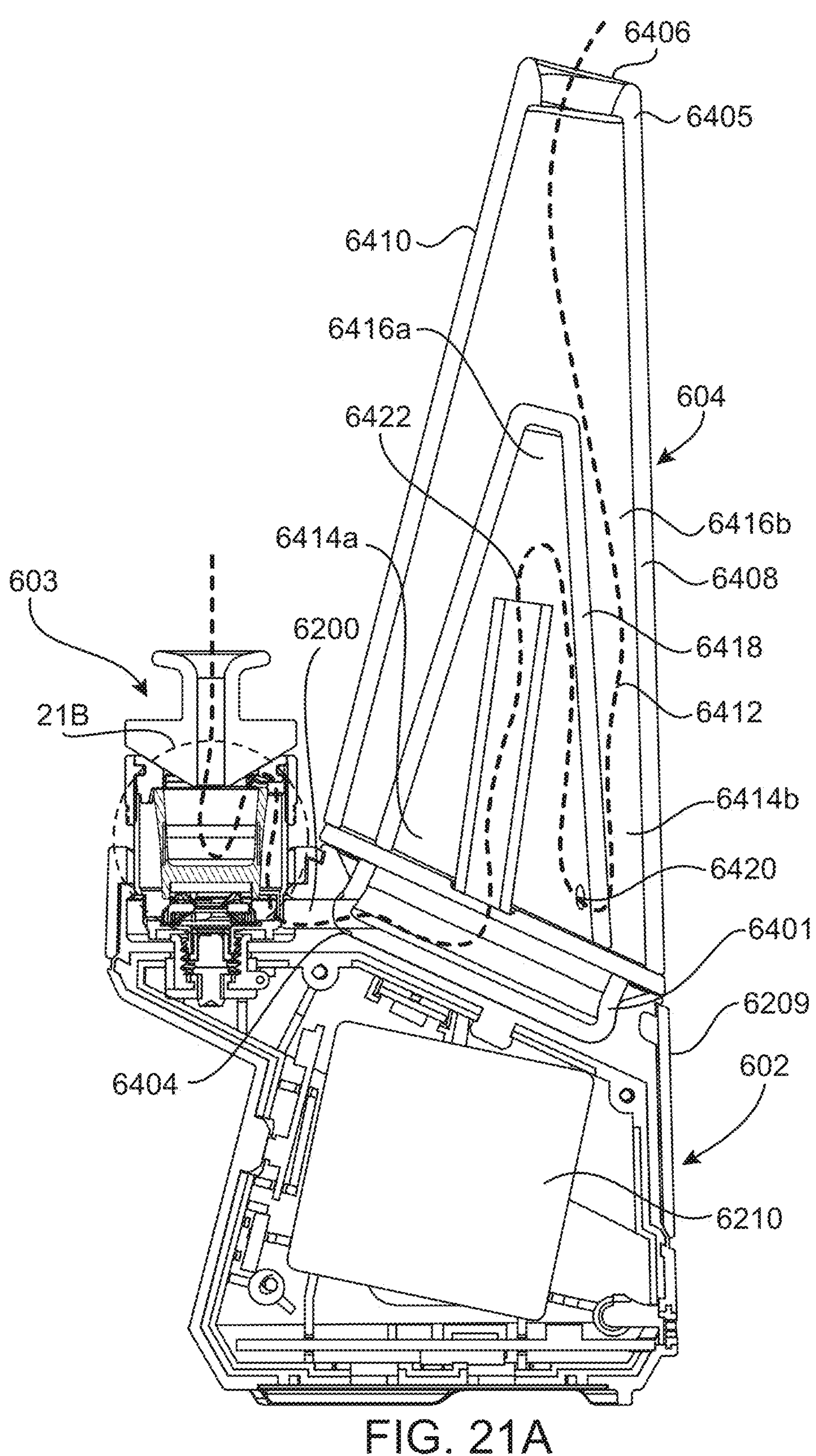
FIG. 21A is a schematic view of the device of FIG. 19.
Figure 21B:
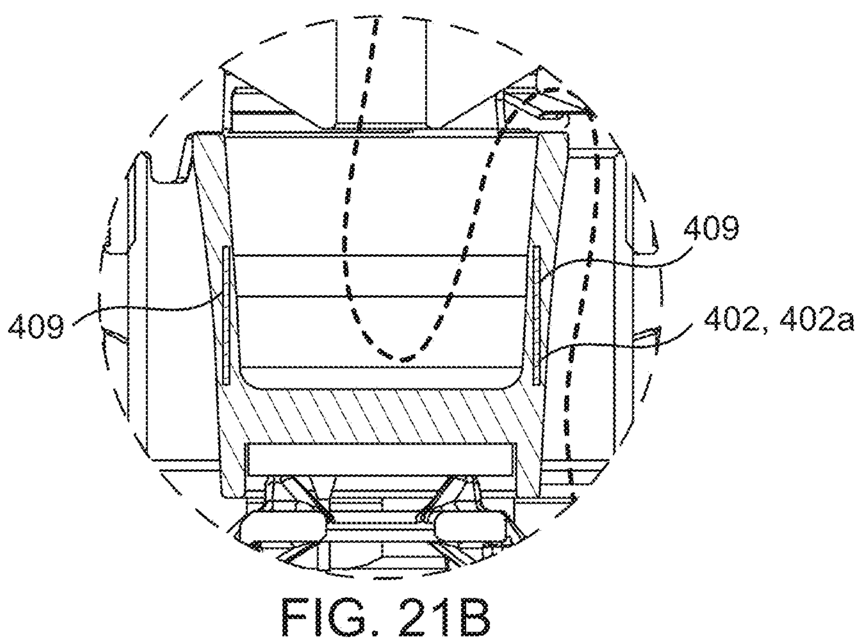
FIG. 21B is a cross-sectional schematic view of the device of FIG. 19, illustrating a container comprising a heating device with one or more embedded resistive heating elements, as described in one embodiment of this invention.

Referring to FIGS. 21A and 21B, an embodiment of a gas flow path through the portable electronic device 601 is shown. In one embodiment, a flow of ambient air is received in the atomizer 603, where the ambient air is entrained with vaporizable product that is vaporized in the atomizer via a heating element. The gas comprising the ambient air and vaporizable product flows from the atomizer 603 to a portion of the base 602 having a gas flow conduit therein, and which provide a sealed gas flow connection between the atomizer 603 and mouthpiece 604. The gas received into the mouthpiece 604, where it is directed to an inhalation outlet of the mouthpiece, where the gas comprising the vaporizable product can be inhaled by the user. In one embodiment, water is provided a region of the mouthpiece 604 such that water is entrained with the gas passing through the mouthpiece, thereby providing a more pleasant inhalation experience to the user. An embodiment of an overall flow path of gas through the device 601 is depicted via dashed lines in FIG. 21A.

Referring to FIGS. 22A-22D, embodiments of the base 602, and mechanism of attachment of the base 602 to one or more of the atomizer 603 and mouthpiece 604 are described in more detail. As shown in FIGS. 22A-22D, the base 602 comprises a gas flow path conduit 6200 therein, the gas flow path conduit 6200 comprising a conduit inlet 6201*a* and a conduit outlet 6201*b*, an embodiment of which may also be viewed with respect to FIG. 23. The conduit inlet 6201*a* receives gas exhausted from the atomizer 603, and provides a flow of gas to the mouthpiece 604. In one embodiment, one or more airtight seals are formed between the base 602 and/or the atomizer 603 and mouthpiece 604, so as to create an airtight gas flow path between from the atomizer, through the gas flow path conduit 6200 in the base 602, and to the mouthpiece 604. In the embodiment as shown, the gas flow conduit 6200 in the base separates an atomizer internal gas flow path from a mouthpiece internal flow path.

According to one embodiment, the atomizer 603 and/or mouthpiece 604 are removably attachable to the base 602 via a fastening feature 6202 that allows for repeated removal and re-insertion of the atomizer 603 and/or mouthpiece 604 into the base. In one embodiment, the fastening feature 6202 may be located on the base 602, and/or the fastening feature 6202 may be located on one or more of the atomizer 603 and mouthpiece, and/or the components may have mutually complementary fastening features that allow for repeatable removal and re-attachment of the atomizer 603 and/or mouthpiece 604 to the base 602.

Figure 22A:
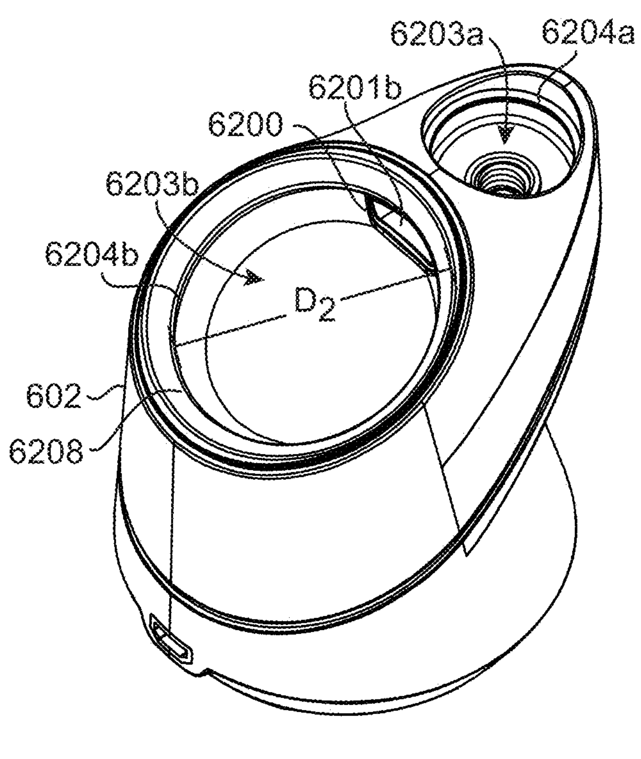

In the embodiment as shown in FIGS. 22A-22D, the base 602 comprises first and second recessed regions 6203*a* and 6203*b*, comprising cavities formed in the base 602 that are configured to receive at least a portion of the atomizer 603 and mouthpiece therein. For example, the base can comprise a first recessed region 6203*a* configured to receive at least a portion of the atomizer 603 therein, and a second recessed region 6203*b* configured to receive at least a portion of the mouthpiece 604 therein. In one embodiment, the fastening feature 6202 is provided as part of the base, and can comprise one or more airtight sealing members 6204*a*, 6204*b* located in the base, such as a first airtight sealing member 6204*a* provided in the first recessed region to retain the atomizer therein, and/or a second airtight sealing member 6204*b* provided in the second recessed region to retain the mouthpiece 604 therein. In yet another embodiment, the fastening feature 6202 may be provided on the atomizer and/or mouthpiece. For example, the mouthpiece 604 may comprise a snap region 6401 that is configured to be received by the second recessed region of the base, and that comprises a fastening feature 6202 thereon to retain the step region in the base. In one embodiment, the fastening feature that removably retains one or more of the atomizer and/or mouthpiece in their respective recessed region is also capable of providing an airtight seal between the base and atomizer and/or mouthpiece. In the embodiment as shown in FIG. 22B, an airtight sealing member 6204*c* can be provided about the gas conduit outlet 6201*b* to provide an airtight connection to the mouthpiece inlet.

Figure 23:
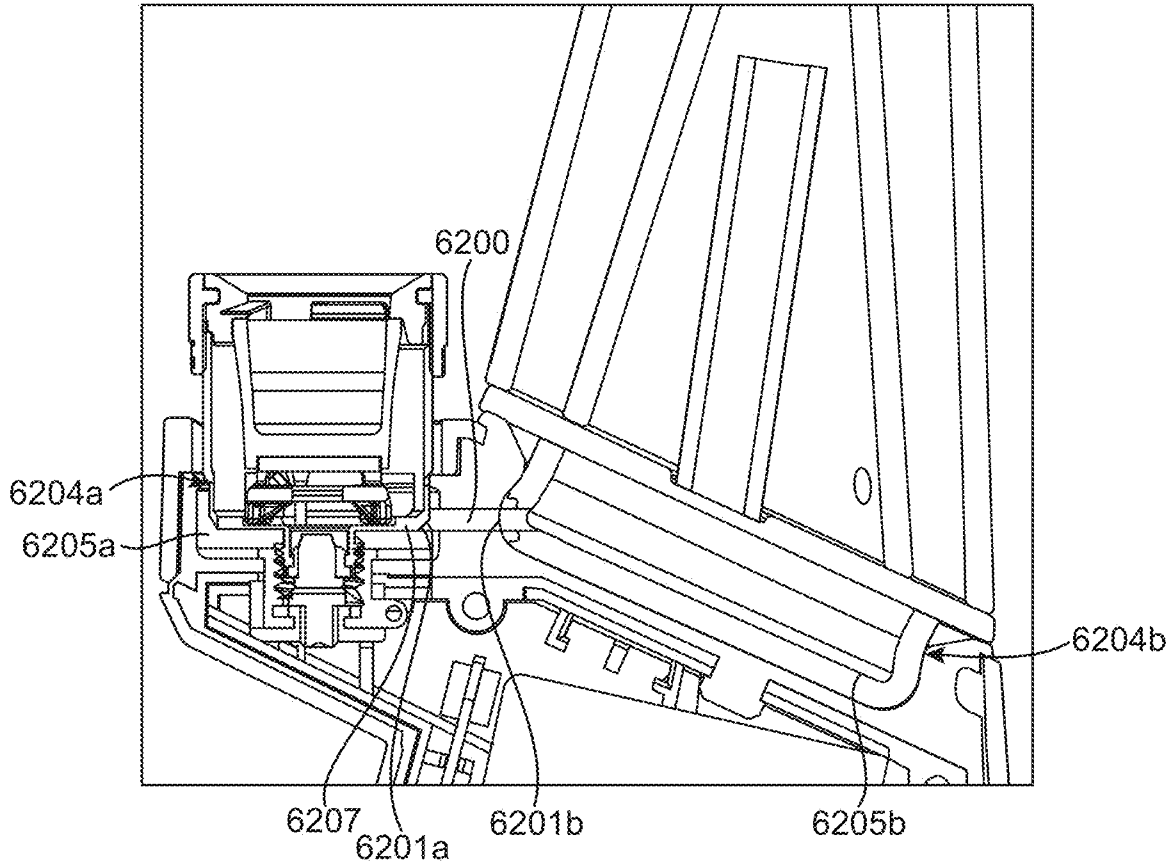
FIG. 23 shows a close-up schematic view of the device of FIG. 19.

In one embodiment, the base 602 is capable of forming a first airtight compartment 6205*a* via airtight seal with the atomizer, and/or is capable of forming a second airtight compartment 6205*b* via an airtight seal with the mouthpiece 604, as shown in FIG. 23. In one embodiment, the base comprises a first recessed receiving region 6203*a* formed therein that is configured to receive the atomizer 603, the first recessed receiving region 6203*a* comprising an annular sealing region 6204*a* provided about an internal circumference 6206*a* of the first recessed receiving region, to form the airtight compartment between the base and atomizer in the portion of the first recessed region below the annular sealing region. In another embodiment, the base comprises a second recessed receiving region 6203*b* formed therein that is configured to receive the mouthpiece, the second recessed receiving region 6203*b* comprising an annular sealing region 6204*b* provided about an internal circumference 6206*b* of the second recessed receiving region, to form the airtight compartment between the base and mouthpiece in the portion of the second recessed region below the annular sealing region.

In one embodiment, an annular sealing region provided about a recessed cavity in the base, and/or about a circumference of the atomizer and/or mouthpiece, comprises an elastomeric, rubber and/or silicone material. In another embodiment, the base 602 comprises one or more elastomeric, rubber and/or silicone sleeves 6208 conformally lining one or more recessed regions 6203*a*, 6203*b*, and/or the conduit 6200. In one embodiment, the sleeve 6208 may be a single sleeve piece lining at least a portion of the recessed regions 6203*a*, 6203*b* and conduit. According to yet another embodiment, at least one of the atomizer and mouthpiece can comprise an elastomeric, rubber and/or silicone sleeve conformally lining at least a part of a surface thereof that is received by first and/or second recessed regions of the base. In yet another embodiment, the sleeve 6208 provided in one or more of the recessed regions 6203*a*, 6203*b* comprises one or more annular protrusions extending therefrom, such as by molding of the sleeve material to form the protrusions, which can serve as airtight sealing members 6204*a*, 6204*b* between the base and atomizer and/or mouthpiece.

In one embodiment, the base 602 comprises a second recessed receiving region 6203*b* formed therein that is configured to receive the snap region 6401 of the mouthpiece 604, the second recessed receiving region comprising the annular sealing region 6204*b* provided about an internal circumference thereof, to form an airtight compartment between the base and snap region of the mouthpiece in the portion of the second recessed region below the annular sealing region. In yet another embodiment, the second recessed receiving region further comprises the annular sealing region 6204*c* about the conduit outlet 6201*b* to form an airtight seal between the conduit outlet 6204*c* and a mouthpiece inlet 6402. In one embodiment, the gas flow path conduit outlet 6201*b* in the base is located below the annular sealing region 6204*b* in the second recessed region, such that an interface between the gas flow path conduit outlet in the base, and the mouthpiece inlet is located in an airtight compartment portion of the second recessed receiving region. In one embodiment, the annular sealing region 6204*b*, 6204*c* comprises at least one of a rubber, elastomeric, and a silicone material.

As described above, in one embodiment the base 602 comprises a housing 6209 that is configured to house a power source 6210 for powering a heating device such as a heating element 608 in the atomizer 603, and optionally comprises one or more control elements for operating components of the device 601. For example, in one embodiment the power source 6210 can comprise a rechargeable battery, such as a lithium-ion battery. The housing may also contain outlets to connect the device with an electrical outlet and/or other devices, and may house control elements such as Central Processing Units ("CPUs") and/or wireless transmitters for controlling heating and vapor production with the device, either via direct or wireless input into the device by a user.

Referring to FIGS. 24A-24C and 25-29, an embodiment of an atomizer 603 is described. In the embodiment as shown, the atomizer 603 is removably attachable to the base, an includes an atomizer inlet 6301 configured to receive a flow of gas into the atomizer 603, and an atomizer housing 610 comprising one or more atomizer housing walls 6304 that at least partially define an atomizer internal flow path therein. The atomizer 603 is further configured to contain a container 607 (e.g., a bowl) within the atomizer housing 610 that is capable of holding a vaporizable product therein. According to certain embodiments, the container 607 comprises the container 402*a* comprising one or more resistive heating elements embedded therein (as shown in FIG. 21B), and that are capable of heating the vaporizable product held in the container 607. According to the embodiment as showing, the atomizer comprises a first container inlet 6305 capable of introducing gas into the container 607 to entrain vaporizable product therein, and comprises one or more second container outlets 6306 capable of flowing the gas having the vaporizable product entrained therein into an atomizer internal flow path 6308. Embodiments of the atomizer 603 comprise one or more atomizer outlets 6309 capable of receiving the flow of gas from the atomizer internal flow path 6308, and providing the flow of gas to the conduit inlet 6201*a* of the base 602.

Figure 24A:
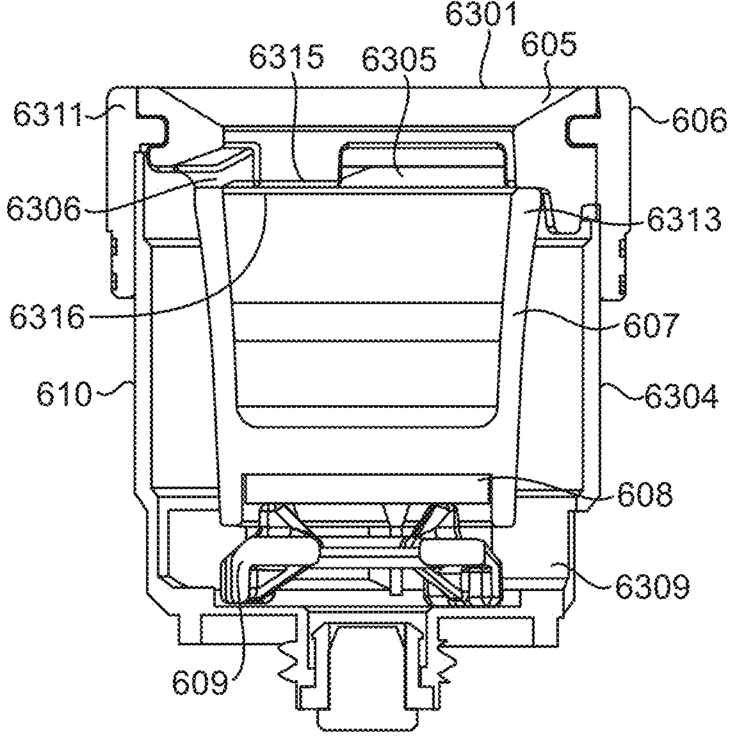
FIGS. 24A-24B show schematic views of embodiments of an atomizer.

In one embodiment, the container 607 comprises the heating device 409 comprising one or more embedded resistive heating elements as described elsewhere herein (as shown, e.g. in FIG. 21B), and the heating device 409 may be attached to conductive elements such as wires leading to the power source (e.g. battery) to provide an applied voltage for the resistive heating. The container 607 comprising the heating device 409 can be provided as an alternative to, or optionally in addition to, a heating element 608 such as a heating plate. According to yet another embodiment, the atomizer 603 comprises a bottom insulating element 609 comprising a spacer disposed between the heating element 608 and atomizer housing 610 that thermally insulates the heating element 608 from the atomizer housing 610. According to another embodiment, the atomizer 603 comprise a top insulating element 6311 that thermally insulates a top end 6313 of the container 607 from the atomizer housing 610. In one embodiment, the top insulating element 6311 is configured to receive a cap 617 thereon. For example in one embodiment, the device 601 is configured to operate with a cap 617 (FIG. 24B) positioned upstream of the atomizer 603, the cap comprising a stopper having a conduit 6314 formed therein to provide a flow of ambient air into the atomizer 603. In one embodiment, the container 607 is thermally insulated from the atomizer housing 610 by both the bottom insulating element 609 that positions the container within the housing at a bottom end of the container, and the top insulating element 6311 that positions a top end of the container in the housing. In one embodiment, referring to FIG. 24C, the top insulating element 6311 comprises inner and outer annular insulating rings 605, 606. In one embodiment, an inner circumference of the inner annular insulating ring 605 defines the atomizer inlet 6301, and is in communication with the first inlet 6305 of the container 607. In the embodiment as shown in FIG. 24A, the atomizer inlet 6301 is directly above the first inlet 6305, and/or the atomizer inlet 6301 and first container inlet may comprise the same inlet. That is, in one embodiment, the atomizer inlet may be aligned with and lead to a container inlet positioned below the inner annular ring 605 of the top insulating element 6311.

In one embodiment, the atomizer 603 comprises an outer annular ring 606 that forms an annular jacket that is flush with the outer surface of the inner annular ring 605, and extends in an axial direction beyond the inner annular ring such that a portion of the interior surface of the outer annular ring is in contact with an outer surface of the atomizer housing 610. In one embodiment, the outer annular ring 606 may secure the inner annular ring 605 to the atomizer housing 610 via frictional forces and/or via a snap mechanism or other fastening mechanism between a portion of the interior surface of the outer annular ring and the outer surface of the atomizer housing. In one embodiment, the outer annular ring comprises an annular jacket that forms an airtight seal with the atomizer housing.

In one embodiment, one or more of the inner and outer annular rings 605, 606 are capable of thermally isolating the container 607 from the atomizer housing 610, by having a lower thermal conductivity. For example, one or more of the inner and outer annular insulating rings can comprise a thermal conductivity of less than 4 W/mk, less than 3.5 W/mk and/or less than 3 W/mk, whereas the container may comprise a thermal conductivity of at least 10 W/mk, at least 15 w/mk and/or at least 20 W/mk. In one embodiment, a bottom surface 6315 of the inner annular insulating ring 605 is in contact with an upper surface 6316 of the container 607.

In one embodiment, one or more of the container 607 and/or thermally insulating element 6311, such as the inner annular ring 605, comprise one or more apertures 6318 therein that correspond to the one or more container second outlets 6306. For example, in one embodiment the inner annular ring 605 comprises one or more indentations 6320 formed in the bottom surface 6315 thereof, such as about a circumference thereof, which form one or more apertures 6318 between the bottom surface 6315 of the inner annular ring 605 and the top surface 6316 of the container 607. In yet another embodiment, the inner annular ring 605 comprises one or more apertures formed in the body thereof, such as about a circumference thereof, to provide the one or more container outlets. In yet another embodiment, the container itself comprises one or more apertures 6318 formed in one or more walls thereof, wherein the one or more apertures comprise the one or more second container outlets 6306. According to certain embodiments, first container inlet 6305 introduces a gas flow received through the inner insulating annular ring 605 into the container 607, and the one or more second container outlets 6306 flow gas out of the container through the one or more apertures 6318. The second container outlets 6306 may thus be a separate aperture and/or opening than the first container inlet 6305, such that air comes through the inlet and passes through a separate outlet when exiting the container 607.

Furthermore, in one embodiment, the top insulating element 6311 is removable from the atomizer housing 610 to allow access to the container 607. For example, the insulating element 6311 may be removable by simply lifting or twisting the top insulating element form the atomizer housing 610. According to yet another embodiment, the atomizer housing 610 comprises a lower portion 6322 that is threaded, and that may be complementary to a threaded socket in the first recessed region 6203*a* of the base 602, so the atomizer can be screwed into the threaded socket of the base. In yet another embodiment a lower portion of the atomizer housing may connects to the base via a magnet, span mechanism or other fastening feature.

Figure 24B:
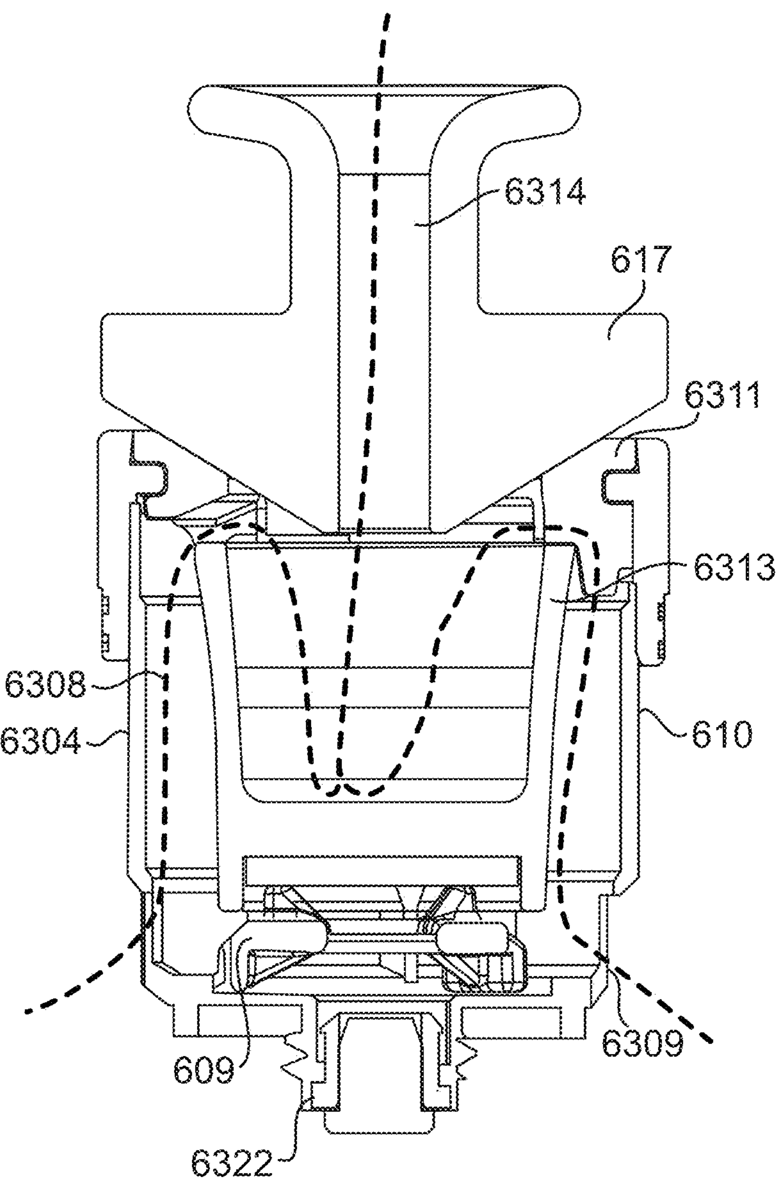
Figure 24C:
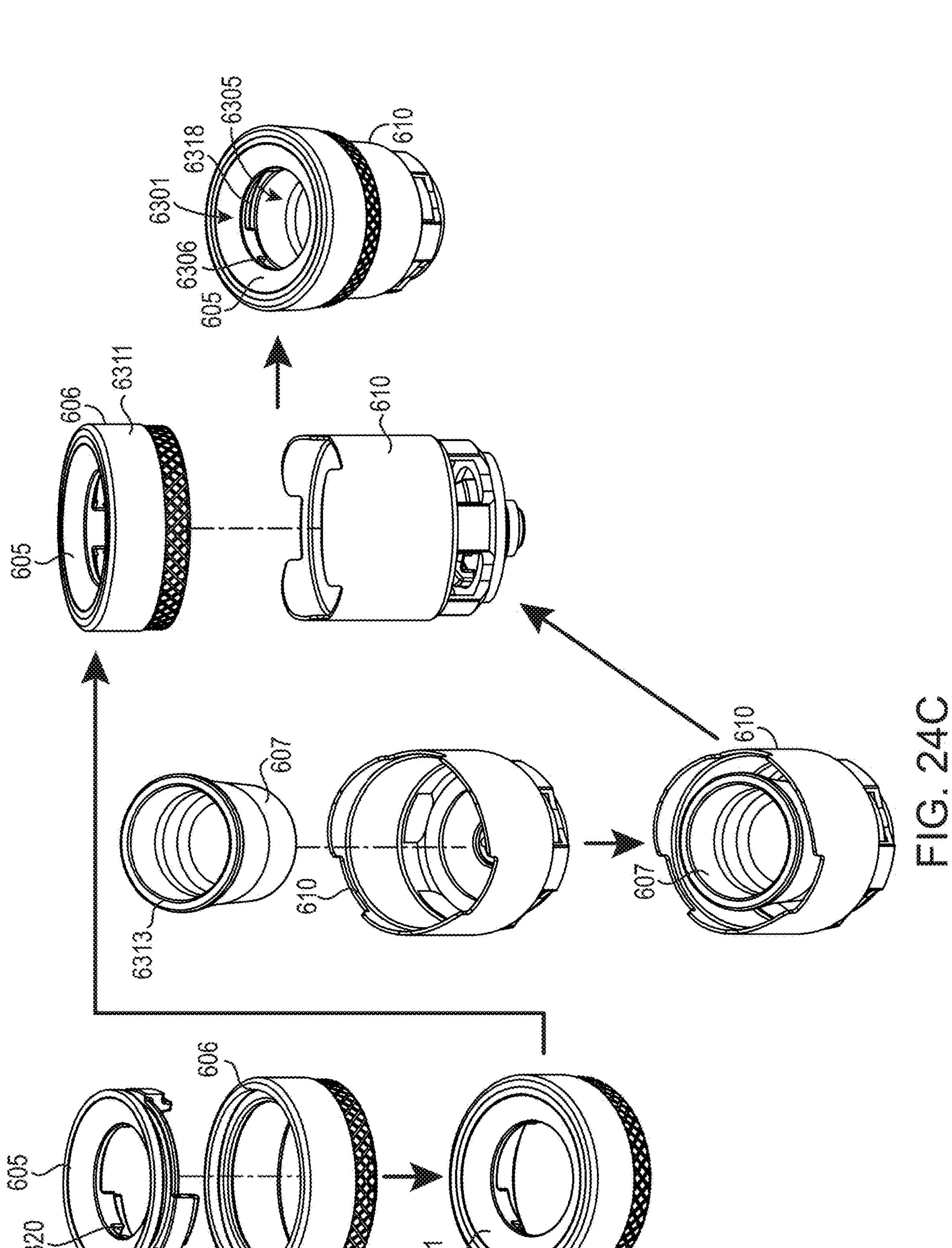
FIG. 24C shows various perspective views of embodiments of an atomizer.
Figure 25:
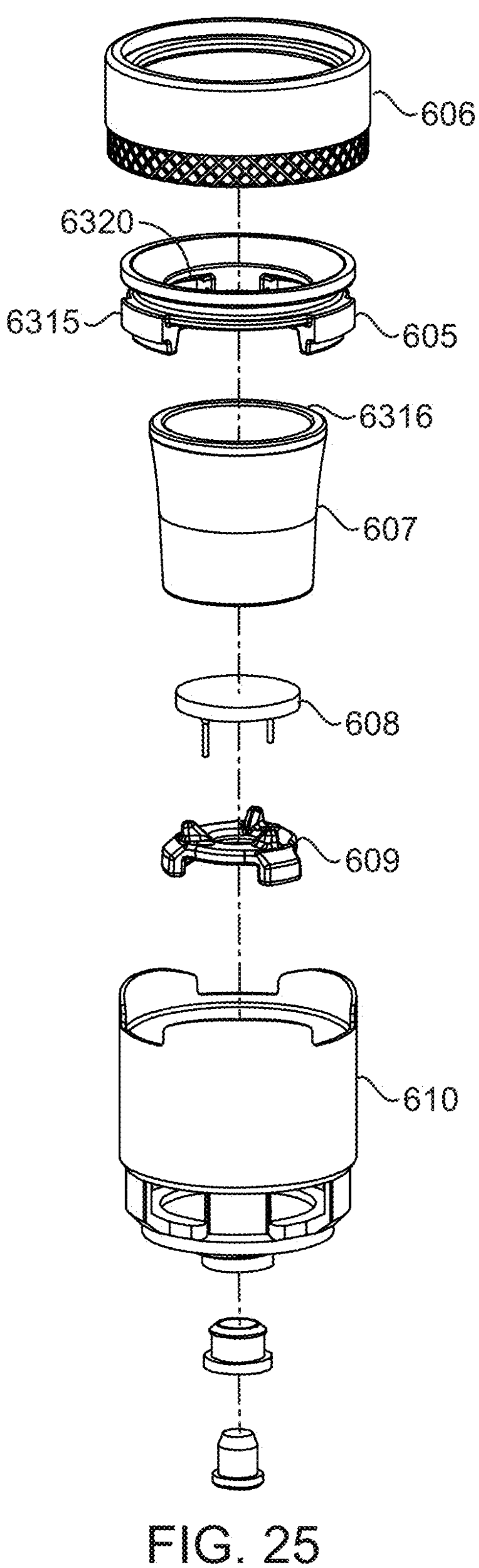
FIG. 25 shows an exploded view of an embodiment of components of an atomizer.
Figure 26:
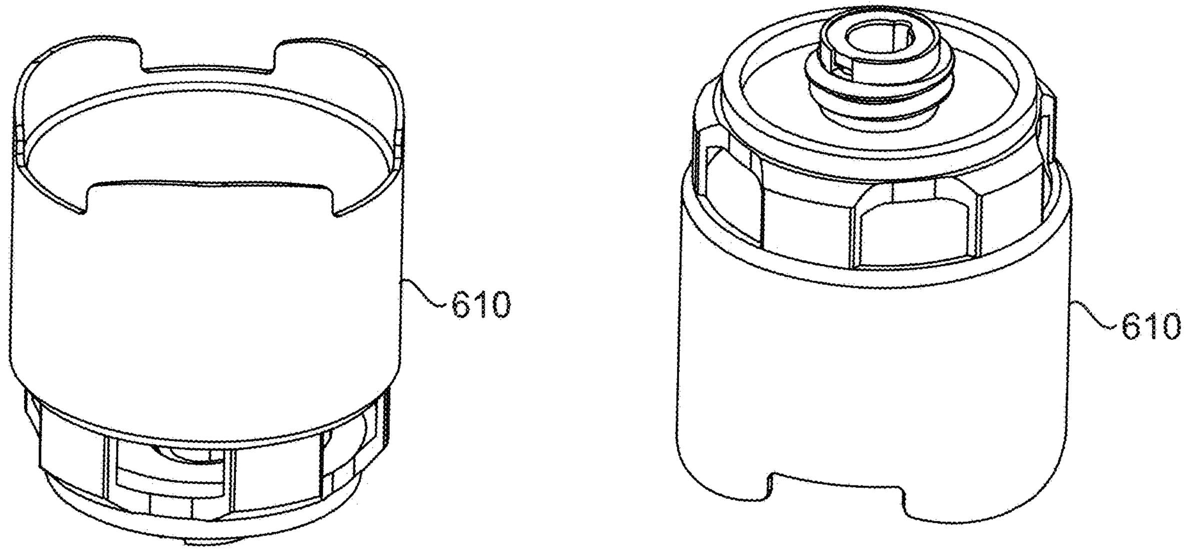
FIGS. 26-29 show various perspective views of embodiments of components of an atomizer.
Figure 27:
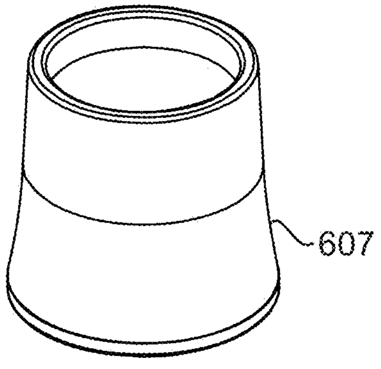
Figure 28:
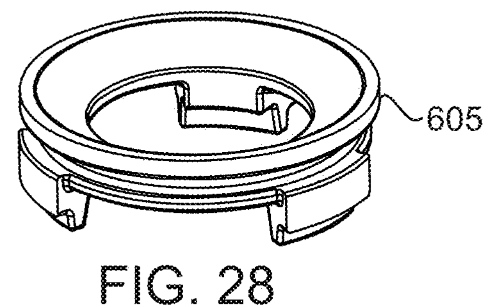
Figure 29:
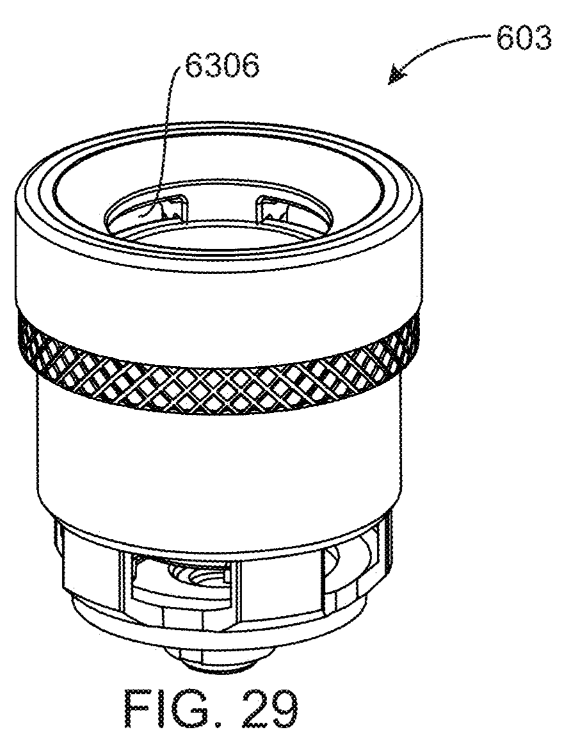
Figure 30:
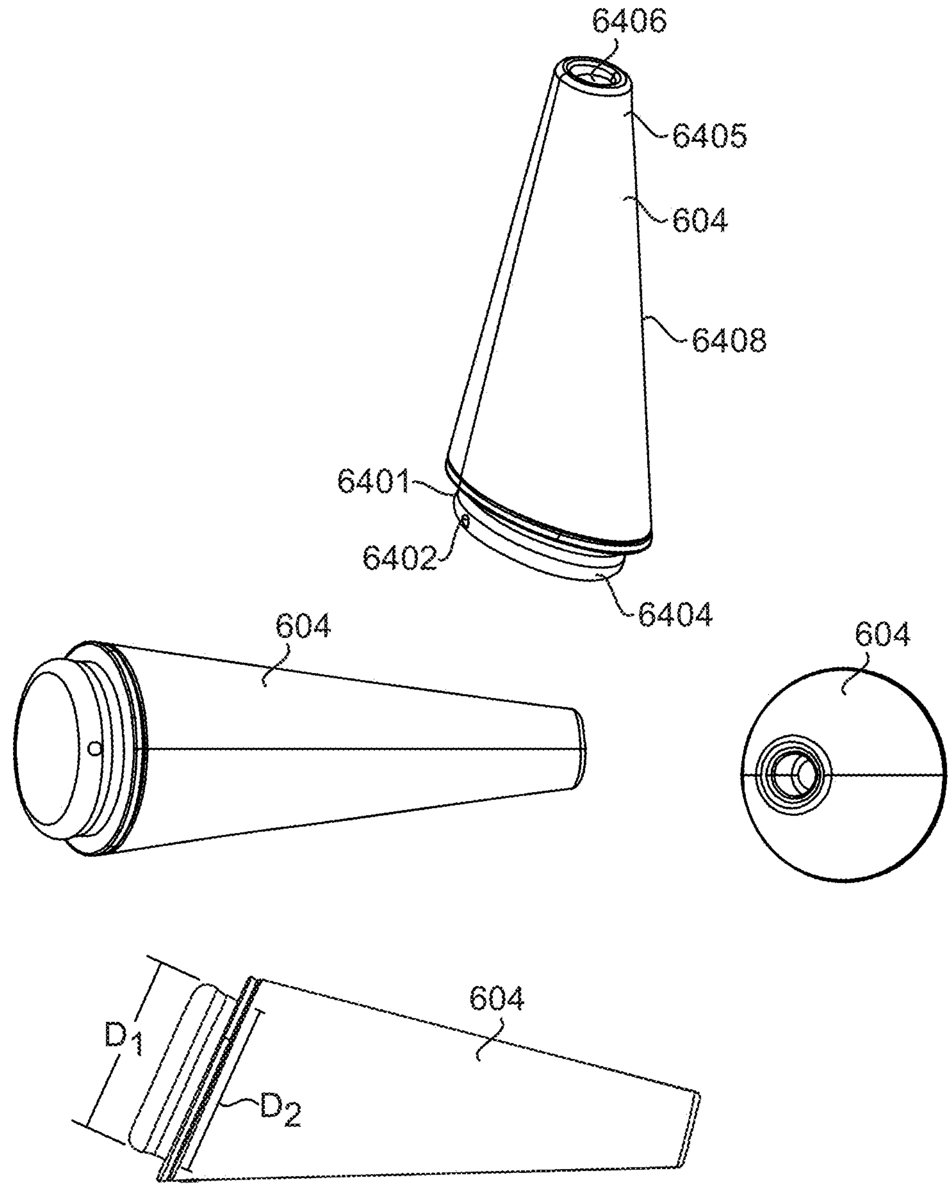
FIG. 30 shows various views of embodiments of a mouthpiece.

According to one embodiment, atomizer housing at least partially direct gas from the one or more second container gas outlets 6306 along the internal atomizer gas flow path 6308 (shown as a dashed line in FIG. 24B), in a passage 6324 formed between walls of the container 7 and the atomizer housing 610. The atomizer housing 610 can comprises one or more apertures/outlets 6309 formed therein to flow gas from the internal atomizer gas flow path 6308 to the airtight passage 6207 that is external to the atomizer housing in the first recessed region 6203*a* of the base 602. In one embodiment, the atomizer housing apertures/outlets 6309 are located at a lower end of the atomizer housing, and the atomizer housing 610 redirects flow of the gas from the one or more second container gas outlets 6306 in a downward direction along a passage 6324 formed between the housing walls and container walls, to the atomizer housing apertures/outlets 6309. As shown in FIG. 24B, in one embodiment a flow of gas through the atomizer 608 comprises a flow through the first container inlet into a top of the container, flow out of the container through second container outlets that are separate from the inlet, and that are towards a top 6313 of the container, flow downward between the atomizer housing and container wall towards a bottom of the atomizer and through apertures of the atomizer towards the bottom of the atomizer housing.

In one embodiment, the one or more second container outlets 6306 are located radially externally to the first container inlet 6305, and/or are positioned in an arrangement circumferentially surrounding the first container inlet 6305. The second container outlets 6306 may also be located towards a top end of the atomizer and/or container. In a further embodiment, the apertures and/or outlets 6309 for exhausting gas from the atomizer are located below the first container inlet and/or second container outlet, towards a lower end of the atomizer.

In one embodiment, the container 607 may be secured and insulated by the bottom insulating element 609 and top insulating element 6311 respectively, with these two elements firmly locating the container 607 within the atomizer (while heating element 608 is shown in the figures, alternatively the container 607 may comprise the heating device 409 used to heat the vaporizable product, without providing a separate heating element 608 outside the container 607). These two elements are made with low thermally conductive, yet high heat withstanding, material so that minimal heat is lost from the heating element and container. The top insulating element comprises an outer annular ring comprising sleeve 606, made of an insulating material, like silicone or plastic. The sleeve 606 fastens to the housing 610 and makes an airtight seal while the inner annular ring 605 insulates and positions the container 607. The sleeve 606 may also protect the user from heat and serves as a grip for screwing and unscrewing the atomizer.

According to certain embodiments, air may enter the top of the container through a cap 617. The cap 617 may be capable of directing high velocity air to the bottom of the container, where the material is vaporized. Air then exits the top of the container as vapor through the second outlets which are apertures in the inner annular ring 605 above the container. These slots/apertures could also be cut into the top of the container. The vapor travels through the slots in the inner annular ring and down a gap formed between the container and the atomizer housing. The vapor can leaves the bottom of the atomizer and travels through an airpath into the mouthpiece. FIG. 24B shows a cross-sectional view of the assembled atomizer with the cap and illustrates the airflow through the atomizer, entering through the cap and exiting out of the bottom of the atomizer.

Referring to FIGS. 19-20, 21A, 23 and 30, embodiments of the mouthpiece 604 are further described. In one embodiment, the mouthpiece 604 is removably attachable to the base 602. The mouthpiece can generally comprise a mouthpiece housing 6408, comprising one or more mouthpiece walls 6410 at least partly defining a mouthpiece internal flow path 6412 through the mouthpiece housing (e.g., as shown in FIG. 21A). The mouthpiece can further comprises the inhalation outlet 6406 formed in a region of the one or more mouthpiece walls 6410, such as towards a top end 6405 of the mouthpiece 604. The mouthpiece can further comprise at least one mouthpiece inlet 6402 capable of being placed in communication with the conduit outlet 6201*b* of the base 602 upon attachment of the mouthpiece 604 to the base 602, to receive a flow of gas into the mouthpiece 604 from the base 602. In some embodiments a gas flowed through the mouthpiece from the mouthpiece inlet 6402 to the inhalation outlet 6406, may take a convoluted path through the interior volume of the mouthpiece and along the internal flow path, such as for example when a water filtering region is provided as part of the mouthpiece.

In one embodiment, the mouthpiece comprises a snap region 6401 that is configured to removably attach the mouthpiece to the base. For example, in one embodiment, the base can comprises the second recessed receiving region 6203*b* for receiving the mouthpiece therein via the snap region 6401, which may be shaped and sized to fit within the second recessed receiving region. The snap region 6401 may be located at the bottom end 6404 of the mouthpiece, an in certain embodiments the mouthpiece inlet 6402 may located in the snap region 6401, of the mouthpiece. In one embodiment, the second receiving region 6203*b* may be at least partially lined with a rubber, silicone, and/or elastomeric sleeve to conformally mate the second recessed region with the snap region of the mouthpiece.

In yet another embodiment, the mouthpiece comprises one or more a water filtering regions 6414*a*, 6414*b*, capable of holding a volume of water therein, the water filtering region being located along the mouthpiece internal flow path, such that water vapor becomes entrained into gas passing through water in the water filtering region. In the embodiment as shown in FIG. 21A, a volume of water can be provided to partly fill in internal volume of the mouthpiece volume along a lower region of the internal mouthpiece volume.

In one embodiment, the at least one mouthpiece inlet 6402 is located towards a bottom region 6404 of the mouthpiece housing 6408, and the inhalation outlet 6406 is located distal to the at least one mouthpiece inlet 6402 at an upper region 6405 of the mouthpiece housing. According to yet another embodiment, the mouthpiece 604 comprises a plurality of chambers 6416*a*, 6416*b* that are connected to one another along the mouthpiece internal flow path 6412. For example, the mouthpiece can comprise a first chamber 6416*a* that is internal to a second chamber 6416*b*, and wherein a flow of gas along the mouthpiece internal flow path 6412 passes through the first chamber and into the second chamber. In one embodiment, the second chamber at least partially circumferentially surrounds the first chamber. In one embodiment, the mouthpiece comprises one or more internal walls 6418 defining the first chamber 6416*a*, and wherein the second chamber 6416*b* is defined between the one or more internal walls 6418 and the mouthpiece housing 6408. In one embodiment, lower portions of the first and second chambers 6416*a*, 6416*b* comprise water filtering regions configured to receive and hold water therein. Furthermore, in one embodiment, the first and second chamber are connected to each other by at least one port 6420 formed in the one or more internal walls 6418.

In the embodiment as shown in FIG. 21A, the first chamber 6416*a* comprises a first chamber inlet 6422 that is positioned above the at least one port 6420 formed in the one or more internal walls, which port may be located at or below a level of water in the chambers when water is provided in the mouthpiece. In one embodiment, a flow of gas exiting the first chamber inlet 6422 is directed by the one or more internal walls 6418 towards the water filtering region in a lower portion of the first chamber 6416*a*, and the gas exits the water filtering region in the lower portion of the first chamber 6416*a* through the one or more ports 6420 to enter a water filtering region of a lower portion of the second chamber 6461*b*, and wherein gas having water vapor therein exits the water filtering region of the lower portion of the second chamber and is directed by the passage formed between the housing walls 6410 and internal walls 6418 to be output from the mouthpiece via the inhalation outlet. In the embodiment as shown in FIG. 21A, the first chamber inlet 6422 is at the end of a tube 6424 extending upwardly into the first chamber 6416*a*, the tube comprising an aperture to receive gas from the mouthpiece inlet, and wherein the first chamber inlet is located at a location that is higher than the port connecting the chambers. In another embodiment, the one or more internal walls 6418 comprise a conically-shaped internal wall, and the mouthpiece housing comprises a conical housing wall about the conically-shaped internal wall.

In one embodiment, a method of using a portable electronic vaporizing device 1 as described according to any of the embodiments herein, can comprise loading vaporizable product into the container 402*a*, optionally at least partially filling the mouthpiece with water in water filter regions thereof, activating the heating device and/or heating element to at least partially vaporize the product in the container, and inhaling gas exiting the mouthpiece outlet, the gas comprising ambient air having vaporized product and water vapor entrained therein.

According to still another aspect of the invention, a portable vaporizing device comprising the refillable container disclosed herein and methods of using such container and device are provided. In one embodiment, the method comprises providing vaporizable product to the container, activating the heating device to heat the vaporizable product in the container to at least partly vaporize the product; and inhaling gas entrained with the vaporized product via the portable vaporizing device. In one embodiment, the vaporizable product is provided to the container to fill up the refillable container to a height of no more than $H_D$, such that the height of the vaporizable product in the container does not exceed the height of sidewall heating portions of the container.

According to a further aspect of the invention, a vaporization assembly and an atomizer comprising the container disclosed herein are also provided. In one embodiment, a vaporization assembly for an electronic vaporizing device disclosed herein is provided. The vaporization assembly comprises: a vaporization assembly housing; the container 402*a* disclosed herein and having one or more embedded resistive heating elements, the container being configured to receive a vaporizable product within the vaporization assembly housing, the container including the heating device configured to be electrically connected to the battery and transfer energy to the vaporizable product in the container to heat the product and form a vapor therefrom; an inlet configured to introduce gas into the container; one or more container outlets configured to receive a flow of gas having vaporized product entrained therein from the refillable container; and one or more vaporization assembly outlets configured to output the flow of gas received from the container outlets, wherein during use of the vaporization assembly in the electronic vaporizing device, the flow of gas output by the one or more vaporization assembly outlets is received by a mouthpiece of the electronic vaporizing device.

In another embodiment, a removably attachable atomizer for an electronic vaporizing device is provided. The atomizer comprises: an atomizer inlet configured to receive a flow of gas into the atomizer; an atomizer housing comprising one or more atomizer housing walls that at least partially define an atomizer internal flow path therein; the container 402*a* disclosed herein within the atomizer housing that is capable of holding a vaporizable product, the container comprising the heating device having the one or more embedded resistive heating elements capable of heating the vaporizable product held in the container, the heating device being configured to be electrically connected to a battery and transfer energy to the vaporizable product in the container to heat the product and form a vapor therefrom; a first container inlet capable of introducing gas into the container to entrain vaporizable product; one or more second container outlets capable of flowing the gas having the vaporizable product entrained therein; one or more atomizer outlets capable of receiving the flow of gas from the atomizer internal flow path, and outputting the flow of gas from the atomizer internal flow path, wherein during use of the atomizer in the electronic vaporizing device, the flow of gas output by the one or more atomizer outlets is received by a mouthpiece of the electronic vaporizing device.

According to further embodiments, the container 402*a* comprising the one or more embedded resistive heating elements can be used with any suitable vaporization assembly, atomizer, and or portable electronic vaporizing device, described herein or otherwise suitable for use with the container.

According to a further aspect of the invention, a battery-powered removably attachable vaporization module 2*a* is provided that is configured to attach to and form an air tight seal with a mouthpiece 3, such as for use in the vaporization of a product in a portable electronic vaporizing device 1. For example, the battery-powered removably attachable vaporization module 2*a* may correspond to the removably attachable vaporization module 2 as described with reference to FIGS. 1-3B and 6A-7B above. As described with reference to FIGS. 1-14B above, the mouthpiece 3 comprises a mouthpiece housing 301 at least partly defining an interior chamber, and an inhalation outlet 305 in communication with the interior chamber. The battery-powered removably attachable vaporization module comprises: a vaporization assembly 4 configured to heat a vaporizable product to form a vaporized product therefrom; a base portion 5 comprising a battery storage area 504 in the form of a compartment 504*a* (FIG. 3B) configured to store a battery to power the battery-powered removably attachable vaporization module, the base portion being configured such that the battery storage compartment is received within the interior chamber of the mouthpiece housing when the battery-powered removably attachable vaporization module is attached to the mouthpiece; and wherein, during use of the battery-powered removably attachable vaporization module, gas entrained with vaporized product flows from the vaporization assembly to the interior chamber of the mouthpiece and exits the mouthpiece via the inhalation outlet.

In one embodiment, the battery-powered removably attachable vaporization module comprises the container 402 configured to hold a vaporizable product, and wherein the container is pre-filled with the vaporizable product or is a refillable container. In certain embodiments, the container 402 comprises the container 402*a* described herein comprising one or more embedded resistive heating traces. In one embodiment, the base portion is disposed below the vaporization assembly. In some embodiments, the battery-powered removably attachable vaporization module is configured to be removably attachable to any of a plurality of different mouthpieces with mouthpiece housings having different shapes and sizes.

In one embodiment, the battery-powered removably attachable vaporization module is configured to attach to the mouthpiece housing such that a volume of the base portion containing the battery storage compartment is at least 10%, at least 25%, at least 30%, at least 50%, at least 60%, at least 75%, at least 80%, and/or at least 90% surrounded by the mouthpiece housing when the battery-powered removably attachable vaporization module is attached to the mouthpiece.

In some other embodiments, the battery-powered removably attachable vaporization module is configured to attach to the mouthpiece housing such that the mouthpiece housing extends over a bottom surface 5*b* of the base portion, as well as about one or more sides 5*c* of the base portion. For example, in one embodiment, the module is configured to attach to the mouthpiece housing such that no more than 75%, no more than 60%, no more than 50%, no more than 35%, no more than 25%, no more than 10% and/or no more than 5% of a volume of the battery compartment extends outside mouthpiece housing. In another embodiment, the module is configured to attach to the mouthpiece housing such that no more than 75%, no more than 60%, no more than 50%, no more than 35%, no more than 25%, no more than 10% and/or no more than 5% of a vertical height of the battery compartment extends above a top surface 301*a* of the mouthpiece housing.

In yet some other embodiments, the battery-powered removably attachable vaporization module is configured to attach to the mouthpiece housing such that the battery compartment does not extend outside mouthpiece housing. For example, in one embodiment, the battery-powered removably attachable vaporization module is configured to attach to the mouthpiece housing such that the battery compartment does not extend above a top surface 301*a* of the mouthpiece housing. In another embodiment, the bottom portion comprising the battery storage compartment is configured to be received within the interior chamber of the mouthpiece housing by loading the battery storage compartment into the interior chamber through a mouthpiece module receiving opening 306*a* in the receiving area 306 of the mouthpiece that is located at any of a top of the mouthpiece, a bottom of the mouthpiece, and/or a side of the mouthpiece.

In some embodiments, a space exists between the mouthpiece housing and the battery compartment, where gas is received. For example, in one embodiment, the module is configured to attach to the mouthpiece housing such that, during use of the module, vaporized product is received in the interior chamber 302 at a region that is to the side of the battery compartment. In some embodiments, gas can be received around or below the battery compartment. For example, in one embodiment, the module is configured to attach to the mouthpiece housing such that, during use of the module, vaporized product is received in the interior chamber 302 at a region 302*a* that is below the battery compartment, and/or a region 302*b* that is to the side of the battery compartment. In another embodiment, the module is configured to attach to the mouthpiece housing such that, during use of the module, a flow of vaporized product is directed past a side or beneath the battery compartment within the interior chamber. In a further embodiment, the module is configured to attach to the mouthpiece housing such that surfaces 504*b* of one or more portions of the base portion that are to a side or beneath the battery compartment form a gas flow path in the interior chamber with the mouthpiece housing.

According to embodiments of the present invention, the battery compartment and base portion are designed such that the battery compartment does not extend out of the mouthpiece. For example, in one embodiment, the battery storage compartment is completely received within the mouthpiece housing when the module is attached to the mouthpiece.

In some embodiments, the base portion is releasably attachable to the vaporization assembly. In further embodiments the base portion 5 comprises an attachment region 920 configured to receive the vaporization assembly at an upper region 921 of the base portion.

To seal the battery-powered removably attachable vaporization module to a portable electronic vaporization device, for example, in one embodiment, the module comprises one or more sealing regions 503, such as sealing regions described elsewhere herein, and configured to engage the mouthpiece housing to form the air-tight seal about the interior chamber of the mouthpiece housing when the battery-powered removably attachable vaporization module is attached to the mouthpiece. In certain embodiments, a top surface 401*b* of the vaporization assembly housing 401 is either flush with or extends above the one or more sealing regions 503. In another embodiment, a top surface 401*b* of the vaporization assembly housing 401 is flush with or extends above a top surface 306*a* of the mouthpiece housing 301.

In some embodiments, the battery-powered removably attachable vaporization module disclosed herein comprises the container 402 to receive the vaporizable product, such as the container 402*a* comprising the one or more embedded traces, and wherein the container is flush with or extends above a top surface 306*a* of the mouthpiece housing 301, and/or is flush with or extends above one or more sealing regions 503 of the battery-powered removably attachable vaporization module that engage the mouthpiece housing to form the air-tight seal about the interior chamber of the mouthpiece housing.

According to certain embodiments, in operation, the container 402 (such as container 402*a*) disclosed herein can be accessed for loading/unloading of vaporizable product while maintaining airtight seal. For example, in one embodiment, the vaporization assembly comprises a container configured to receive a vaporizable product within the vaporization assembly housing, and wherein the module is configured to attach to the mouthpiece housing such that the container can be accessed for loading and unloading of the vaporizable product while maintaining the air tight seal between the module and the mouthpiece housing.

In a certain embodiment, the vaporization assembly disclosed herein comprises: a vaporization assembly housing; a refillable container configured to receive a vaporizable product within the vaporization assembly housing; a heating device (e.g. heating device 409 that is provided as a part of container 402) configured to be electrically connected to the battery and transfer energy to the vaporizable product in the refillable container to heat the product and form a vapor therefrom; a refillable container inlet configured to introduce gas into the refillable container; and one or more refillable container outlets configured to receive gas having vaporized product entrained therein from the refillable container.

According to one embodiment, a method of using the battery-powered removably attachable vaporization module comprises attaching the module to the mouthpiece housing to form the air tight seal, loading vaporizable product to the vaporization assembly to generated a vaporized product, and inhaling the vaporized product through the inhalation outlet. According to another embodiment, a method of using the battery-powered removably attachable vaporization module comprises inserting the battery-powered removably attachable vaporization module into a mouthpiece, heating a vaporizable product in the vaporization assembly to form a vaporized product therefrom, and removing the battery-powered removably attachable vaporization module from the mouthpiece. According to yet another embodiment, the mouthpiece comprises a first mouthpiece having a first mouthpiece housing with a first size, shape and/or configuration, and the method further comprises inserting the battery-powered removably attachable vaporization module into a second mouthpiece with a second mouthpiece housing having a size, shape and/or configuration that is different that the first mouthpiece.

EXAMPLES

The following non-limiting examples are provided to further illustrate aspects of the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Vapor Density and Temperature/Power Comparison

Testing was performed to evaluate the performance of a container comprising a heating device comprising heating traces embedded in the lower part of the sidewalls of the container (referred to herein as the “half-trace” container), versus a container having a heating device comprising heating traces extending substantially the full length of the sidewalls (referred to herein as a “full-trace” container). The “half-trace” and “full-trace” containers did not contain heating traces in the bottom of the containers. Testing was performed by providing each of the “half-trace” and “full-trace” containers in a portable vaporization device corresponding to that shown in FIGS. 19-30, and described in U.S. Pat. No. 10,517,334 issued on Dec. 31, 2019 (Ser. No. 16/373,170), which is hereby incorporated herein by reference in its entirety.

Example 1—Targeted Temperature Performance Tests

In this Example, the vapor density as well as time required to reach a targeted temperature, and power required to reach a targeted temperature, when using the “half-trace” versus the “full-trace” containers, were determined. To perform the testing, about 250 mg of vaporizable product concentrate was loaded into the container, and heating of the device was initiated to begin a performance test run. The temperature of the heating device was measured during each run by a resistance temperature detector (RTD) that detects a temperature at a bottom wall of the container and thermal coefficient of resistance detector (TCR) that detects a temperature by detecting a change in resistance of the heater traces themselves, and wattage and resistance of the heating device were also recorded during each run. Vapor density was measured using a sensor that detects an amount of light transmitted through the vapor, to provide a relative measure of the amount of vapor output by the device. Once the TCR detected a temperature of the heating device of around 250° C., an automated system initiated a draw of gas from the mouthpiece of the device, to simulate inhalation by a user, with the draw lasting for 40 seconds at 4 standard liters per minute (slm). Two performance runs were performed, with the heating device being allowed to cool to room temperature between runs.

Figure 15A:
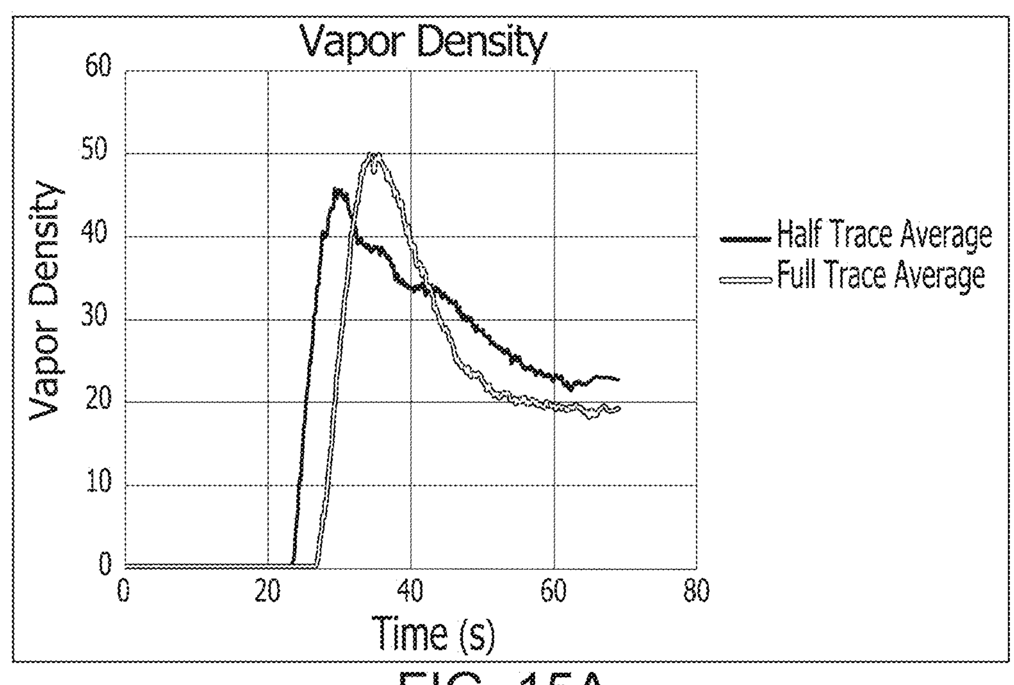
FIGS. 15A-15C and FIGS. 16A-16B show the results of performance testing of a container having embedded heating traces in a lower region of the container sidewalls, versus a container having embedded heating traces extending fully vertically along the sidewalls of the container.

FIG. 15A is a graph showing the average vapor density over time as measured for runs using each of the “full trace” and “half-trace” containers. As can be seen from this figure, the device as run implementing the “half-trace” container surprisingly yielded almost 12% more vapor than the device as run with the “full-trace” container, even though all other operating and device parameters were the same. These results show that the “half-trace” container unexpectedly improves the quantity of vapor generated using a vaporization device over conventional “full-trace” containers, providing for an enhanced user experience with the device. The data for each run is shown in Table 1 below, and the average vapor density different between containers is shown in Table 2.

TABLE 1

| Average Vapor Density | | |
|---|---|---|
| Container | Run 1 | Run 2 |
| Half Trace | 29.3612 | 29.43902 |
| | 28.60644 | 32.6458 |
| Full Trace | 28.27161 | 29.45987 |
| | 24.2469 | 25.36586 |

TABLE 2

| Comparison | | |
|---|---|---|
| Half Trace | Full Trace | % |
| 30.01312 | 26.83606 | 11.84 |

FIG. 15A also shows that the device using the “half-trace” container on average was able to reach the appropriate temperature to initiate the vapor draw nearly 3 seconds faster than when the “full-trace” container was used. Tables 3 and 4 below show the time required to achieve the targeted temperature using the “half-trace” versus the “full-trace” containers (Table 3), and the average difference in time between the “half-trace” and “full-trace” containers (Table 4).

TABLE 3

| Time to Reach Target Temperature (seconds) | | |
|---|---|---|
| Container | Run 1 | Run 2 |
| Half Trace | 21.84585 | 21.51217 |
| | 23.52615 | 22.5228 |
| Full Trace | 25.65726 | 25.65629 |
| | 24.64624 | 24.76225 |

TABLE 4

| Comparison of Time to Reach Target Temperature (seconds) | | |
|---|---|---|
| Half Trace | Full Trace | % |
| 22.35174 | 25.18051 | −11.23 |

Figure 15B:
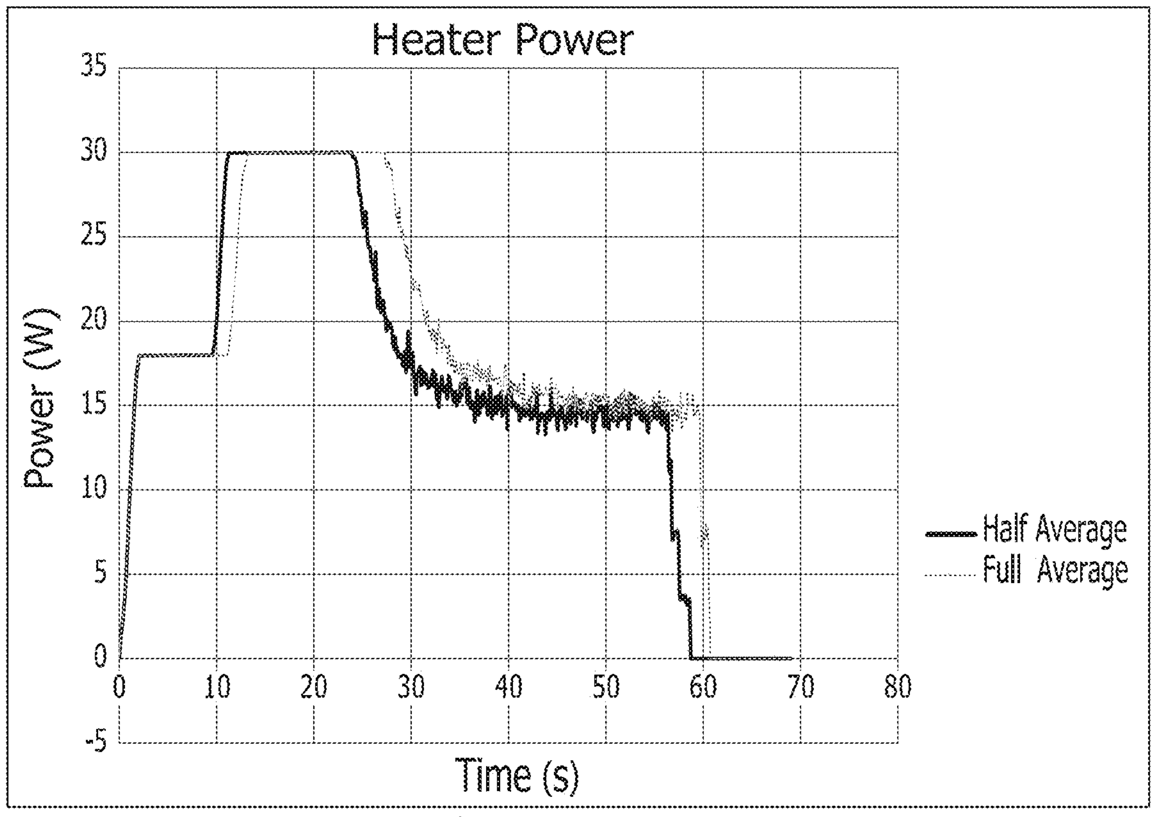

FIG. 15B is a graph showing the power output by the heating device to attain the target temperature as a function of time, and shows that the “half-trace” container required 8% less power on average to reach the same temperature than the “full-trace” container. Tables 5 and 6 below show the average power for each of the “half-trace” and “full-trace” containers for reach performance testing run (Table 5) and a comparison between the containers (Table 6).

TABLE 5

| Average Power (W) | | |
|---|---|---|
| Container | Run 1 | Run 2 |
| Half Trace | 15.83744 | 15.97499 |
| | 16.42337 | 16.41955 |
| Full Trace | 17.58099 | 17.62658 |
| | 17.29671 | 17.77004 |

TABLE 6

| Power Comparison (W) | | |
|---|---|---|
| Half Trace | Full Trace | % |
| 16.16384 | 17.56858 | 8.00 |

Figure 15C:
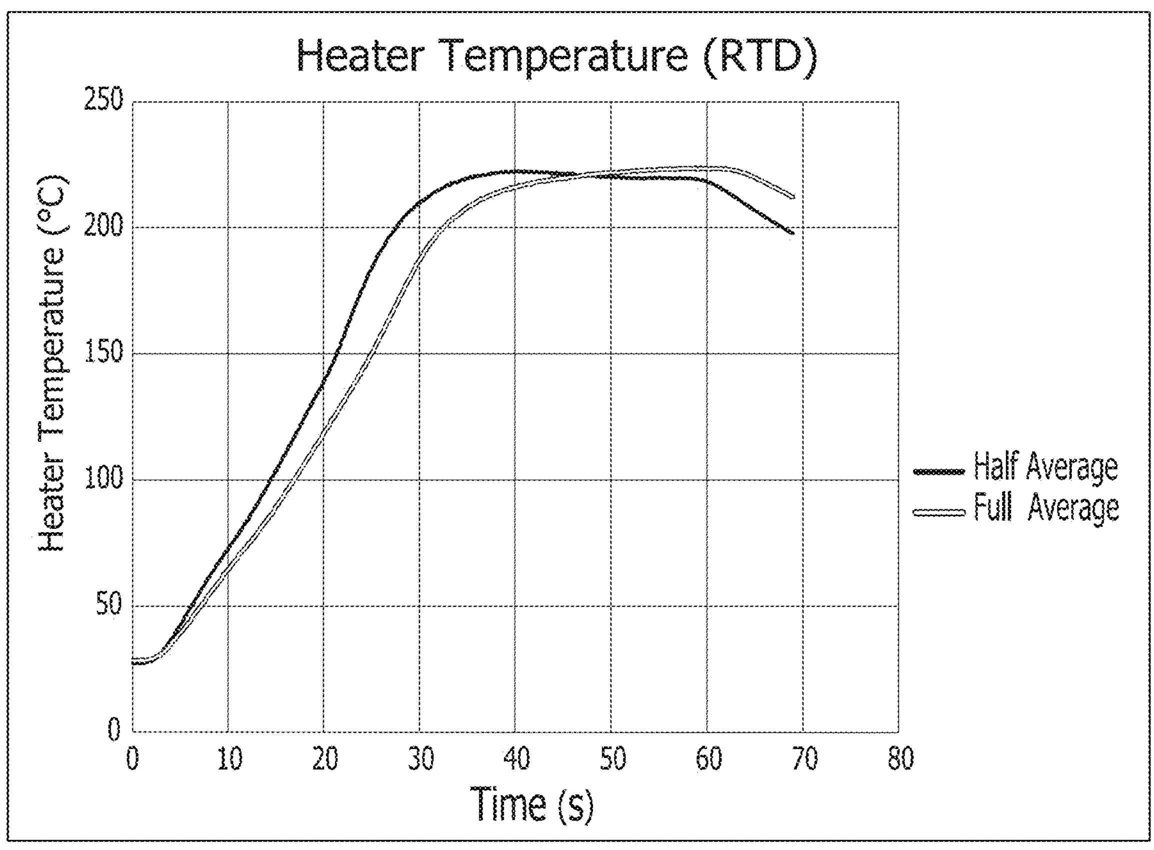

FIG. 15C is a graph showing the average temperature as measured via the RTD, which similarly show that the device using the "half-trace" container is able to achieve the targeted temperature well before the "full-trace" container is able to do so.

Thus, the results surprisingly show that the device with the "half-trace" container not only generates increased levels of vapor during use, but is also capable of reaching a target temperature faster, and with less power, than when the "full-trace" container is used in the device. Half trace chambers are overall more efficient than full trace chambers. They can achieve the same temperature sooner than full trace chambers, achieve the same temperature using less power throughout a cycle, and produce more vapor throughout a cycle.

Example 2—Predetermined Power Cycle Performance Tests

In this Example, "half-trace" and "full-trace" containers as described in Example 1 were tested in the vaporization device and using the general methodology described in that Example. In this example, the vapor density generated for each container when implementing a pre-determined power cycle was measured, along with the temperature of the heating device during the test run (via RTD). The predetermined power cycle used to power the heating device in each container involved initiating heating with 17 W of power applied to the heating device for 10 seconds, followed by 30 W for 15 seconds, 17 W for 50 seconds, and 0 W for 5 seconds. The automated draw of gas from the mouthpiece of the vaporization device was set to initiate at 25 seconds (after onset of the power cycle) and continue for 5 seconds, followed by a halt in the gas draw for 5 seconds, and then repeated for a total of 3 draws (to simulate 3 separate inhalations by a user). Similarly to Example 1 above, to perform the testing, about 200 mg of vaporizable product concentrate was loaded into the container, and heating of the device was initiated to begin a performance test run using the predetermined power cycle. The temperature of the heating device was measured during each run by a RTD and TCR detector, as with Example 1, and wattage and resistance of the heating device were also recorded during each run, along with vapor density. The automated system initiated a draw of gas from the mouthpiece of the device at the time points noted above, as tied to the predetermined power cycle. Two performance runs were performed, with the heating device being allowed to cool to room temperature between runs.

Figure 16A:
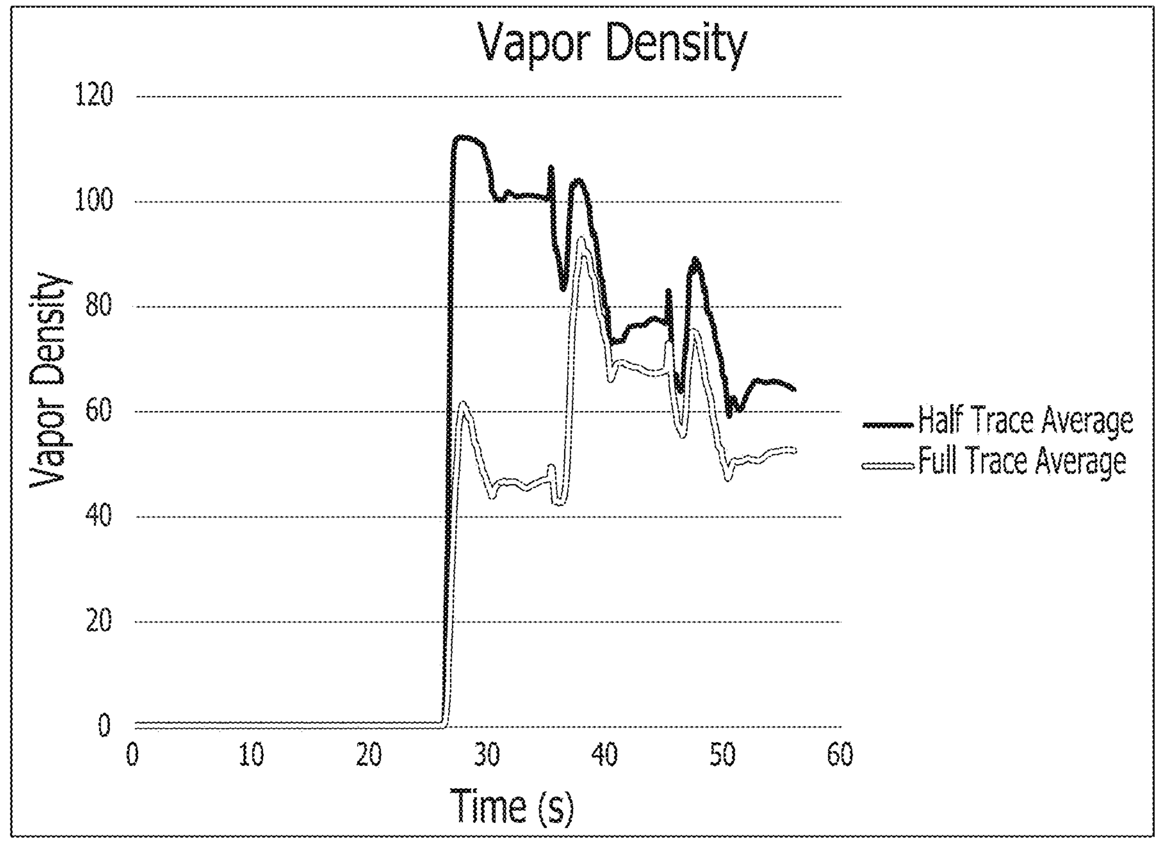

FIG. 16A is a graph showing the average vapor density over time as measured for runs using each of the "full trace" and "half-trace" containers. As can be seen from this figure, the device as run implementing the "half-trace" container surprisingly yielded almost 45% more vapor than the device as run with the "full-trace" container, even though all other operating and device parameters were the same. These results show that the "half-trace" container unexpectedly improves the quantity of vapor generated using a vaporization device over conventional "full-trace" containers, providing for an enhanced user experience with the device. The average vapor density different between containers is shown in Table 7.

TABLE 7

| | Container | Value | % Difference |
|---|---|---|---|
| Vapor Density | Half Trace | 80.68231739 | 45.67 |
| | Full Trace | 55.38820702 | |

Figure 16B:
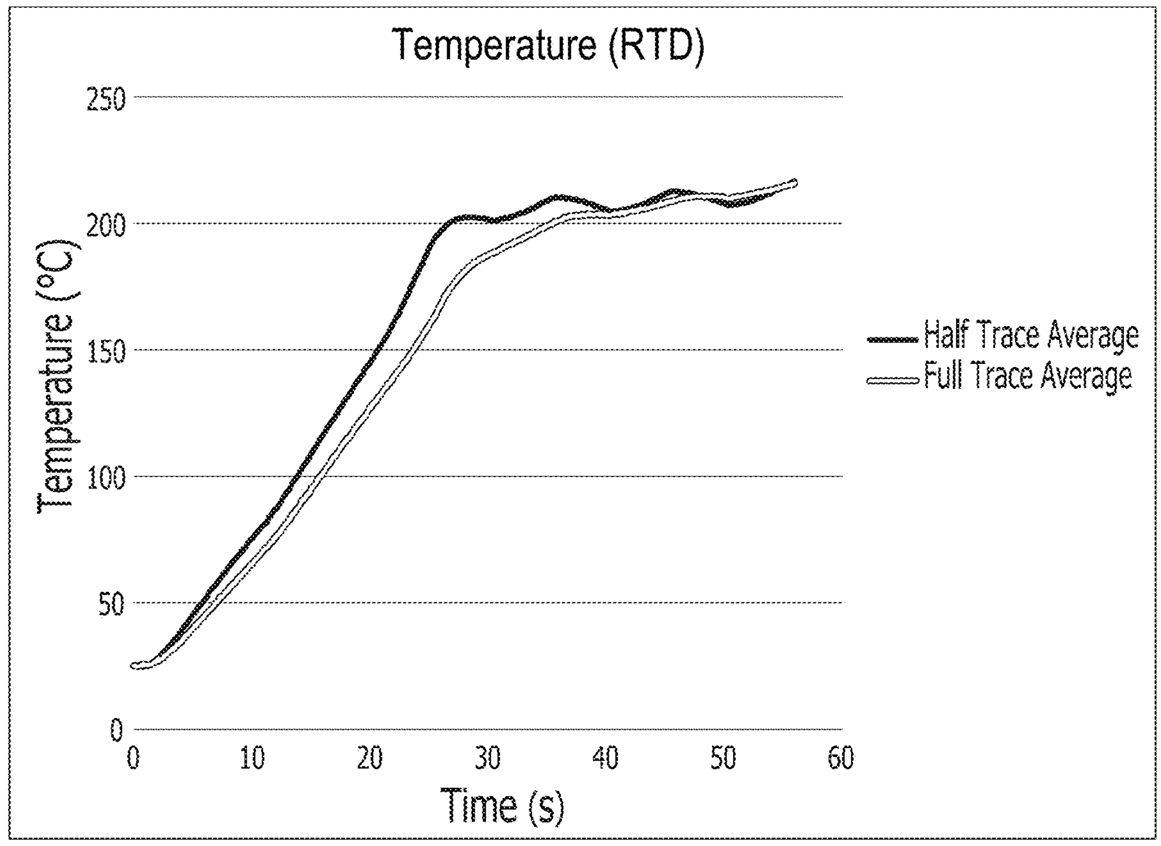

FIG. 16B is a graph showing temperature (as measured by RTD) over time for the "half-trace" and "full-trace" performance tests over the course of the predetermined power cycle. FIG. 16B shows that the device using the "half-trace" container on average was able to heat up an additional 19% under the same power and within the same time as when using the "full-trace" container. Table 8 below shows the average difference in temperature at 25 seconds into the predetermined power cycle, between the "half-trace" and "full-trace" containers.

TABLE 8

| | Container | Value (° C.) | % Difference |
|---|---|---|---|
| Temperature at 25 s | Half Trace | 190.0531464 | 18.97 |
| | Full Trace | 159.7529068 | |

Accordingly, the results show that, even when using the same power inputs to the containers, the "half-trace" containers are capable of significantly outperforming "full-trace" chambers in vapor production and rate of heating.

Example 3—"Half-Trace" Versus "Bottom-Trace" Performance Tests

Testing was performed to evaluate the performance of a container comprising a heating device comprising heating traces embedded in the lower part of the sidewalls of the container (referred to herein as the "half-trace" container) as described above for Examples 1 and 2, versus a container having a heating device comprising heating traces extending substantially the full length of the sidewalls, as well as in a bottom wall of the container (referred to herein as a "bottom-trace" container). Testing was performed by providing each of the "half-trace" and "bottom-trace" containers in a portable vaporization device corresponding to that shown in FIGS. 19-30 herein, and described in U.S. Pat. No. 10,517,334 issued on Dec. 31, 2019 (Ser. No. 16/373,170), which is hereby incorporated herein by reference in its entirety, as described for Examples 1 and 2 above.

In this Example, the vapor density as well as time required to reach a targeted temperature, and power required to reach a targeted temperature, when using the "half-trace" versus the "bottom-trace" containers, were determined. To perform the testing, about 125 mg of vaporizable product concentrate was loaded into the container, and heating of the device was initiated to begin a performance test run. The temperature of the heating device was measured during each run by a RTD and TCR detector, as described for Examples 1 and 2 above, and wattage and resistance of the heating device were also recorded during each run, along with vapor density. Once the TCR detected a target temperature of the heating device of around 250° C., an automated system initiated a draw of gas from the mouthpiece of the device, to simulate inhalation by a user, with the draw lasting for 5 seconds at 4.5-5 slm, followed by 5 seconds with no draw, and repeated 4 times to simulate 4 inhalations by a user. Three performance runs were performed, with the heating device being allowed to cool to room temperature between runs.

Figure 17:
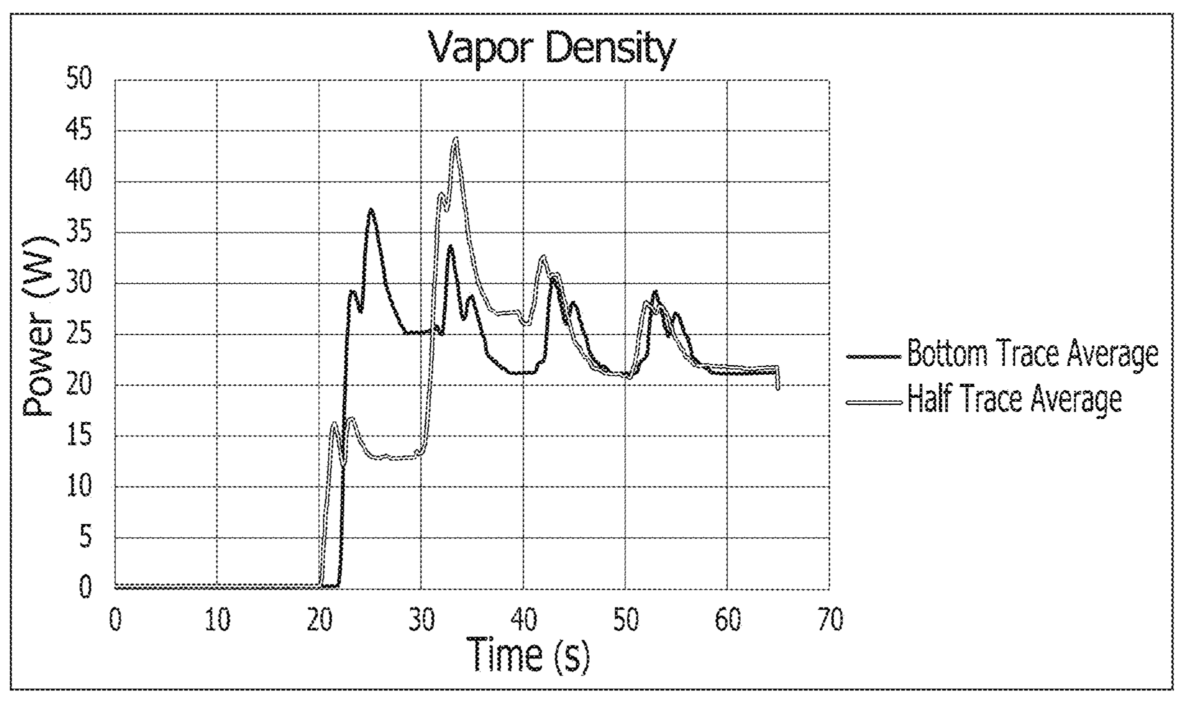
FIGS. 17-18 show the results of performance testing of a container having embedded heating traces in a lower region of the container sidewalls, versus a container having embedded heating traces in container sidewalls as well as in a container bottom wall.

FIG. 17 is a graph showing the average vapor density overtime as measured for runs using each of the "full trace" and "bottom-trace" containers. As can be seen from this figure, the device as run implementing the "half-trace" container yields slightly less vapor than the "bottom-trace" container (about 5% less). The data for each run is shown in Table 9 below, and the average vapor density different between containers is shown in Table 10.

TABLE 9

| Average Vapor Density | | | |
|---|---|---|---|
| Container | Run 1 | Run 2 | Run 3 |
| Bottom Trace | 22.29064 | 23.76017 | 27.39861 |
| Half Trace | 27.169 | 21.83472 | 20.60037 |

TABLE 10

| Vapor Density Comparison | | |
|---|---|---|
| Bottom Trace | Half Trace | % |
| 24.48314 | 23.20136 | −5.24 |

Figure 18:
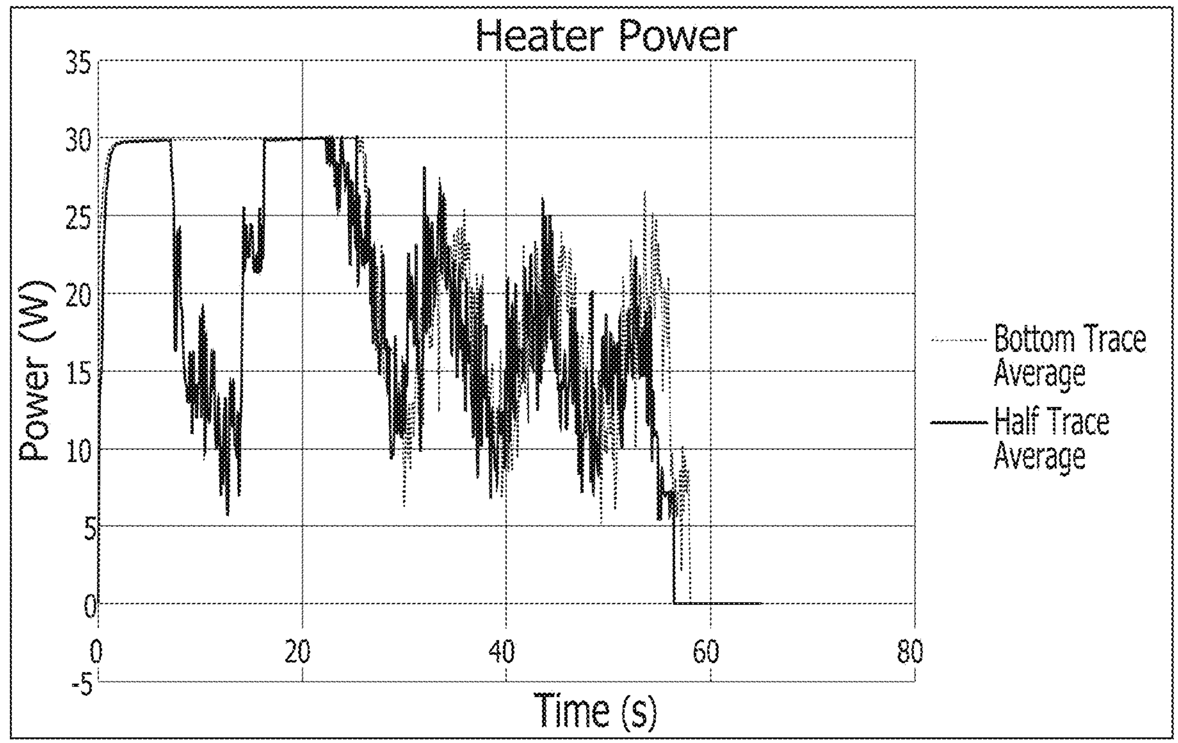

However, as shown in FIG. 18, the "half-trace" container unexpectedly exhibited performance improvements in terms of the power required to heat to the target temperature, as compared to the "bottom-trace" container. FIG. 18 is a graph showing the power output to the heating device to attain the target temperature as a function of time, and which shows that the "bottom-trace" heater required significantly more power to attain the target temperature than the "full-trace" heater. Tables 11 and 12 below show the average power required to achieve the targeted temperature using the "half-trace" versus the "bottom-trace" containers (Table 11), and the average difference in the average power between the "half-trace" and "bottom-trace" containers (Table 12). As shown in Table 12, the "half-trace" heater used about 16% less power than the "bottom-trace" heater to attain the same target temperature.

TABLE 11

| Average Power (W) | | | |
|---|---|---|---|
| Container | Run 1 | Run 2 | Run 3 |
| Bottom Trace | 19.45706 | 19.85336 | 19.85336 |
| Half Trace | 17.22524 | 16.33108 | 17.43475 |

TABLE 12

| Average Power Comparison (W) | | |
|---|---|---|
| Bottom Trace | Half Trace | % |
| 19.72126 | 16.99702 | −16.03 |

Furthermore, the "bottom-trace" heater required significantly more time to reach the target temperature than the "half-trace" heater (about 6% more time). Tables 13 and 14 below show the average time for each of the "half-trace" and "bottom-trace" containers to reach the target temperature (Table 13) and a comparison between the containers (Table 14).

TABLE 13

| Time to Reach Target Temperature (seconds) | | | |
|---|---|---|---|
| Container | Run 1 | Run 2 | Run 3 |
| Bottom Trace | 21.06587 | 21.18458 | 23.09251 |
| Half Trace | 21.56537 | 19.95577 | 19.93794 |

TABLE 14

| Comparison of Time to Reach Target Temperature (seconds) | | |
|---|---|---|
| Bottom Trace | Half Trace | % |
| 21.78099 | 20.48636 | −5.94 |

Accordingly, while the "half-trace" container produced slightly less vapor overall during each performance test, the "half-trace" container was surprisingly significantly more efficient than the "bottom-trace" heater in terms of the power and time required to attain a target temperature.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EMBODIMENTS

The Enumerated Embodiments 1-104 below set forth embodiments according to the disclosure.

Embodiment 1. A portable electronic vaporizing device comprising a removably attachable vaporization module, and a mouthpiece configured to receive a flow of gas having vaporized product entrained therein from the removably attachable vaporization module, wherein the mouthpiece comprises:

a mouthpiece housing at least partly defining an interior chamber;

an inhalation outlet formed in the mouthpiece housing; and a receiving area for receiving the removable battery-powered vaporization module in the interior chamber of the mouthpiece housing, and the removably attachable vaporization module comprises:

a base portion comprising:

a module housing having an insert portion configured to be at least partly received within the receiving area of the mouthpiece housing, the insert portion having one or more sealing regions configured to form a seal between the module housing and the mouthpiece housing, and a battery receiving area disposed within the insert portion and configured to receive a battery for powering the vaporization module; and a gas flow conduit having an input opening and an output opening positioned to output the flow of gas from the removably attachable vaporization module to the receiving area of the mouthpiece at an interior side of the seal between the module housing and the mouthpiece housing, and a vaporization assembly comprising;

a vaporization assembly housing;

a refillable container configured to receive a vaporizable product within the vaporization assembly housing;

a heating device configured to be electrically connected to the battery and transfer energy to the vaporizable product in the refillable container to heat the product and form a vapor therefrom;

an inlet configured to introduce gas into the refillable container;

one or more refillable container outlets configured to receive a flow of gas having vaporized product entrained therein from the refillable container; and one or more vaporization assembly outlets configured to provide the flow of gas received from the refillable container outlets to the input opening of the gas flow conduit in the base portion, wherein in operation of the portable electronic vaporizing device, the flow of gas having the vaporized product entrained therein is passed through the gas flow conduit and received into the receiving area of the mouthpiece from the output opening of the gas flow conduit, and is passed along the interior chamber of the mouthpiece to the inhalation outlet.

Embodiment 2. The portable electronic vaporizing device according to any preceding Embodiment, wherein the battery receiving area is configured to be entirely received within the receiving area of the mouthpiece, such that a battery received in the battery receiving area is enclosed by the walls of the mouthpiece.

Embodiment 3. The portable electronic vaporizing device according to any preceding Embodiment, wherein the mouthpiece housing at least partly defines an internal channel having a first end and a second end, the inhalation outlet is formed in the mouthpiece housing in the first end of the interior chamber, and the receiving area for receiving the removable battery-powered vaporization module is at the second end of the interior chamber within the mouthpiece housing.

Embodiment 4. The portable electronic vaporizing device according to any preceding Embodiment, wherein the vaporization assembly comprises an internal gas flow passage within the vaporization assembly housing configured to provide the flow of gas having the vaporized product entrained therein from the one or more refillable container outlets towards the one or more vaporization assembly outlets.

Embodiment 5. The portable electronic vaporizing device according to any preceding Embodiment, wherein at least one of the one or more vaporization assembly outlets is aligned with the input opening of the gas flow conduit in the base portion.

Embodiment 6. The portable electronic vaporizing device according to any preceding Embodiment, wherein at least a portion of the vaporization assembly connects to the base portion at an exterior side of the seal formed between the module housing and the mouthpiece housing.

Embodiment 7. The portable electronic vaporizing device according to any preceding Embodiment, wherein the vaporization assembly is removably attachable to the base portion.

Embodiment 8. The portable electronic vaporizing device according to Embodiment 7, wherein the base portion comprises sidewalls and a bottom wall defining a vaporization assembly receiving area configured to receive the vaporization assembly therein.

Embodiment 9. The portable electronic vaporizing device according to Embodiment 8, wherein the one or more vaporization assembly outlets are at a lower region of the assembly housing that is configured to be engaged to the input opening of the gas flow conduit, the input opening being formed in the bottom wall of the vaporization assembly receiving area of the base portion.

Embodiment 10. The portable electronic vaporizing device according to Embodiment 9, wherein the gas flow conduit extends from the input opening formed in the bottom wall of the vaporization assembly receiving area to the output opening, and wherein the output opening of the gas flow conduit is formed on an outer surface of the insert portion of the module housing and is radially external to the input opening.

Embodiment 11. The portable electronic vaporizing device according to any preceding Embodiment, wherein the inlet and the one or more refillable container outlets of the vaporization assembly are located towards a top of the refillable container, and wherein the one or more refillable container outlets of the vaporization assembly are located radially external to the inlet of the refillable container.

Embodiment 12. The portable electronic vaporizing device according to any preceding Embodiment, wherein the internal gas flow passage is defined between the vaporization assembly housing and walls of the refillable container, radially external to the refillable container, and wherein the internal gas flow passage redirects the flow of gas received from the one or more refillable container outlets in a direction towards the base portion of the battery-powered vaporization module.

Embodiment 13. The portable electronic vaporizing device according to any preceding Embodiment, wherein the one or more sealing regions comprise one or more sealing rings provided about a circumference of an outer surface of the insert portion, and which engage an inner surface of the mouthpiece housing in the receiving area to form the seal between the insert portion of the module housing and the inner surface of the mouthpiece housing.

Embodiment 14. The portable electronic vaporizing device according to any preceding Embodiment, wherein the seal formed between the module housing and mouthpiece housing at least partly defines the interior chamber of the mouthpiece for flow of the gas having the vaporized product entrained therein from the receiving area to the inhalation outlet.

Embodiment 15. The portable electronic vaporizing device according to any preceding Embodiment, wherein at least a portion of the battery receiving area of the removably attachable vaporization module is configured to be received in the receiving area at an interior side of the seal formed between the module housing and the mouthpiece housing.

Embodiment 16. The portable electronic vaporizing device according to any preceding Embodiment, wherein the heating device comprises at least one of a heating plate, a heating ring, and a heating element, and is capable of conductively heating the vaporizable product in the refillable container.

Embodiment 17. The portable electronic vaporizing device according to any preceding Embodiment, wherein at least a portion of the interior chamber of the mouthpiece is defined by a passage formed between portions of the mouthpiece housing and the surfaces of the insert portion.

Embodiment 18. The portable electronic vaporizing device according to any preceding Embodiment, wherein in operation of the device, the flow of gas having vaporized product entrained therein is flowed past at least a portion of the battery receiving area of the insert portion before reaching the inhalation outlet.

Embodiment 19. The portable electronic vaporizing device according to any preceding Embodiment, wherein the output opening of the gas flow conduit is positioned to output the flow of gas from the removably attachable vaporization module to one or more of: (i) a region of the receiving area adjacent the module housing, and between the module housing and the mouthpiece housing; and (ii) a region of the receiving area below the module housing.

Embodiment 20. The portable electronic vaporizing device according to any preceding Embodiment, wherein:

the refillable container is disposed above the battery receiving area of the insert portion;

the inlet to the refillable container has a diameter of at least 5 mm; and/or the inlet to the refillable container is disposed above the receiving area of the mouthpiece.

Embodiment 21. A method of using the portable electronic vaporizing device according to any preceding Embodiment, comprising:

inserting the removably attachable vaporization module into the receiving area of the mouthpiece;

providing vaporizable product to the product receiving chamber of the removably attachable vaporization module;

activating the heating device to heat the vaporizable product in the product receiving chamber to at least partly vaporize the product; and inhaling gas entrained with the vaporizable product from the inhalation outlet of the mouthpiece.

Embodiment 22. The method according to Embodiment 21, further comprising assembling the removably attachable vaporization module by inserting the removably attachable atomizer assembly into the receiving area of the base portion and aligning one or more of the vaporization assembly outlets with the gas flow conduit, either before or after insertion of the base portion of the removably attachable vaporization module into the receiving area of the mouthpiece.

Embodiment 23. A removably attachable base portion of a vaporization module for vaporizing a vaporizable product in a portable vaporizing device having a receiving body to receive the removably attachable base portion in a receiving region thereof, the removably attachable base portion comprising:

a housing having an insert portion configured to be at least partly received within the receiving area of the receiving body, the insert portion having one or more sealing regions configured to form a seal between the housing and one or more walls of the receiving body, and a battery receiving area disposed within the insert portion and configured to receive a battery for powering the vaporization module; and a gas flow conduit having an output opening positioned to output the flow of gas from the removably attachable base portion to the receiving area of the receiving body at an interior side of the seal between the housing and the one or more walls of the receiving body.

Embodiment 24. A removably attachable vaporization module comprising the removably attachable base portion of Embodiment 23, the removably attachable vaporization module further comprising:

a vaporization assembly comprising;

a vaporization assembly housing;

a refillable container configured to receive a vaporizable product within the vaporization assembly housing;

a heating device configured to be electrically connected to the battery and transfer energy to the vaporizable product in the refillable container to heat the product and form a vapor therefrom;

an inlet configured to introduce gas into the refillable container;

one or more refillable container outlets configured to receive a flow of gas having vaporized product entrained therein from the refillable container;

one or more vaporization assembly outlets configured to provide the flow of gas received from the refillable container outlets to the input opening of the gas flow conduit in the base portion, and optionally wherein the vaporization assembly is removably attachable to the base portion.

Embodiment 25. The removably attachable vaporization module of Embodiment 23 or 24, configured to be removably attached to a receiving body comprising a mouthpiece of a portable vaporizing device.

Embodiment 26. A container used to hold vaporizable product in a portable electronic vaporizing device, the container comprising:

container walls comprising one or more sidewalls and a bottom wall that form a space to receive the vaporizable product, and a heating device comprising one or more resistive heating elements embedded in one or more of the container walls, the heating device configured to be electrically connected to a battery and transfer energy to the vaporizable product in the container to heat the product and form a vapor therefrom.

Embodiment 27. The container according to Embodiment 26, wherein the bottom wall and lower regions of the one or more sidewalls form a continuous barrier to the passage of gas and/or liquid into or out of the container.

Embodiment 28. The container according to Embodiment 26 or 27, wherein the container is pre-filled with vaporizable product, or is a refillable container that is capable of being re-filled with vaporizable product.

Embodiment 29. The container according to any of Embodiments 26-28, wherein the bottom wall of the container and lower regions of the one or more sidewalls of the container are non-porous and/or wherein the container does not contain gas inlets and/or outlets on the bottom wall or lower regions of the one or more sidewalls.

Embodiment 30. The container according to any of Embodiments 26-29, wherein the bottom wall of the container and lower regions of the one or more sidewalls of the container are substantially and/or entirely impermeable to a flow of gas or liquid therethrough.

Embodiment 31. The container according to any of Embodiments 26-30, wherein the bottom wall of the container and lower regions of the one or more sidewalls of the container are configured to contain a vaporizable product that is liquid or that becomes at least partially liquefied during vaporization thereof.

Embodiment 32. The container according to any of Embodiments 26-31, wherein the heating device comprises one or more resistive heating elements embedded in sidewall heating portions of the one or more sidewalls.

Embodiment 33. The container according to any one of Embodiments 26-32, wherein the heating device comprises one or more resistive heating elements embedded in a bottom heating portion of the bottom wall.

Embodiment 34. The container according to any one of Embodiments 26-32, wherein the bottom wall of the container does not contain any resistive heating elements embedded therein, and/or does not contain any resistive heating elements adjacent the bottom wall.

Embodiment 35. The container according to any one of Embodiments 26-34, wherein the one or more container walls comprise a ceramic material comprising metal heater traces embedded therein.

Embodiment 36. The container according to any one of Embodiments 26-35, wherein the one or more container walls comprise a ceramic material comprising any of silicon carbide, alumina, aluminum nitride, zirconia, quartz, ruby, sapphire, bososilicate and combinations thereof, and metal heater traces comprising any of tungsten, kanthal, titanium, stainless steel, and nickel.

Embodiment 37. The container according to any one of Embodiments 26-36, wherein the resistive heating element is embedded in the one or more container walls such that a thickness of the one or more container walls on either side of the embedded resistive heating element is at least 0.1 mm, at least 0.15 mm, and/or at least 0.2 mm, and/or wherein the one or more container walls comprising the embedded resistive heating element comprise a thickness of at least 0.5 mm, at least 0.6 mm, and/or at least 0.8 mm Embodiment 38. The container according to any one of Embodiments 26-37, wherein the container is formed by embedding the resistive heating element in a soft ceramic material and forming a tube shape, adhering a thin ceramic bottom wall to the tube shape, and firing the soft ceramic tube shape with the resistive heating element embedded therein.

Embodiment 39 The container according to any one of Embodiments 26-38, wherein the container is formed by printing heater traces onto a first layer of soft ceramic material, covering the printed heater traces with a second layer of soft ceramic material to embed the printed heater traces between the first and second layers of the soft ceramic material, wrapping the first and second layers of soft ceramic material having the printed heater traces embedded therebetween into a tube shape, adhering a thin ceramic bottom wall to the tube shape, and firing the soft ceramic tube shape with the printed heater traces embedded therein.

Embodiment 40. The container according to any one of Embodiments 26-39, wherein the heating device comprises one or more resistive heating elements embedded in sidewall heating portions of the one or more sidewalls, wherein the one or more sidewalls extend vertically from the bottom wall to a vertical height $H_C$, and wherein the sidewall heating portions extend vertically from the bottom wall to a vertical height $H_D$ along the one or more sidewalls, and wherein the vertical height $H_D$ of the sidewall heating portions having the one or more heating elements embedded therein is lower than the height $H_C$ of the one or more sidewalls of the container.

Embodiment 41. The container of any one of Embodiments 26-40, wherein the bottom wall of the container has no heating device embedded therein.

Embodiment 42. The container of any one of Embodiments 26-41, wherein the vertical height $H_D$ of sidewall heating portions is lower than the height of the sidewalls $H_C$ of the container such that $H_D$ is less than 90%, less than 80%, less than 75%, less than 70%, less than 65%, less than 60%, less than 55%, less than 45%, less than 40%, less than 35%, and/or less than 30% of $H_C$.

Embodiment 43. The container of any one of Embodiments 26-42, wherein the vertical height $H_D$ of sidewall heating portions is lower than the height of the sidewalls $H_C$ of the container such that $H_D$ is at least 5%, at least 10%, at least 15%, at least 20%, at least 25%, at least 30%, at least 35%, at least 40%, at least 45%, and/or at least 50% of $H_C$.

Embodiment 44. The container of any one of Embodiments 26-43, wherein the one or more sidewalls of the container have an interior sidewall surface facing the interior of the container, and wherein a ratio of that portion of the interior sidewall surface corresponding to an interior surface of the sidewall heating portions having the embedded resistive heating elements, to the total interior sidewall surface is less than 90%, less than 80%, less than 75%, less than 70%, less than 65%, less than 60%, less than 55%, less than 45%, less than 40%, less than 35%, and/or less than 30%.

Embodiment 45. The container of Embodiment 44, wherein sidewall portions of the container without resistive heating elements embedded therein have an interior surface area, which makes up at least 5%, at least 10%, at least 15%, at least 20%, at least 25%, at least 30%, at least 35%, at least 40%, at least 45%, at least 50%, at least 55%, and/or at least 60% of the total interior sidewall surface area.

Embodiment 46. The container of any one of Embodiments 26-45, wherein the container comprises an interior container surface comprising an interior sidewall surface and an interior surface area of the bottom wall, and wherein a surface area of that portion of the interior sidewall surface corresponding to an interior surface of the sidewall heating portions is less than 90%, less than 80%, less than 75%, less than 70%, less than 65%, less than 60%, less than 55%, less than 45%, less than 40%, less than 35%, and/or less than 30% of the interior container surface area.

Embodiment 47. The container of any of Embodiments 26-46, wherein sidewall portions of the container without resistive heating elements embedded therein have an interior surface, which makes up at least 5%, at least 10%, at least 15%, at least 20%, at least 25%, at least 30%, at least 35%, at least 40%, at least 45%, at least 50%, at least 55%, and/or at least 60% of the interior container surface area.

Embodiment 48. The container of any one of Embodiments 26-47, wherein during operation, the sidewall heating portions are heated to a temperature higher than that of the bottom wall and the sidewall portions without resistive heating elements embedded therein.

Embodiment 49. The container of any one of Embodiments 26-48, wherein a power delivered to the resistive heating elements in the sidewall heating portions is greater than any power delivered to resistive heating elements in the bottom wall, and/or no power is delivered to any resistive heating elements in the bottom wall.

Embodiment 50. The container according to any one of Embodiments 26-49, wherein the container comprises sidewall and bottom wall heating portions comprising resistive heating elements embedded therein, and wherein resistive heating elements embedded in the bottom wall heating portions comprise a higher resistance than resistive heating elements embedded in the one or more sidewall heating portions.

Embodiment 51. The container of any one of Embodiments 26-50, wherein the sidewall heating portions comprise a height $H_D$ of no more than 10 mm, no more than 9 mm, no more than 8 mm, no more than 7.5 mm, and/or no more than 7.5 mm, as measured from the bottom wall, and can comprise a height of at least 2 mm, at least 2.5 mm, at least 3 mm, at least 4 mm, at least 5 mm, at least 5.5 and/or at least 5.75 mm, as measured from the bottom wall.

Embodiment 52. The container of any one of Embodiments 26-51, wherein the one or more heating elements comprising one or more heater traces extend at least partly circumferentially about the interior of the container.

Embodiment 53. The container of Embodiment 52, wherein the one or more heater traces form a switchback pattern across at least a portion of the sidewall heater portions.

Embodiment 54. The container of any one of Embodiments 52-53, wherein the one or more heater traces comprise a plurality of substantially horizontal segments at least partly circumferentially surrounding the interior of the container, and comprise a plurality of substantially vertical segments connecting the substantially horizontal segments.

Embodiment 55. A portable electronic vaporizing device comprising the container according to any one of Embodiments 26-55.

Embodiment 56. A portable electronic vaporizing device according to Embodiment 55, wherein the portable electronic vaporizing device comprises a mouthpiece configured to receive vaporizable product that is vaporized in the container, the mouthpiece having an inhalation outlet for inhaling of the vaporized product.

Embodiment 57. The portable electronic vaporizing device according to any one of Embodiments 55-57, wherein portable electronic vaporizing device comprises:

a base having a gas flow path conduit therein and a housing for one or more components for powering and/or controlling the device, the gas flow path conduit comprising a conduit inlet and a conduit outlet;

a mouthpiece that is removably attachable to the base, the mouthpiece comprising:

a mouthpiece housing comprising one or more mouthpiece walls at least partly defining a mouthpiece internal flow path through the mouthpiece housing;

an inhalation outlet formed in a region of the one or more mouthpiece walls; and at least one mouthpiece inlet capable of being placed in communication with the conduit outlet of the base upon attachment of the mouthpiece to the base, to receive a flow of gas into the mouthpiece from the base; and an atomizer that is removably attachable to the base, the atomizer comprising:

an atomizer inlet configured to receive a flow of gas into the atomizer;

an atomizer housing comprising one or more atomizer housing walls that at least partially define an atomizer internal flow path therein;

a container within the atomizer housing that is capable of holding a vaporizable product, the container corresponding to that of any of Embodiments 26-54, a heating element capable of heating the vaporizable product held in the container, the heating element being configured to be electrically connected to the one or more components for powering and/or controlling the device that are housed in the base;

a first container inlet capable of introducing gas into the container to entrain vaporizable product;

one or more second container outlets capable of flowing the gas having the vaporizable product entrained therein into atomizer internal flow path; and one or more atomizer outlets capable of receiving the flow of gas from the atomizer internal flow path, and providing the flow of gas to the conduit inlet of the base, wherein at least a portion of the atomizer internal flow path in the atomizer is defined between the one or more atomizer housing walls and one or more sidewalls of the container, and wherein the flow of gas having the vaporizable product entrained therein flows from the atomizer internal flow path and through the gas flow conduit inlet of the base to the mouthpiece inlet, and along the mouthpiece internal flow path to the inhalation outlet.

Embodiment 58. The portable electronic vaporizing device according to Embodiment 57, wherein the atomizer is removable from the base independently of removal of the mouthpiece.

Embodiment 59. The portable electronic vaporizing device according to any one of Embodiments 57-58, wherein the base comprises a first recessed receiving region formed therein that is configured to removably receive the atomizer, and a second recessed receiving region formed therein that is configured to removably receive the mouthpiece.

Embodiment 60. The portable electronic vaporizing device according to any of Embodiments 57-59, wherein an airtight seal is formed between the between the base and the atomizer and/or between the base and the mouthpiece, in one or more of the first and second recessed receiving regions.

Embodiment 61. The portable electronic vaporizing device according to Embodiment 59, wherein the base comprises one or more of (i) at least one conformal liner disposed in the first recessed receiving region that is configured to conformally receive at least a portion of the atomizer, and (ii) at least one conformal liner disposed in the second recessed receiving region that is configured to conformally receive at least a portion of the mouthpiece.

Embodiment 62. The portable electronic vaporizing device according to Embodiment 61, wherein the base comprises the at least one conformal liner disposed in the second recessed receiving region that is configured to conformally receive an outer circumferential surface of a fastening region located at a lower portion of the mouthpiece.

Embodiment 63. The portable electronic vaporizing device according to any of Embodiments 57-62, wherein the atomizer comprises a heating element disposed below a bottom surface of the container that adapted to receive the vaporizable product.

Embodiment 64. The portable electronic vaporizer device according to any of Embodiments 57-65, wherein the one or more second container outlets in the atomizer that flow the gas having the vaporizable product entrained therein out of the container and into the atomizer internal flow path, are located towards a top end of the atomizer and radially externally to the first container inlet, and are positioned in an arrangement circumferentially surrounding the first container inlet.

Embodiment 65. The portable electronic vaporizing device according to Embodiment 64, wherein the one or more second container outlets comprise one or more of:

(i) one or more apertures formed in one or more walls located at an upper portion of the container;

(ii) one or more apertures formed between a top surface of the container and an annular ring disposed above the container, the annular ring comprising one or more indentations formed in a bottom surface about a circumference thereof that form the one or more apertures between the bottom surface of the annular ring and the top surface of the container; and (iii) one or more apertures formed about a circumference of an annular ring disposed above the container.

Embodiment 66. The portable electronic vaporizer device according to any of Embodiments 57-65, wherein the flow of gas through the atomizer comprises flow through the first container inlet into a top of the container, flow out of the container through the second container outlets that are separate from the inlet and disposed towards a top end of the atomizer, and wherein the atomizer housing at least partially directs gas from the one or more second container gas outlets along the internal atomizer gas flow path, in a passage formed between walls of the container and the atomizer housing, and wherein the atomizer housing comprises one or more apertures formed therein to flow gas from the internal atomizer gas flow path to an airtight passage that is external to the atomizer housing in a first recessed receiving region of the base.

Embodiment 67. The portable electronic vaporizer device according to any of Embodiments 57-66, wherein the mouthpiece internal flow path comprises a convoluted flow path from the at least one mouthpiece inlet to the inhalation outlet, the mouthpiece comprising a first chamber that is internal to a second chamber that at least partially circumferentially surrounds the first chamber, and wherein the flow of gas along the mouthpiece internal flow path is received in the at least one mouthpiece inlet, passes through the first chamber and into the second chamber, and out of the inhalation outlet.

Embodiment 68. A portable electronic vaporizing device comprising a removably attachable vaporization module, and a mouthpiece configured to receive a flow of gas having vaporizable product entrained therein from the removably attachable vaporization module, wherein the mouthpiece comprises:

a mouthpiece housing at least partly defining an interior chamber;

an inhalation outlet formed in the mouthpiece housing; and a receiving area for receiving the removable battery-powered vaporization module in the interior chamber of the mouthpiece housing, and the removably attachable vaporization module comprises:

a base portion comprising:

a module housing having an insert portion configured to be at least partly received within the receiving area of the mouthpiece housing, the insert portion having one or more sealing regions configured to form a seal between the module housing and the mouthpiece housing, and a battery receiving area disposed within the insert portion and configured to receive a battery for powering the vaporization module; and a gas flow conduit having an input opening and an output opening positioned to output the flow of gas from the removably attachable vaporization module to the receiving area of the mouthpiece at an interior side of the seal between the module housing and the mouthpiece housing, and a vaporization assembly comprising:

a vaporization assembly housing;

a container according to any one of Embodiments 26-54, configured to receive a vaporizable product within the vaporization assembly housing;

an inlet configured to introduce gas into the container;

one or more container outlets configured to receive a flow of gas having vaporized product entrained therein from the container; and one or more vaporization assembly outlets configured to provide the flow of gas received from the container outlets to the input opening of the gas flow conduit in the base portion, wherein in operation of the portable electronic vaporizing device, the flow of gas having the vaporized product entrained therein is passed through the gas flow conduit and received into the receiving area of the mouthpiece from the output opening of the gas flow conduit, and is passed along the interior chamber of the mouthpiece to the inhalation outlet.

Embodiment 69. A portable vaporizing device according to any of Embodiments 55-56 or 68, wherein the device corresponds to any recited in Embodiments 2-22.

Embodiment 70. A method of using the portable vaporizing device according to any one of Embodiments 55-69, comprising:

providing vaporizable product to the container;

activating the heating device to heat the vaporizable product in the container to at least partly vaporize the product; and inhaling gas entrained with the vaporized product via the portable vaporizing device.

Embodiment 71. The method of Embodiment 70, wherein the vaporizable product is provided to the container to fill up the container to a height of no more than $H_D$.

Embodiment 72. A method of using the container according to any one of Embodiments 26-54 in a portable vaporizing device corresponding to any of Embodiments 55-69, comprising:

providing vaporizable product to the container;

activating the heating device to heat the vaporizable product in the container to at least partly vaporize the product; and inhaling gas entrained with the vaporized product via the portable vaporizing device.

Embodiment 73. The method of Embodiment 72, wherein the vaporizable product is provided to the container to fill up the container to a height of no more than $H_D$.

Embodiment 74. A vaporization assembly for an electronic vaporizing device according to any one of Embodiments 1-22, the vaporization assembly comprising:

a vaporization assembly housing;

the container according to any one of Embodiments 26-54, the container being configured to receive a vaporizable product within the vaporization assembly housing, the container including the heating device configured to be electrically connected to the battery and transfer energy to the vaporizable product in the container to heat the product and form a vapor therefrom;

an inlet configured to introduce gas into the container;

one or more container outlets configured to receive a flow of gas having vaporized product entrained therein from the container; and one or more vaporization assembly outlets configured to output the flow of gas received from the container outlets, wherein during use of the vaporization assembly in the electronic vaporizing device, the flow of gas output by the one or more vaporization assembly outlets is received by a mouthpiece of the electronic vaporizing device.

Embodiment 75. A removably attachable atomizer for an electronic vaporizing device, the atomizer comprising:

an atomizer inlet configured to receive a flow of gas into the atomizer;

an atomizer housing comprising one or more atomizer housing walls that at least partially define an atomizer internal flow path therein;

the container according to any one of Embodiments 26-54 within the atomizer housing that is capable of holding a vaporizable product, the container comprising the heating device having the heating element capable of heating the vaporizable product held in the container, the heating device being configured to be electrically connected to a battery and transfer energy to the vaporizable product in the container to heat the product and form a vapor therefrom, a first container inlet capable of introducing gas into the container to entrain vaporizable product;

one or more second container outlets capable of flowing the gas having the vaporizable product entrained therein, one or more atomizer outlets capable of receiving the flow of gas from the atomizer internal flow path, and outputting the flow of gas from the atomizer internal flow path, wherein during use of the atomizer in the electronic vaporizing device, the flow of gas output by the one or more atomizer outlets is received by a mouthpiece of the electronic vaporizing device.

Embodiment 76 removably attachable base portion of a vaporization module for vaporizing a vaporizable product in a portable vaporizing device, according to any of Embodiments 23-25, comprising the container of any of Embodiments 26-54.

Embodiment 77. A battery-powered vaporization module configured to attach to and form an air tight seal with a mouthpiece, the mouthpiece comprising a mouthpiece housing at least partly defining an interior chamber, and an inhalation outlet in communication with the interior chamber, the battery-powered vaporization module comprising:

a vaporization assembly configured to heat a vaporizable product to form a vaporized product therefrom;

a base portion comprising a battery storage compartment configured to store a battery to power the battery-powered vaporization module, the base portion being configured such that the battery storage compartment is received within the interior chamber of the mouthpiece housing when the battery-powered vaporization module is attached to the mouthpiece; and wherein, during use of the battery-powered vaporization module, gas entrained with vaporized product flows from the vaporization assembly to the interior chamber of the mouthpiece and exits the mouthpiece via the inhalation outlet.

Embodiment 78. The battery-powered vaporization module according to Embodiment 77, wherein the vaporization module comprises a container configured to hold a vaporizable product, and wherein the container is pre-filled with the vaporizable product or is a refillable container.

Embodiment 79. The battery-powered vaporization module according to any of Embodiments 77 and 78, wherein the base portion is disposed below the vaporization assembly.

Embodiment 80. The battery-powered vaporization module according to any of Embodiments 77-79, wherein the module is configured to be removably attachable to any of a plurality of different mouthpieces with mouthpiece housings having different shapes and sizes.

Embodiment 81. The battery-powered vaporization module according to any of Embodiments 77-80, wherein the module is configured to attach to the mouthpiece housing such that a volume of the base portion containing the battery storage compartment is at least 10%, at least 25%, at least 30%, at least 50%, at least 60%, at least 75%, at least 80%, and/or at least 90% surrounded by the mouthpiece housing when the module is attached to the mouthpiece.

Embodiment 82. The battery-powered vaporization module according to any of Embodiments 77-81, wherein the module is configured to attach to the mouthpiece housing such that the mouthpiece housing extends over a bottom surface of the base portion, as well as about one or more sides of the base portion.

Embodiment 83. The battery-powered vaporization module according to any of Embodiments 77-82, wherein the module is configured to attach to the mouthpiece housing such that no more than 75%, no more than 60%, no more than 50%, no more than 35%, no more than 25%, no more than 10% and/or no more than 5% of a volume of the battery compartment extends outside mouthpiece housing.

Embodiment 84. The battery-powered vaporization module according to any of Embodiments 77-83, wherein the module is configured to attach to the mouthpiece housing such that no more than 75%, no more than 60%, no more than 50%, no more than 35%, no more than 25%, no more than 10% and/or no more than 5% of a vertical height of the battery compartment extends above a top surface of the mouthpiece housing.

Embodiment 85. The battery-powered vaporization module according to any of Embodiments 77-84, wherein the module is configured to attach to the mouthpiece housing such that the battery compartment does not extend outside mouthpiece housing.

Embodiment 86. The battery-powered vaporization module according to any of Embodiments 77-85, wherein the module is configured to attach to the mouthpiece housing such that the battery compartment does not extend above a top surface of the mouthpiece housing.

Embodiment 87. The battery-powered vaporization module according to any of Embodiments 77-86, wherein the bottom portion comprising the battery storage compartment is configured to be received within the interior chamber of the mouthpiece housing by loading the battery storage compartment into the interior chamber through a mouthpiece module receiving opening that is located at any of a top of the mouthpiece, a bottom of the mouthpiece, and/or a side of the mouthpiece.

Embodiment 88. The battery-powered vaporization module according to any of Embodiments 77-87, wherein the module is configured to attach to the mouthpiece housing such that, during use of the module, vaporized product is received in the interior chamber at a region that is to the side of the battery compartment.

Embodiment 89. The battery-powered vaporization module according to any of Embodiments 77-88, wherein the module is configured to attach to the mouthpiece housing such that, during use of the module, vaporized product is received in the interior chamber at a region that is below battery compartment.

Embodiment 90. The battery-powered vaporization module according to any of Embodiments 77-89, wherein the module is configured to attach to the mouthpiece housing such that, during use of the module, a flow of vaporized product is directed past a side or beneath the battery compartment within the interior chamber.

Embodiment 91. The battery-powered vaporization module according to any of Embodiments 77-90, wherein the module is configured to attach to the mouthpiece housing such that surfaces of one or more portions of the base portion that are to a side or beneath the battery compartment form a gas flow path in the interior chamber with the mouthpiece housing.

Embodiment 92. The battery-powered vaporization module according to any of Embodiments 77-91, wherein the battery storage compartment is completely received within the mouthpiece housing when the module is attached to the mouthpiece.

Embodiment 93. The battery-powered vaporization module according to any of Embodiments 77-92, wherein the base portion is releasably attachable to the vaporization assembly, and wherein the base portion comprises an attachment region configured to receive the vaporization assembly at an upper region of the base portion.

Embodiment 94. The battery-powered vaporization module according to any of Embodiments 77-93, wherein the module comprises one or more sealing regions configured to engage the mouthpiece housing to form the air-tight seal about the interior chamber of the mouthpiece housing when the battery-powered vaporization module is attached to the mouthpiece.

Embodiment 95. The battery-powered vaporization module according to Embodiment 94, wherein a top surface of the vaporization assembly is either flush with or extends above the one or more sealing regions.

Embodiment 96. The battery-powered vaporization module according to any of Embodiments 77-95, wherein a top surface of the vaporization assembly is flush with or extends above a top surface of the mouthpiece housing.

Embodiment 97. The battery-powered vaporization module according to any of Embodiments 77-96, wherein the vaporization assembly comprises a refillable container to receive the vaporizable product, and wherein the refillable container is flush with or extends above a top surface of the mouthpiece housing, and/or is flush with or extends above one or more sealing regions of the module that engage the mouthpiece housing to form the air-tight seal about the interior chamber of the mouthpiece housing.

Embodiment 98. The battery-powered vaporization module according to any of Embodiments 77-97, wherein the vaporization assembly comprises a refillable container configured to receive a vaporizable product within the vaporization assembly housing, and wherein the module is configured to attach to the mouthpiece housing such that the refillable container can be accessed for loading and unloading of the vaporizable product while maintaining the air tight seal between the module and the mouthpiece housing.

Embodiment 99. The battery-powered vaporization module according to any of Embodiments 77-98, wherein the vaporization assembly comprises:

- a vaporization assembly housing;
- a refillable container configured to receive a vaporizable product within the vaporization assembly housing;
- a heating device configured to be electrically connected to the battery and transfer energy to the vaporizable product in the refillable container to heat the product and form a vapor therefrom;
- a refillable container inlet configured to introduce gas into the refillable container; and
- one or more refillable container outlets configured to receive gas having vaporized product entrained therein from the refillable container.

Embodiment 100. A portable electronic vaporizing device comprising the battery-powered vaporization module of any of Embodiments 77-99, and the mouthpiece comprising the mouthpiece housing defining the interior chamber, and inhalation outlet.

Embodiment 101. A battery-powered vaporization module of any of Embodiments 77-100, or the portable electronic vaporizing device of Embodiment 100, wherein the portable electronic vaporizing device comprises any recited in Embodiments 1-20 and 68, and/or the module comprises any recited in Embodiments 23-25, and/or the vaporization assembly for the module comprises the vaporization assembly recited in Embodiments and 74.

Embodiment 102. A method of using the battery-powered vaporization module or device of any of Embodiments 77-101, the method comprising attaching the module to the mouthpiece housing to form the air tight seal, loading vaporizable product to the vaporization assembly to generated a vaporized product, and inhaling the vaporized product through the inhalation outlet.

Embodiment 103. A method of using the battery-powered vaporization module of any of Embodiments 77-101, the method comprising:

- inserting the battery-powered vaporization module into a mouthpiece;
- heating a vaporizable product in the vaporization assembly to form a vaporized product therefrom; and
- removing the battery-powered vaporization module from the mouthpiece.

Embodiment 104. A method according to Embodiment 103, wherein the mouthpiece comprises a first mouthpiece having a first mouthpiece housing with a first size, shape and/or configuration, and wherein the method further comprises inserting the battery-powered vaporization module into a second mouthpiece with a second mouthpiece housing having a size, shape and/or configuration that is different that the first mouthpiece.

EQUIVALENTS

While specific embodiments have been discussed, the above specification is illustrative, and not restrictive. Many variations will become apparent to those skilled in the art upon review of this specification. The full scope of the embodiments should be determined by reference to the claims, along with their full scope of equivalents, and the specification, along with such variations.

What is claimed is:

1. A removably attachable atomizer for an electronic vaporizing device, the removably attachable atomizer comprising:

a container configured to hold vaporizable product, wherein the container comprises:

container walls comprising one or more sidewalls and a bottom wall that form a space to receive the vaporizable product, and a heating device comprising one or more resistive heating elements embedded in one or more of the sidewalls, the heating device configured to be electrically connected to a power source and transfer energy to the vaporizable product in the container to heat the vaporizable product and form a vaporized product therefrom, wherein the one or more resistive heating elements are embedded in sidewall heating portions of the one or more sidewalls of the container, wherein the one or more sidewalls extend vertically from the bottom wall to a vertical height $H_C$, and wherein the sidewall heating portions extend vertically from the bottom wall to a vertical height $H_D$ along the one or more sidewalls, wherein the bottom wall of the container does not contain gas inlets and/or outlets, and wherein:

the heating device is configured such that the sidewall heating portions are heated to a higher temperature than the bottom wall during operation of the atomizer.

2. The atomizer according to claim 1, further comprising an atomizer inlet configured to receive a flow of gas into a top of the atomizer, to provide the flow of gas to the container, and one or more atomizer outlets located towards a bottom of the atomizer that are capable of receiving the gas having the vaporized product entrained therein from the container.

3. The atomizer according to claim 2, wherein the container comprises (i) a container inlet capable of introducing the flow of gas provided by the atomizer inlet into the container from a top of the container to entrain the vaporized product, and (ii) one or more container outlets capable of exhausting the gas having the vaporized product entrained therein from the top of the container.

4. The atomizer according to claim 3, wherein the one or more container outlets are located near the top of the container.

5. The atomizer according to claim 3, wherein the one or more container outlets are located radially external to the container inlet.

6. The atomizer according to claim 1, wherein the one or more resistive heating elements extend at least partly circumferentially about an interior of the container.

7. The atomizer according to claim 1, wherein the one or more resistive heating elements are partly covered by one or more materials forming the container walls, such that the one or more resistive heating elements are at least partly exposed to the environment external to the container.

8. The atomizer according to claim 1, wherein the container is pre-filled with vaporizable product, or is a refillable container that is capable of being re-filled with vaporizable product.

9. The atomizer according to claim 1, wherein the bottom wall of the container and the one or more sidewalls of the container are configured to contain a vaporizable product that is liquid or that becomes at least partially liquefied during vaporization thereof.

10. The atomizer according to claim 1, wherein the bottom wall of the container does not contain any resistive heating elements embedded therein, and/or the container does not contain any resistive heating elements adjacent to the bottom wall.

11. The atomizer according to claim 1, wherein the container walls comprise a ceramic material having metal heater traces embedded therein.

12. The atomizer according to claim 11, wherein the container walls comprise a ceramic material comprising any of silicon carbide, alumina, aluminum nitride, zirconia, quartz, ruby, sapphire, bososilicate and combinations thereof, and the metal heater traces comprising any of tungsten, kanthal, titanium, stainless steel, and nickel.

13. The atomizer according to claim 11, wherein the heater traces form a switchback pattern across at least a portion of sidewall heating portions of the one or more sidewalls of the container.

14. The atomizer according to claim 11, wherein the heater traces comprise a plurality of substantially horizontal segments at least partly circumferentially surrounding an interior of the container, and comprise a plurality of substantially vertical segments connecting the substantially horizontal segments.

15. The atomizer according to claim 1, wherein the one or more resistive heating elements are embedded in the one or more sidewalls of the container such that a thickness of the one or more sidewalls on either side of the embedded one or more resistive heating elements is at least 0.1 mm, at least 0.15 mm, and/or at least 0.2 mm, and/or wherein the one or more sidewalls comprising the embedded one or more resistive heating elements comprise a thickness of at least 0.5 mm, at least 0.6 mm, and/or at least 0.8 mm.

16. The atomizer according to claim 1, wherein the container is formed by embedding the one or more resistive heating elements in a soft ceramic material and forming a tube shape, adhering a thin ceramic bottom wall to the tube shape, and firing the soft ceramic tube shape with the one or more resistive heating element embedded therein.

17. The atomizer according to claim 1, wherein the container is formed by printing heater traces onto a first layer of soft ceramic material, covering the printed heater traces with a second layer of soft ceramic material to embed the printed heater traces between the first and second layers of soft ceramic material, wrapping the first and second layers of soft ceramic material having the printed heater traces embedded therebetween into a tube shape, adhering a thin ceramic bottom wall to the tube shape, and firing the soft ceramic tube shape with the printed heater traces embedded therein.

18. The atomizer according to claim 1, wherein the bottom wall of the container has no heating device embedded therein.

19. The atomizer according to claim 1, wherein the vertical height $H_D$ of the sidewall heating portions having the one or more resistive heating elements embedded therein is lower than 55% of the height $H_C$ of the one or more sidewalls of the container.

20. The atomizer according to claim 1, wherein the vertical height $H_D$ of sidewall heating portions having the one or more resistive heating elements embedded therein is lower than 45% of the height $H_C$ of the one or more sidewalls of the container.

21. The atomizer according to claim 1, wherein the vertical height $H_D$ of sidewall heating portions is at least 20% of $H_C$.

22. The atomizer according to claim 1, wherein the one or more sidewalls of the container have an interior sidewall surface facing an interior of the container, and wherein a ratio of that portion of the interior sidewall surface corresponding to an interior surface of sidewall heating portions having the embedded one or more resistive heating elements, to the total interior sidewall surface is less than 55%.

23. The atomizer according to claim 1, wherein sidewall portions of the container without resistive heating elements embedded therein have an interior surface area, which makes up at least 20% of the total interior sidewall surface area.

24. The atomizer according to claim 1, wherein the heating device is configured such that a power delivered to the one or more resistive heating elements embedded in the sidewall heating portions during operation of the atomizer is greater than any power delivered to the bottom wall, and/or no power is delivered to the bottom wall.

25. The atomizer according to claim 1, wherein the sidewall heating portions comprise a height $H_D$ of no more than 7.5 mm, as measured from the bottom wall, and comprise a height $H_D$ of at least 3 mm as measured from the bottom wall.

26. An electronic vaporizing device comprising the atomizer according to claim 1.

27. The device according to claim 26, further comprising:

a base configured to receive the atomizer, having a gas flow path conduit therein, and a mouthpiece that is removably attachable to the base, comprising a mouthpiece inlet and an inhalation outlet, wherein a flow of gas having the vaporized product entrained therein flows from the atomizer and through the gas flow conduit inlet of the base to the mouthpiece inlet, and along the mouthpiece to the inhalation outlet.

* * * * *